(12) United States Patent
Basham et al.

(10) Patent No.: US 9,517,985 B2
(45) Date of Patent: Dec. 13, 2016

(54) METHOD FOR PRODUCING BUTANOL USING EXTRACTIVE FERMENTATION

(71) Applicant: Butamax Advanced Biofuels LLC, Wilmington, DE (US)

(72) Inventors: Thomas Basham, San Diego, CA (US); Leslie William Bolton, Hampshire (GB); Ian David Dobson, London (GB); Sarah Richardson Hanson, San Marcus, CA (US); Aidan Hurley, East Riding of Yorkshire (GB); Karen Kustedjo, La Jolla, CA (US); Andrew Richard Lucy, Brough East Yorkshire (GB); Liang Song, San Diego, CA (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 14/772,705

(22) PCT Filed: Mar. 14, 2014

(86) PCT No.: PCT/US2014/029142
§ 371 (c)(1),
(2) Date: Sep. 3, 2015

(87) PCT Pub. No.: WO2014/144643
PCT Pub. Date: Sep. 18, 2014

(65) Prior Publication Data
US 2016/0016870 A1      Jan. 21, 2016

Related U.S. Application Data

(60) Provisional application No. 61/788,213, filed on Mar. 15, 2013.

(51) Int. Cl.
| C07C 31/12 | (2006.01) |
| C12P 7/16 | (2006.01) |
| C07C 29/76 | (2006.01) |
| C07C 29/86 | (2006.01) |

(52) U.S. Cl.
CPC .............. *C07C 29/76* (2013.01); *C07C 29/86* (2013.01); *C07C 31/12* (2013.01); *C12P 7/16* (2013.01); *Y02E 50/10* (2013.01)

(58) Field of Classification Search
CPC .................................. C07C 31/12; C12P 7/16
USPC .......................... 568/840, 913; 435/160, 243
See application file for complete search history.

(56) References Cited

U.S. PATENT DOCUMENTS

| 4,428,798 A | 1/1984 | Zudkevitch et al. |
| 4,636,284 A | 1/1987 | English et al. |
| 4,865,973 A | 9/1989 | Kollerup et al. |
| 5,374,716 A | 12/1994 | Biermann et al. |
| 7,851,188 B2 | 12/2010 | Donaldson et al. |
| 8,373,008 B2 | 2/2013 | Grady et al. |
| 8,373,009 B2 | 2/2013 | Grady et al. |
| 8,409,834 B2 | 4/2013 | Burlew et al. |
| 8,426,173 B2 | 4/2013 | Bramucci et al. |
| 8,426,174 B2 | 4/2013 | Bramucci et al. |
| 8,460,439 B2 | 6/2013 | Parten |
| 8,476,047 B2 | 7/2013 | Burlew et al. |
| 8,557,540 B2 | 10/2013 | Burlew et al. |
| 8,563,788 B2 | 10/2013 | Grady et al. |
| 8,569,552 B2 | 10/2013 | Grady et al. |
| 8,574,406 B2 | 11/2013 | Grady et al. |
| 8,617,861 B2 | 12/2013 | Grady et al. |
| 8,628,643 B2 | 1/2014 | Grady et al. |
| 8,697,404 B2 | 4/2014 | Anton et al. |
| 8,759,044 B2 | 6/2014 | DiCosimo et al. |
| 8,765,425 B2 | 7/2014 | DiCosimo et al. |
| 8,828,695 B2 | 9/2014 | Grady et al. |
| 8,865,443 B2 | 10/2014 | Burlew et al. |
| 8,906,204 B2 | 12/2014 | Xu |
| 8,968,522 B2 | 3/2015 | Xu et al. |
| 8,968,523 B2 | 3/2015 | Xu et al. |
| 8,969,055 B2 | 3/2015 | Grady et al. |
| 2008/0274526 A1 | 11/2008 | Bramucci et al. |
| 2009/0305370 A1 | 12/2009 | Grady et al. |
| 2010/0143995 A1 | 6/2010 | Erdner-Tindall et al. |
| 2011/0097773 A1* | 4/2011 | Grady .................... C07C 29/86 435/160 |
| 2011/0136193 A1 | 6/2011 | Grady et al. |

(Continued)

FOREIGN PATENT DOCUMENTS

| GB | 1064317 | 4/1967 |
| JP | 60172290 | 9/1985 |

(Continued)

OTHER PUBLICATIONS

Adhami, et al., Liquid-Liquid Extraction of Butanol from Dilute Aqueous Solutions Using Soybean-Derived Biodiesel, J. Am. Oil Chem. Soc. 86:1123-1128, 2009.
Jurgens, et al., Butanol Production from Lingocellulosics, Biotechnol. Lett. 34:1415-1434, 2012.
Kim, et al., Extractive Recovery of Products from Fermentation Broths, Biotechnol, Bioprocess Eng. 4:1-11, 1999.
Bumbac, et al., Process Modelling and Simulation for 1-Butanol Removing from Fermentation Broth by Extraction with Oleyl Alcohol, Rev. Chirn, (Bucharest) 63:727-729, 2012.
Oudshoorn, et al., Short-cut Calculation for Integrated Product Recovery Options in Fermentative Production of Bio-bulk Chemicals, Proc, Blochem. 45:1605-1615, 2010.
Offeman, et al., Extraction of Ethanol with Higher Alcohol Solvents and Their Toxicity to Yeast, Sep. Purif. Technol. 63:444-451, 2008.
Dhamole, et al., Extractive Fermentation with Non-ionic Surfactants to Enhance Butanol Production, Biomass Bioenerg. 40:112-119, 2012.
Atsumi, et al., Non-fermentative pathways for synthesis of branched-chain higher alcohols as biofuels, Nature 451:86-90, 2008.
Banik, et al., Technological aspects of extractive fermentation using aqueous two-phase systems, World J. Microbiol, Biotechnol. 19:337-348, 2003.

(Continued)

*Primary Examiner* — Elvis O Price

(57) ABSTRACT

The invention relates to a method for producing butanol through microbial fermentation, in which the butanol product is removed by extraction into a water immiscible organic extractant during the fermentation. The invention also relates to a method for producing butanol through microbial fermentation, in which the butanol product is removed during the fermentation by extraction into a water-immiscible extractant composition. The invention further relates to compositions comprising a solution of butanol in a water immiscible organic extractant composition.

19 Claims, 13 Drawing Sheets

(56) References Cited

U.S. PATENT DOCUMENTS

| | | |
|---|---|---|
| 2011/0294179 A1 | 12/2011 | Grady et al. |
| 2011/0312044 A1 | 12/2011 | Anton et al. |
| 2011/0312053 A1 | 12/2011 | Burlew et al. |
| 2012/0156738 A1 | 6/2012 | Anton et al. |
| 2012/0208246 A1 | 8/2012 | Anton et al. |
| 2012/0323047 A1 | 12/2012 | Dauner et al. |
| 2013/0164795 A1 | 6/2013 | Lowe et al. |
| 2013/0217060 A1 | 8/2013 | Bramucci et al. |
| 2013/0224728 A1 | 8/2013 | Bramucci et al. |
| 2013/0252297 A1 | 9/2013 | Parten |
| 2013/0295661 A1 | 11/2013 | Roesch et al. |
| 2013/0309738 A1 | 11/2013 | Barr et al. |
| 2014/0018581 A1 | 1/2014 | Grady et al. |
| 2014/0024064 A1 | 1/2014 | Burlew et al. |
| 2014/0073021 A1 | 3/2014 | Bazzana et al. |
| 2014/0073820 A1 | 3/2014 | Bazzana et al. |
| 2014/0093931 A1 | 4/2014 | Dauner et al. |
| 2014/0094630 A1 | 4/2014 | Anton et al. |
| 2014/0099688 A1 | 4/2014 | Grady et al. |
| 2014/0106419 A1 | 4/2014 | Bazzana et al. |
| 2014/0142352 A1 | 5/2014 | Dauner et al. |
| 2014/0162344 A1 | 6/2014 | DiCosimo et al. |
| 2014/0178529 A1 | 6/2014 | Anton et al. |
| 2014/0234929 A1 | 8/2014 | Barr et al. |
| 2014/0256020 A1 | 9/2014 | DiCosimo et al. |
| 2014/0273127 A1 | 9/2014 | Fuchs et al. |
| 2014/0273130 A1 | 9/2014 | Anthony et al. |
| 2014/0303408 A1 | 10/2014 | Zaher et al. |
| 2014/0311889 A1 | 10/2014 | Zaher et al. |
| 2014/0363865 A1 | 12/2014 | Burlew et al. |
| 2015/0010975 A1 | 1/2015 | Burlew et al. |
| 2015/0010984 A1 | 1/2015 | Bhalla et al. |
| 2015/0060259 A1 | 3/2015 | Xu |
| 2015/0211026 A1 | 7/2015 | Bazzana et al. |
| 2015/0267225 A1 | 9/2015 | Bazzana et al. |

FOREIGN PATENT DOCUMENTS

| | | |
|---|---|---|
| JP | 61192291 | 8/1986 |
| JP | 62022593 | 1/1987 |
| WO | WO2008/143704 | 11/2008 |
| WO | WO2009/086391 | 7/2009 |
| WO | WO 2010/119339 | 10/2010 |

OTHER PUBLICATIONS

Bar, Effect of Interphase Mixing on a Water-Organic Solvent Two-Liquid Phase Microbial. System: Ethanol Fermentation, J. Chem. Tech. Biotechnol. 43:49-62, 1988.

Barba, et al., Hyperazeotropic Ethanol Salted-out by Extractive Distillation. Theoretical Evaluation and Experimenatl Check, Chem. Eng. Sci. 40:2287-2292, 1985.

Barros, et al., Integration of Enzyme Catalysis in an Extractive Fermentation Process, Biocatalysis in Organic Media, Proceedings of International Symposium, Wageningen, The Netherlands, 1986, pp. 185-196.

Bruce, et al., Solvent Selection Strategies for Extractive Biocatalysis, Biotechnol, Prog. 7:116-124, 1991.

Bruce, et al., Solvent Selection Strategies for Extractive Biocatalysis, Biotechnol. Prog. 7:116-124, 1991.

Buggert et al., Prediction of Equilibrum Partitioning of Nonpolar Organic Solutes in Water Surfactant Systems by UNIFAC and COSMO-RS Models, Chem. Eng. Technol, 29:567-573, 2006.

Carolan et al. The Effect of Additives and Impurities on the Partition of Ethanol into n-Decanol fom Aqueous Solutions, Dev. Chem. Eng. Mineral Process. 8:551-569, 2000.

Crabbe, et al., Biodiesel production from crude palm oil and evaluation of butanol extraction and fuel properties, Proc. Biochem. 37:65-71, 2001.

Daugulis, et al., Continuous Fermentation of High-Strength Glucose Feeds to Ethanol, Biotech. Lett. 16:637-642, 1994.

Daugulis, Integrated Fermentation and Recovery Process, Current Opin. Biotechnol. 5:192-195, 1994.

Davison, et al., Continuous Direct Solvent Extraction of Butanol in a Fermenting Fluidized-Bed Bioreactor with Immobilized Clostridium acetobutylicum, Appl. Biochem. Biotechnol. 39/40:415-426, 1993.

Eckert, et al., Continuous Acetone-Butanol Production with Direct Product Removal, Appl. Microbiol. Biotechnol. 27:221-228, 1987.

Eiteman, et al., in situ Extraction versus the Use of an External Column in Fermentation, Appl. Microbiol. Biotechnol. 30:614 618 1989.

Evans, et al., Enhancement of Butanol Formation by Clostridium acetobutylicurn in the Presence of Decanol-Oleyl Alcohol Mixed Extractants, Appl. Environ. Microbiol, 54:1662-1667, 1988.

Evans, et al., Response of Costdium aceobuylicum to the Presence of Mixed Extracants, Appl. Biochem. Biotechnol. 17:175-192, 1988.

Evans, et al. Effects of extractive fermentation on utyric acid production by Clostridium acetobutylicurn, Appl. Microbiol. Biotechnol. 32:393,397, 1990.

Ezeji, et al., Butanol Fermentation Research: Upstream and Downstream Manipulations, The Chemical Record 4:305-314, 2004.

Ezeji, et al., Bioproduction of butanol from biomass: from genes to bioreactors, Current Opin. Biotechnol. 18:220-227, 2007.

Ezeji, et al., Achievements and perspectives to overcome the poor solvent resistance in acetone and butanol-producing microorganisms, Appl. Microbiol, Biotechnol. 85:1697-1712, 2010.

Griffith, et al., 1-Butanol Extraction with Vegetable Oil, Fatty-Acid Esters, Developments in Industrial Microbiology, Chapter 76, 25:795-800, 1984.

Grobben, et al., Production of acetone, butanol and ethanol (ABE) from potato wastes: fermentation with integrated membrane extraction, Appl. Microbiol, Biotechnol. 39:494-498, 1993.

Groot, et al., Butanol Recovery from Fermentations by Liquid-Liquid Extraction and Mernbrance Solvent Extraction, Bioprocess Eng. 5:203-216, 1990.

Groot, et al., Technologies for Butanol Recovery Integrated with Fermentations, Process Biochem, 27:61-75, 1992.

Gyamerah, et al. Productionof Ethanol by Continuous Fermentation and Liquid-liquid Extraction, J. Chem. Tech. Biotechnol, 66:145-152, 1996.

Honda, et al., Ethanol Fermentation Associated with Solvent Extraction using Immobilized Growing Cells of Saccharomyces cerevisiae and its Lactose-Ferrnentatable Fusant, J. Chem. Eng. Japan 4:268-273, 1986.

Ishii, et al. Production of Butanol by Clostridium acetobutylicurn in Extractive Fermentation System, J. Chem. Eng. Japan 18:126-130, 1985.

Ishizaki, et al., Extractive Acetone-Butanol-Ethanol Fermentation Using Methylated Crude Palm Oil as Extractant in Batch Culture of Clostridium saccharoperbutylacetonicum N1-4 (ATCC 13564), J. Biosci. Bioeng. 87:352-356, 1999.

Jeon, et al., Membrane-Assisted Extractive Butanol Fermentation, Ann. N. Y. Acad. Sci. 506:536-542, 1987.

Jones, et al., Ethanol Production from Lactose by Extractive Fermentation, Biotechnol. Lett. 15:871-876, 1993.

Malinowski, Liquid-liquid and Vapour-liquid Behavior of Oleyl Aicohol Applied to Extractive Fermentation Processing, Can. J. Chem. Eng. 71:431-436, 1993.

Malinowski, et al., Salt Effects in Extraction of Ethanol, 1-Butanol and Acetone from Aqueous Solutions, AIChE J. 40:1459-1465, 1994.

Malinowski, Two-phase partitioning bioreactors in fermentation technology, Biotechnol. Adv. 19:525-538, 2001.

Matsumura et al., Applicaton of Solent Extaction to Ethanol Fermentation Appl. Microbiol. Biotechnol. 20:371-377, 1984.

Matsumura, et al., Energy saving effect of pervaporation using oieyi aicohol liquid membrane in butanol purification, Bioprocess Eng. 3:93-100; 1988.

Minier, et al., Ethanol Production by Extractive Fermentation, Biotechnol. Bioeng. 24:1565-1579, 1982.

Mitchell, et al., Ethanol from Dilute Aqueous Solution by Liquid-Liquid Extraction, Biotechnol. Bioeng, 30:348-351, 1987.

(56) References Cited

OTHER PUBLICATIONS

Munson, et al., Factors Influencing Solvent Selection for Extraction of Ethanol from Aqueous Solutions, Ind. Eng. Chem. Process Des. Dev. 23:115-121, 1984.

Offeman, et al., Extraction of Ethanol with Higher Carboxyiic Acids Solvents and their Toxicity to yeast, Sep. Purif. Technol. 72:180-185, 2010.

Oliviera, et al., Production and Extractive Biocatalysis of Ethanol Using Microencapsulated Yeast Cells and Lipase System, J. Chem. Technol. Biotechnol, 52:219-225, 1991.

Oliviera, et al., lmprovement of alcoholic fermentations by simultaneous extraction and enzymatic esterification of ethanol, J. Molecular Catalysis B: Enzymatic 5:29-33, 1998.

Oushoorn, et al., Assessment of Options for Selective 1-Butanol Recovery from Aqueous Solution, Ind. Eng. Chem. Res. 48:7325-7336, 2009.

Pfennig, et al., Influence of Electrolytes on Liquid-Liquid Extraction, Ind. Eng. Chem. Res, 37:3180-3188, 1988.

Qureshi, et al., Continuous Production of Acetone-Butanol-Ethanol Using Immobilized Cells of Clostridium acetobutylicurn and Integration with Product Removal by Liquid-Liquid Extraction, J. Ferment. Bioeng. 80:185-189, 1995.

Ramey, Production of Butyric Acid and Butanol from Biomass, Final Report, Dept. of Energy, Contract No. De-F-G02-00ER86106, 2004.

Roffler, Extractive Fermentation-Lactic Acid and Acetone/Butanol Production, Dissertation, Univ. of California, Berkeley, 1986.

Roffler, et al., Extractive Fermentation of Acetone and Butanol: Process Design arid Economic Evaivation, Biotechnol. Progress 3:131-140, 1987.

Roffler, et al., In-situ Recovery of Butanol during Fermentation, Bioprocess Eng. 2:1-12, 1987.

Roffler, et al., in situ Extractive Fermentation of Acetone and Butanol, Biotechnol. Bioeng. 31:135-143, 1988.

Roffler, et al., Extractive Bioconversions with Nonaqueous Solvents, Extractive Bioconversions, Marcel Dekker, Inc. N.Y., 1990, pp. 133-172.

Schugerl, Integrated Processing of Biotechnology Products, Biotechnol. Adv. 18:581-599, 2000.

Taya, et al., Monitoring and Control for Extractive Fermentation of Clostridium acetobutylicum, J. Ferment. technol. 63:181-187, 1985.

Vane, Separation Technologies for the Recovery and Dehydration of Alcohols from Fermentation Broths, Biofuels, Bioprod. Bioref. 2:553-588, 2008.

Wang, et al., Enhanced Alcohol Production Through On-Line Extraction, Third Symposium on Biotechnology in Energy Production and Conservation, Biotechnol. Bioeng. Symp. 11:555-565, 1981.

Wayman, et al., Production of Acetone-Butanol by Extractive Fermentation Using Dibutylphthalate as Extractant J. Ferment, Technol. 65:295-300, 1987.

Weilnhammer, et al., Continuous Fermentation with Product Recovery by in-situ Extraction, Chem. Eng. Technol. 17:365-373, 1994.

Barton, et al., Evaluation of solvents for extractive butanol, fermentation with Clostridium acetobutylicum and the use of poly-(propylene glycol) 1200, Appl. Microbiol. Biotechnol. 36:632-639, 1992.

Kraemer, et al., Separation of Butanoi from Acetone-Butanol-Ethanol Fermentation by a Hybrid Extraction-Distillation Process, Computers Chem. Eng. 35:949-963, 2011.

Tanaka, et al., Membrane-assisted Extractive Butanol Fermentation by Clostridium saccharoperbutylacetonicum N1-4 with 1-Dodecanol as the Extractant, Bioresource Technol. 116:448-452, 2012.

International Preliminary Report on Patentability for corresponding International Application No. PCT/US2014/029142, issued Sep. 15, 2015.

International Search Report for corresponding International Application No. PCT/US2014/029142, mailed Aug. 19, 2014.

\* cited by examiner

METHOD FOR PRODUCING BUTANOL USING EXTRACTIVE FERMENTATION

CROSS-REFERENCE

This application claims priority to U.S. Provisional Patent Application No. 61/788,213, filed on 15 Mar. 2013, entitled Method for Production of Butanol Using Extractive Fermentation, which is hereby incorporated by reference in its entirety. Additionally, this application incorporates by reference in their entireties U.S. Provisional Patent Application No. 61/790,828, filed on 15 Mar. 2013, entitled Method for Production of Butanol Using Extractive Fermentation and U.S. Provisional Patent Application No. 61/790,401, filed on 15 Mar. 2013, entitled Method for Production of Butanol Using Extractive Fermentation.

FIELD OF THE INVENTION

The invention relates to the field of biofuels. More specifically, the invention relates to a method for producing butanol through microbial fermentation, in which the butanol product is removed by extraction into a water immiscible organic extractant during the fermentation.

BACKGROUND OF THE INVENTION

Butanol is an important industrial chemical, with a variety of applications, such as use as a fuel additive, as a feedstock chemical in the plastics industry, and as a food grade extractant in the food and flavor industry. Each year 10 to 12 billion pounds of butanol are produced by petrochemical means and the need for this chemical will likely increase.

Several chemical synthetic methods are known; however, these methods of producing butanol use starting materials derived from petrochemicals and are generally expensive and are not environmentally friendly. Several methods of producing butanol by fermentation are also known, for example the ABE process which is the fermentive process producing a mixture of acetone, 1-butanol and ethanol. Acetone-butanol-ethanol (ABE) fermentation by *Clostridium acetobutylicum* is one of the oldest known industrial fermentations; as is also the pathways and genes responsible for the production of these solvents. Production of 1-butanol by the ABE process is limited by the toxic effect of the 1-butanol on *Clostridium acetobutylicum*. In situ extractive fermentation methods using specific organic extractants which are nontoxic to the bacterium have been reported to enhance the production of 1-butanol by fermentation using *Clostridium acetobutylicum* (Roffler et al., Biotechnol. Bioeng. 31:135-143, 1988; Roffler et al., Bioprocess Engineering 2:1-12, 1987; and Evans et al., Appl. Environ. Microbiol. 54:1662-1667, 1988).

In contrast to the native *Clostridium acetobutylicum* described above, recombinant microbial production hosts expressing 1-butanol, 2-butanol, and isobutanol biosynthetic pathways have also been described. These recombinant hosts have the potential of producing butanol in higher yields compared to the ABE process because they do not produce byproducts such as acetone and ethanol. With these recombinant hosts, the biological production of butanol appears to be limited by the butanol toxicity thresholds of the host microorganism used in the fermentation. U.S. Patent Application Publication Nos. 2009/0305370 and 2011/0097773, each of which is incorporated by reference herein in its entirety, disclose a method of making butanol from at least one fermentable carbon source that overcomes the issues of toxicity resulting in an increase in the effective titer, the effective rate, and the effective yield of butanol production by fermentation utilizing a recombinant microbial host wherein the butanol is extracted into specific organic extractants during fermentation.

Improved methods for producing and recovering butanol from a fermentation medium are continually sought. Lower cost processes and improvements to process operability are also desired. Identification of improved extractants for use with fermentation media, such as extractants exhibiting higher partition coefficients, lower viscosity, lower density, commercially useful boiling points, and sufficient microbial biocompatibility, is a continual need.

BRIEF SUMMARY OF THE INVENTION

Provided herein are methods for recovering butanol from a fermentation medium. The methods comprise (a) providing a fermentation medium comprising butanol, water, and a recombinant microorganism comprising a butanol biosynthetic pathway, wherein the recombinant microorganism produces butanol; (b) contacting the fermentation medium with a water immiscible organic extractant composition comprising a solvent selected from the group consisting of $C_{12}$ to $C_{22}$ fatty alcohols, $C_{12}$ to $C_{22}$ ethers, esters of $C_{12}$ to $C_{22}$ fatty acids, $C_{10}$ to $C_{22}$ alkanes, and mixtures thereof, to form a butanol-containing organic phase and an aqueous phase, wherein the solvent is biocompatible with the microorganism such that at least about 75% of the microorganisms are viable after exposure to the organic extractant composition, and wherein the solvent has a boiling point less than about 300° C., with the proviso that the organic extractant is not oleyl alcohol, 1-dodecanol, behenyl alcohol, cetyl alcohol, myristyl alcohol, or stearyl alcohol; and (c) recovering the butanol from the butanol-containing organic phase.

In some embodiments, the solvent is trimethylnonanol, methyl laurate, di-n-octyl ether, dodecane, n-undecane, ethyl decanoate, ethyl laurate, or mixtures thereof.

In certain embodiments, methods for recovering butanol from a fermentation medium comprise (a) providing a fermentation medium comprising butanol, water, and a recombinant microorganism comprising a butanol biosynthetic pathway, wherein the recombinant microorganism produces butanol; (b) contacting the fermentation medium with a water immiscible organic extractant composition comprising a solvent, wherein the solvent is trimethylnonanol, methyl laurate, di-n-octyl ether, dodecane, n-undecane, ethyl decanoate, ethyl laurate, or mixtures thereof, to form a butanol-containing organic phase and an aqueous phase; and (c) recovering the butanol from the butanol-containing organic phase.

In some embodiments, the contacting of the organic extractant composition with the fermentation medium occurs in the fermentor. In other embodiments, the contacting of the organic extractant composition with the fermentation medium occurs outside the fermentor. In some embodiments, the butanol is recovered after transferring a portion of the fermentation medium from the fermentor to a vessel, wherein the contacting of the organic extractant composition with the fermentation medium occurs in the vessel. In some embodiments, the butanol is isobutanol.

In certain embodiments, the organic extractant composition further comprises an additional solvent, wherein the second solvent is n-hexanol, methyl isobutyl carbinol, 2-ethyl-1-hexanol, 2,6-dimethylheptan-4-ol, or mixtures thereof. In other embodiments, the organic extractant composition further comprises 2,6-dimethylheptan-4-ol. In some embodiments, the additional solvent has a butanol partition coefficient greater than about 4, 4.5, 5, 5.5, 6, 6.5, 7, 7.5, or 8.

In some embodiments, the contacting of the organic extractant composition with the fermentation medium comprises contacting the fermentation medium via a co-current or counter-current stream of the organic extractant composition.

In some embodiments, the recovered butanol has an effective titer from about 20 g per liter to about 50 g per liter of the fermentation medium. In some embodiments, the recovered butanol has an effective titer from about 22 g per liter to about 50 g per liter. In some embodiments, the recovered butanol has an effective titer from about 25 g per liter to about 50 g per liter. In embodiments, the recovered butanol has an effective titer of at least 25 g, at least 30 g, at least 35 g, at least 37 g, at least 40 g, or at least 45 g per liter of the fermentation medium.

Also provided herein is a composition comprising butanol in a water immiscible organic extractant composition, wherein the organic extractant composition comprises a solvent selected from the group consisting of $C_{12}$ to $C_{22}$ fatty alcohols, $C_{12}$ to $C_{22}$ ethers, esters of $C_{12}$ to $C_{22}$ fatty acids, $C_{10}$ to $C_{22}$ alkanes, and mixtures thereof, wherein the solvent is biocompatible with a recombinant microorganism comprising a butanol biosynthetic pathway, wherein at least 75% of the recombinant microorganism is viable after exposure to the organic extractant composition, and wherein the solvent has a boiling point less than about 300° C., with the proviso that the solvent is not oleyl alcohol, 1-dodecanol, behenyl alcohol, cetyl alcohol, myristyl alcohol, or stearyl alcohol.

In certain embodiments, the boiling point of the solvent is less than about 275° C., less than about 250° C., less than about 225° C., or less than about 200° C.

In certain embodiments, provided herein is a composition, comprising a solution of butanol in a water immiscible organic extractant composition, wherein the organic extractant composition comprises a solvent, wherein the solvent is trimethylnonanol, methyl laurate, di-n-octyl ether, dodecane, n-undecane, ethyl decanoate, ethyl laurate, or mixtures thereof.

In other embodiments, the composition further comprises an additional solvent, wherein the second solvent is n-hexanol, methyl isobutyl carbinol, 2-ethyl-1-hexanol, 2,6-dimethylheptan-4-ol, or mixtures thereof. In other embodiments, the organic extractant composition further comprises 2,6-dimethylheptan-4-ol.

In some embodiments, the butanol in the composition is isobutanol.

BRIEF DESCRIPTION OF THE DRAWINGS/FIGURES

FIG. 1 schematically illustrates one embodiment of the methods of the invention, in which the first water immiscible extractant and the optional second water immiscible extractant are combined in a vessel prior to contacting the fermentation medium with the extractant in a fermentation vessel.

FIG. 2 schematically illustrates one embodiment of the methods of the invention, in which the first water immiscible extractant and the optional second water immiscible extractant are added separately to a fermentation vessel in which the fermentation medium is contacted with the extractant.

FIG. 3 schematically illustrates one embodiment of the methods of the invention, in which the first water immiscible extractant and the optional second water immiscible extractant are added separately to different fermentation vessels for contacting of the fermentation medium with the extractant.

FIG. 4 schematically illustrates one embodiment of the methods of the invention, in which extraction of the product occurs downstream of the fermentor and the first water immiscible extractant and the optional second water immiscible extractant are combined in a vessel prior to contacting the fermentation medium with the extractant in a different vessel.

FIG. 5 schematically illustrates one embodiment of the methods of the invention, in which extraction of the product occurs downstream of the fermentor and the first water immiscible extractant and the optional second water immiscible extractant are added separately to a vessel in which the fermentation medium is contacted with the extractant.

FIG. 6 schematically illustrates one embodiment of the methods of the invention, in which extraction of the product occurs downstream of the fermentor and the first water immiscible extractant and the optional second water immiscible extractant are added separately to different vessels for contacting of the fermentation medium with the extractant.

FIG. 7 schematically illustrates one embodiment of the methods of the invention, in which extraction of the product occurs in at least on batch fermentor via co-current flow of a water-immiscible extractant comprising a first solvent and an optional second solvent at or near the bottom of a fermentation mash to fill the fermentor with extractant which flows out of the fermentor at a point at or near the top of the fermentor.

Figure 14:
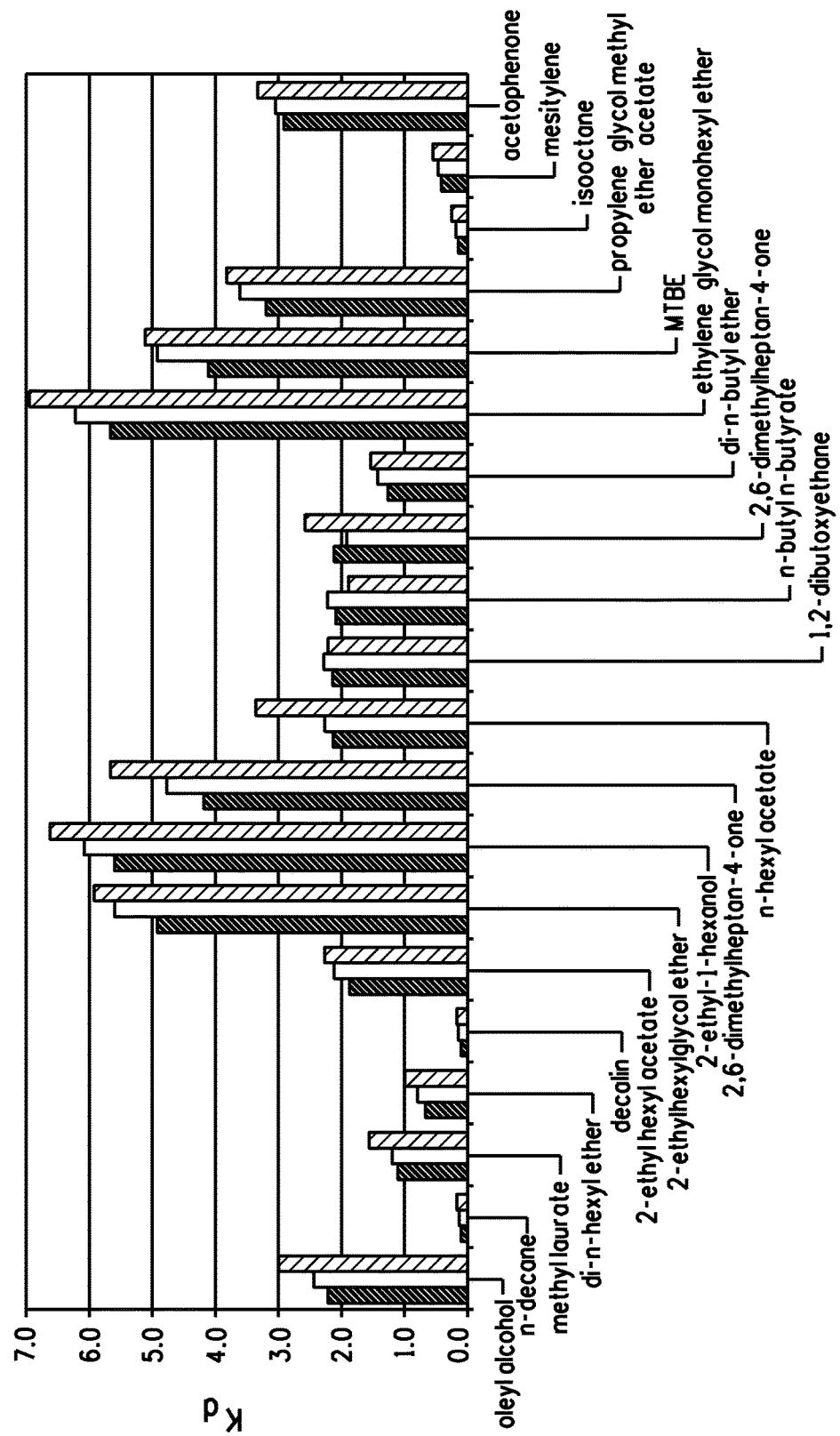

FIG. 14 illustrates the effect of different aqueous media on the solvent panel $K_d$ value (n=1 for minimal and rich media; n=3 for water). A solvent panel was used to extract 3% isobutanol prepared in water (left bar), minimal media (middle bar), and rich media (right bar). Media properties, like ionic strength, enhances organic phase extraction.

Figure 15:
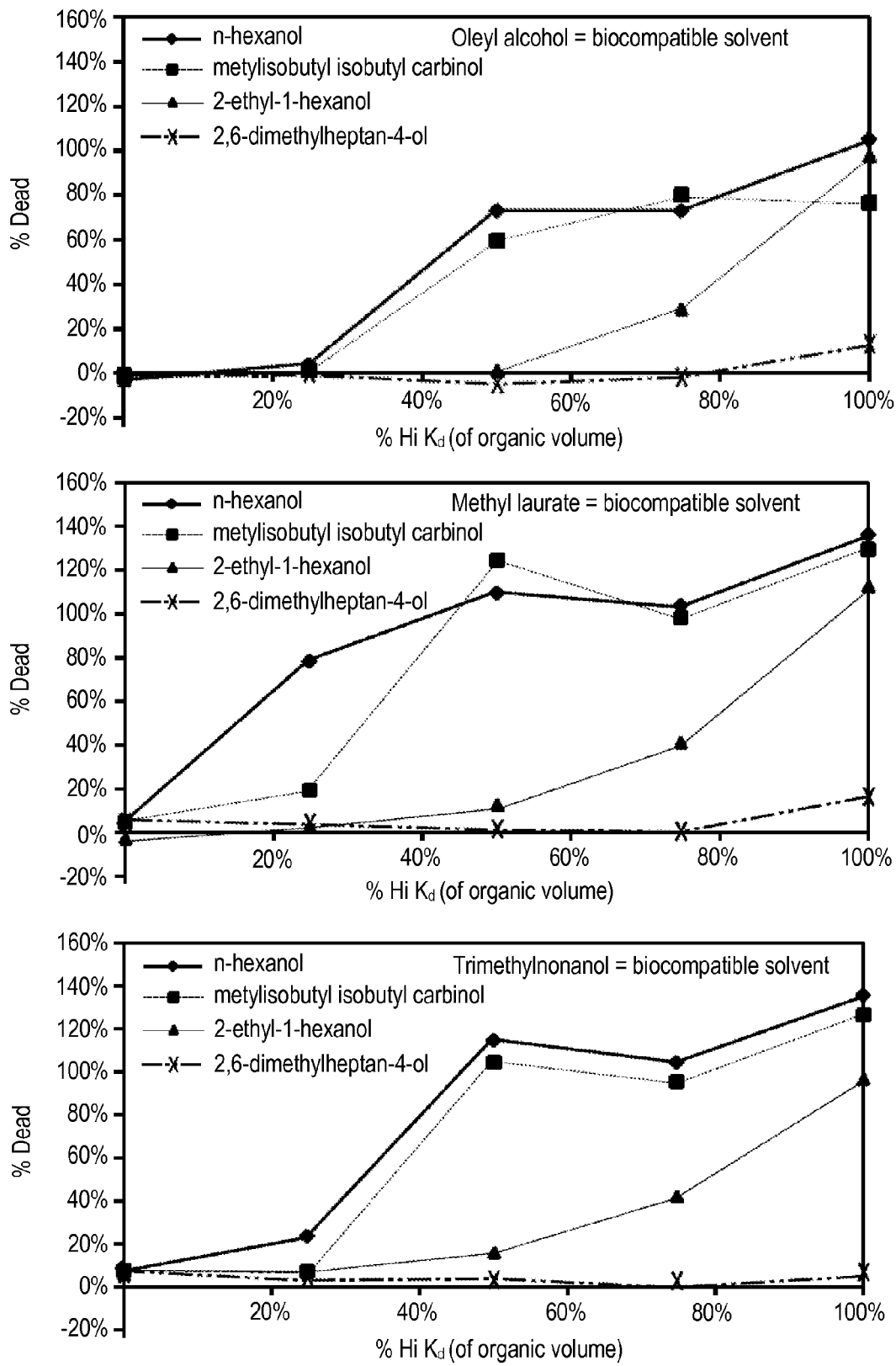

FIG. 15 illustrates the primary viability data for an isobutanologen exposed to mixtures using three biocompatible solvents, oleyl alcohol, methyl laurate, and trimethylnonanol, and four high $K_d$ solvents: n-hexanol, methyl isobutyl carbinol, 2-ethyl-1-hexanol, and 2,6-dimethylhepta-4-ol. The ordinate axis describes the level of mixture where 0% is defined as pure biocompatible solvent and 100% is defined as pure high $K_d$ solvent.

Figure 16:
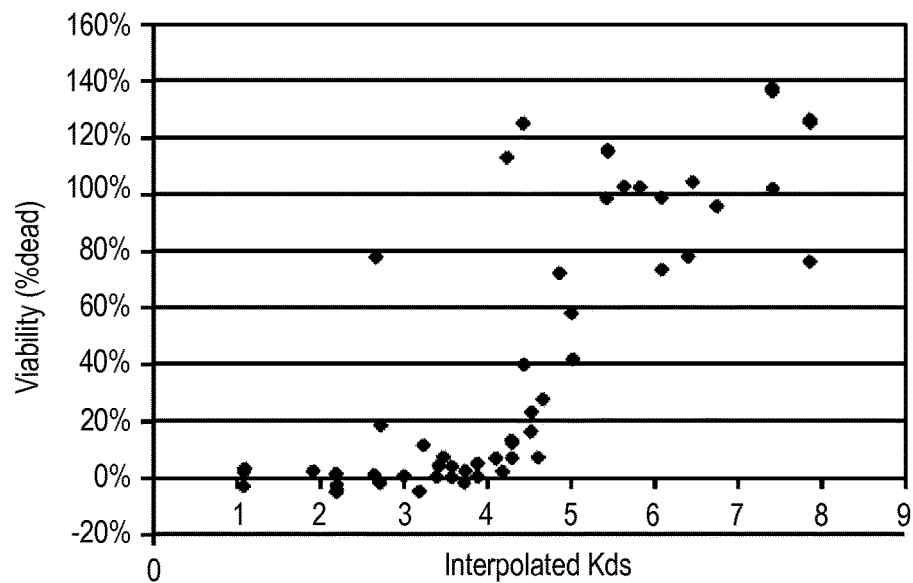

FIG. 16 is a scatter plot in which all primary viability data were plotted against interpolated $K_d$ of all mixtures studied with no regard to the chemical identity of the solvents.

Figure 17:
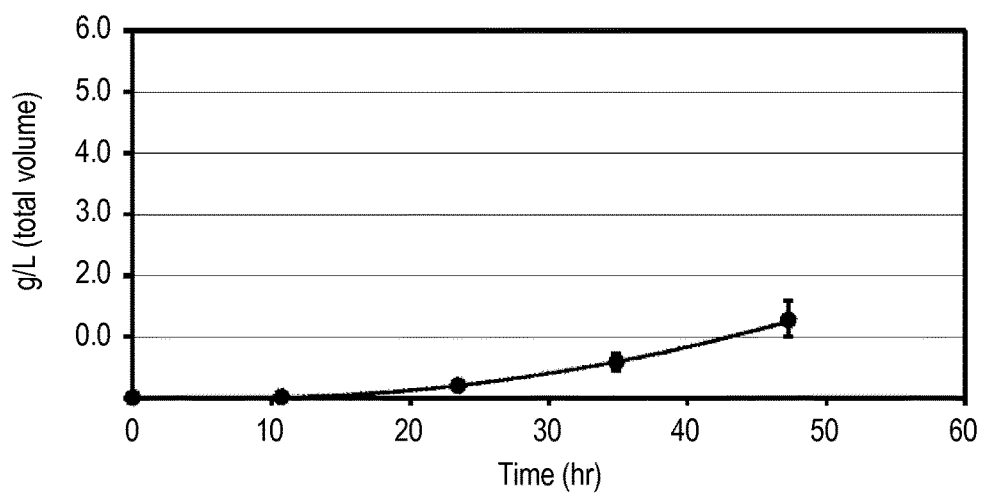

FIG. 17 illustrates the isobutanol production from an isobutanologen in a tertiary screen of 75% oleyl alcohol and 25% 2,6-dimethylheptan-4-ol.

Figure 18:
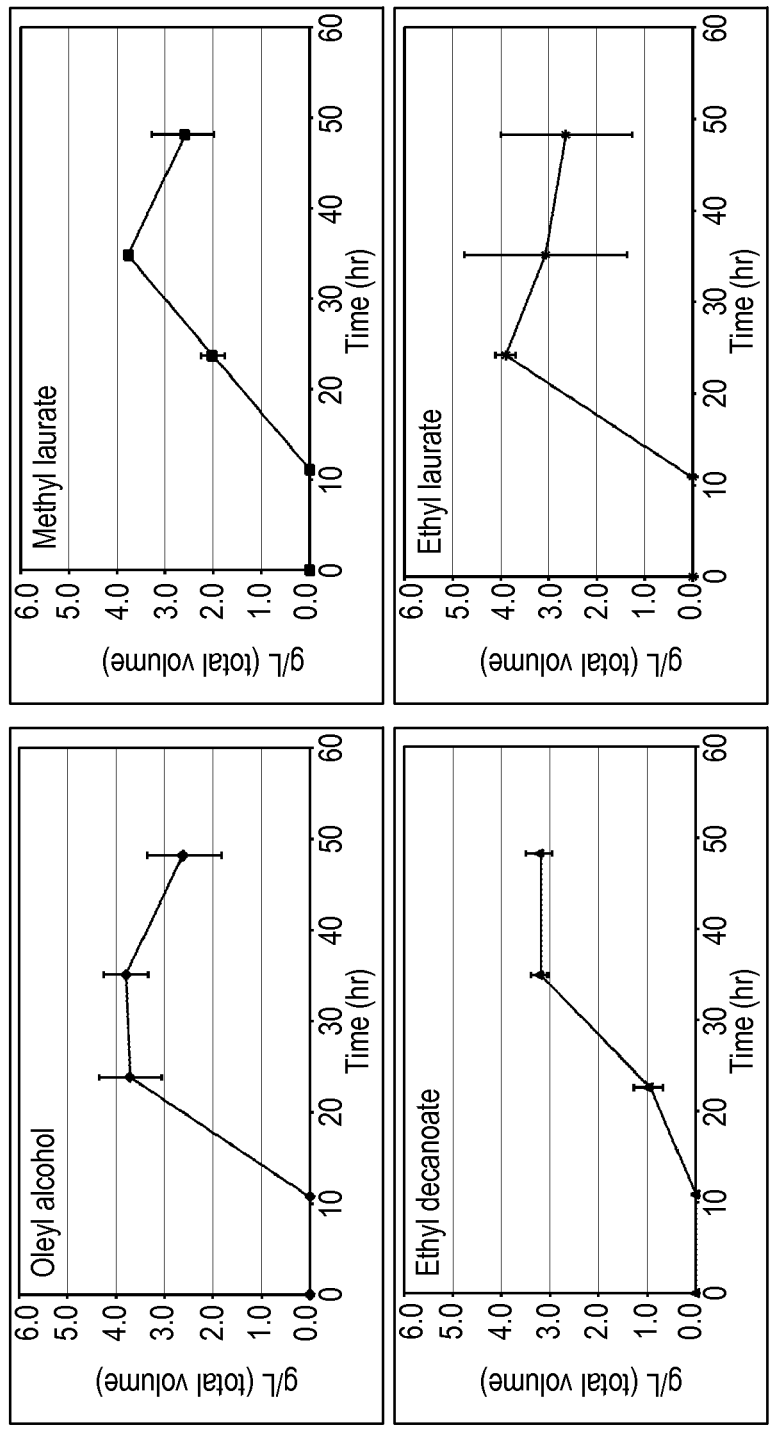

FIG. 18 illustrates the isobutanol production from an isobutanologen of biocompatible methyl laurate chemical structure analogs. Error bars denote 95% confidence intervals.

DETAILED DESCRIPTION OF THE INVENTION

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

In order to further define this invention, the following terms, abbreviations and definitions are provided.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. §2111.03.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the claims as presented or as later amended and supplemented, or in the specification.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, or within 5% of the reported numerical value.

The term "butanol biosynthetic pathway" as used herein refers to the enzymatic pathway to produce 1-butanol, 2-butanol, or isobutanol.

The term "1-butanol biosynthetic pathway" refers to an enzymatic pathway to produce 1-butanol. A "1-butanol biosynthetic pathway" can refer to an enzyme pathway to produce 1-butanol from acetyl-coenzyme A (acetyl-CoA). For example, 1-butanol biosynthetic pathways are disclosed in U.S. Patent Application Publication No. 2008/0182308 and International Publication No. WO 2007/041269, which are herein incorporated by reference in their entireties.

The term "2-butanol biosynthetic pathway" refers to an enzymatic pathway to produce 2-butanol. A "2-butnaol biosynthetic pathway" can refer to an enzyme pathway to produce 2-butanol from pyruvate. For example, 2-butanol biosynthetic pathways are disclosed in U.S. Pat. No. 8,206,970, U.S. Patent Application Publication No. 2007/0292927, International Publication Nos. WO 2007/130518 and WO 2007/130521, which are herein incorporated by reference in their entireties.

The term "isobutanol biosynthetic pathway" refers to an enzymatic pathway to produce isobutanol. An "isobutanol biosynthetic pathway" can refer to an enzyme pathway to produce isobutanol from pyruvate. For example, isobutanol biosynthetic pathways are disclosed in U.S. Pat. No. 7,851,188, U.S. Application Publication No. 2007/0092957, and International Publication No. WO 2007/050671, which are herein incorporated by reference in their entireties. From time to time "isobutanol biosynthetic pathway" is used synonymously with "isobutanol production pathway."

The term "butanol" as used herein refers to the butanol isomers 1-butanol (1-BuOH), 2-butanol (2-BuOH), tert-butanol (t-BuOH), and/or isobutanol (iBuOH or i-BuOH, also known as 2-methyl-1-propanol), either individually or as mixtures thereof. From time to time, as used herein the terms "biobutanol" and "bio-produced butanol" may be used synonymously with "butanol."

Uses for butanol can include, but are not limited to, fuels (e.g., biofuels), a fuel additive, an alcohol used for the production of esters that can be used as diesel or biodiesel fuel, as a chemical in the plastics industry, an ingredient in formulated products such as cosmetics, and a chemical intermediate. Butanol may also be used as a solvent for paints, coatings, varnishes, resins, gums, dyes, fats, waxes, resins, shellac, rubbers, and alkaloids.

As used herein, the term "bio-produced" means that the molecule (e.g., butanol) is produced from a renewable source (e.g., the molecule can be produced during a fermentation process from a renewable feedstock). Thus, for example, bio-produced isobutanol can be isobutanol produced by a fermentation process from a renewable feedstock. Molecules produced from a renewable source can further be defined by the $^{14}C/^{12}C$ isotope ratio. A $^{14}C/^{12}C$ isotope ratio in range of from 1:0 to greater than 0:1 indicates a bio-produced molecule, whereas a ratio of 0:1 indicates that the molecule is fossil derived.

"Product alcohol" as used herein, refers to any alcohol that can be produced by a microorganism in a fermentation process that utilizes biomass as a source of fermentable carbon substrate. Product alcohols include, but are not limited to, $C_1$ to $C_8$ alkyl alcohols, and mixtures thereof. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, pentanol, and mixtures thereof. Likewise $C_2$ to $C_8$ alkyl alcohols include, but are not limited to, ethanol, propanol, butanol, and pentanol. "Alcohol" is also used herein with reference to a product alcohol.

A recombinant host cell comprising an "engineered alcohol production pathway" (such as an engineered butanol or isobutanol production pathway) refers to a host cell containing a modified pathway that produces alcohol in a manner different than that normally present in the host cell. Such differences include production of an alcohol not typically produced by the host cell, or increased or more efficient production.

The term "heterologous biosynthetic pathway" as used herein refers to an enzyme pathway to produce a product in which at least one of the enzymes is not endogenous to the host cell containing the biosynthetic pathway.

The term "butanologen" as used herein refers to a microorganism capable of producing butanol. The term "isobutanologen" as used herein refers to a microorganism capable of producing isobutanol.

The term "ethanologen" as used herein refers to a microorganism capable of producing ethanol.

The term "extractant" as used herein refers to one or more organic solvents which can be used to extract a product alcohol. From time to time as used herein, the term "extractant" may be used synonymously with "solvent."

The term "effective isobutanol productivity" as used herein refers to the total amount in grams of isobutanol produced per gram of cells.

The term "effective titer" as used herein, refers to the total amount of a particular alcohol (e.g., butanol) produced by fermentation per liter of fermentation medium. The total amount of butanol includes: (i) the amount of butanol in the fermentation medium; (ii) the amount of butanol recovered from the organic extractant; and (iii) the amount of butanol recovered from the gas phase, if gas stripping is used.

The term "effective rate" as used herein, refers to the total amount of butanol produced by fermentation per liter of fermentation medium per hour of fermentation.

The term "effective yield" as used herein, refers to the amount of butanol produced per unit of fermentable carbon substrate consumed by the biocatalyst.

The term "separation" as used herein is synonymous with "recovery" and refers to removing a chemical compound from an initial mixture to obtain the compound in greater purity or at a higher concentration than the purity or concentration of the compound in the initial mixture.

The term "In Situ Product Removal" (ISPR) as used herein refers to the selective removal of a fermentation product from a biological process such as fermentation to control the product concentration as the product is produced.

The term "aqueous phase," as used herein, refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction, and the terms "solvent-poor phase" may be used synonymously with "aqueous phase" and "fermentation broth."

The term "organic phase," as used herein, refers to the non-aqueous phase of a biphasic mixture obtained by contacting a fermentation broth with a water-immiscible organic extractant. From time to time, as used herein the terms "solvent-rich phase" may be used synonymously with "organic phase."

The term "aqueous phase titer" as used herein, refers to the concentration of product alcohol (e.g., butanol) in the fermentation broth.

The term "water-immiscible" as used herein refers to a chemical component such as an extractant or a solvent, which is incapable of mixing with an aqueous solution such as a fermentation broth, in such a manner as to form one liquid phase.

The term "biphasic fermentation medium" as used herein refers to a two-phase growth medium comprising a fermentation medium (i.e., an aqueous phase) and a suitable amount of a water-immiscible organic extractant.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof. Non-limiting examples of carbon substrates are provided herein and include, but are not limited to, monosaccharides, disaccharides, oligosaccharides, polysaccharides, ethanol, lactate, succinate, glycerol, carbon dioxide, methanol, glucose, fructose, lactose, sucrose, xylose, arabinose, dextrose, cellulose, methane, amino acids, or mixtures thereof.

"Fermentation broth" as used herein means the mixture of water, sugars (fermentable carbon sources), dissolved solids (if present), microorganisms producing alcohol, product alcohol and all other constituents of the material in which product alcohol is being made by the reaction of sugars to alcohol, water and carbon dioxide ($CO_2$) by the microorganisms present. From time to time, as used herein the term "fermentation medium" and "fermented mixture" can be used synonymously with "fermentation broth."

As used herein a "fermentor" refers to any container, containers, or apparatus that are used to ferment a substrate. A fermentor can contain a fermentation medium and microorganism capable of fermentation. The term "fermentation vessel" refers to the vessel in which the fermentation reaction is carried out whereby alcohol such as butanol is made from sugars. "Fermentor" can be used herein interchangeable with "fermentation vessel."

The term "fermentation product" includes any desired product of interest, including, but not limited to 1-butanol, 2-butanol, isobutanol, etc.

The term "sugar" as used herein, refers to oligosaccharides, disaccharides, monosaccharides, and/or mixtures thereof. The term "saccharide" also includes carbohydrates including starches, dextrans, glycogens, cellulose, pentosans, as well as sugars.

The term "fermentable sugar" as used herein, refers to one or more sugars capable of being metabolized by the microorganisms disclosed herein for the production of fermentative alcohol.

The term "undissolved solids" as used herein, means non-fermentable portions of feedstock, for example, germ, fiber, and gluten. For example, the non-fermentable portions of feedstock include the portion of feedstock that remains as solids and can absorb liquid from the fermentation broth.

"Biomass" as used herein refers to a natural product containing a hydrolysable starch that provides a fermentable sugar, including any cellulosic or lignocellulosic material and materials comprising cellulose, and optionally further comprising hemicellulose, lignin, starch, oligosaccharides, disaccharides, and/or monosaccharides. Biomass can also comprise additional components, such as protein and/or lipids. Biomass can be derived from a single source, or biomass can comprise a mixture derived from more than one source. For example, biomass can comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood, and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

"Feedstock" as used herein means a product containing a fermentable carbon source. Suitable feedstock include, but are not limited to, rye, wheat, corn, corn mash, cane, cane mash, sugar cane, barley, cellulosic material, lignocellulosic material, and mixtures thereof.

The term "aerobic conditions" as used herein means growth conditions in the presence of oxygen.

The term "microaerobic conditions" as used herein means growth conditions with low levels of oxygen (i.e., below normal atmospheric oxygen levels).

The term "anaerobic conditions" as used herein means growth conditions in the absence of oxygen.

The term "minimal media" as used herein refers to growth media that contain the minimum nutrients possible for growth, generally without the presence of amino acids. A minimal medium typically contains a fermentable carbon source and various salts, which may vary among microorganisms and growing conditions; these salts generally provide essential elements such as magnesium, nitrogen, phosphorous, and sulfur to allow the microorganism to synthesize proteins and nucleic acids.

The term "defined media" as used herein refers to growth media that have known quantities of all ingredients, e.g., a defined carbon source and nitrogen source, and trace elements and vitamins required by the microorganism.

The term "biocompatibility" as used herein refers to the measure of the ability of a microorganism to utilize glucose in the presence of an extractant. A biocompatible extractant permits the microorganism to utilize glucose. A non-biocompatible (i.e., a biotoxic) extractant does not permit the microorganism to utilize glucose, for example, at a rate greater than about 25% of the rate when the extractant is not present.

The term "toxicity" of solvent as used herein refers to the percentage of butanol-producing microorganisms killed after exposure to the solvent for a prolonged time, for example 24 hours.

The term "fatty acid" as used herein, refers to a carboxylic acid (e.g., aliphatic monocarboxylic acid) having $C_4$ to $C_{28}$ carbon atoms (most commonly $C_{12}$ to $C_{24}$ carbon atoms), which is either saturated or unsaturated. Fatty acids may also be branched or unbranched. Fatty acids may be derived from, or contained in esterified form, in an animal or vegetable fat, oil, or wax. Fatty acids may occur naturally in the form of glycerides in fats and fatty oils or may be obtained by hydrolysis of fats or by synthesis. The term fatty acid may describe a single chemical species or a mixture of fatty acids. In addition, the term fatty acid also encompasses free fatty acids.

The term "fatty alcohol" as used herein, refers to an alcohol having an aliphatic chain of $C_4$ to $C_{22}$ carbon atoms, which is either saturated or unsaturated.

The term "fatty aldehyde" as used herein, refers to an aldehyde having an aliphatic chain of $C_4$ to $C_{22}$ carbon atoms, which is either saturated or unsaturated.

The term "fatty amide" as used herein, refers to an amide having a long, aliphatic chain of $C_4$ to $C_{22}$ carbon atoms, which is either saturated or unsaturated.

The term "fatty ester" as used herein, refers to an ester having a long aliphatic chain of $C_4$ to $C_{22}$ carbon atoms, which is either saturated or unsaturated.

The term "carboxylic acid" as used herein, refers to any organic compound with the general chemical formula —COOH in which a carbon atom is bonded to an oxygen atom by a double bond to make a carbonyl group (—C=O) and to a hydroxyl group (—OH) by a single bond. A carboxylic acid may be in the form of the protonated carboxylic acid, in the form of a salt of a carboxylic acid (e.g., an ammonium, sodium, or potassium salt), or as a mixture of protonated carboxylic acid and salt of a carboxylic acid. The term carboxylic acid may describe a single chemical species (e.g., oleic acid) or a mixture of carboxylic acids as can be produced, for example, by the hydrolysis of biomass-derived fatty acid esters or triglycerides, diglycerides, monoglycerides, and phospholipids.

The term "alkane" as used herein refers to a saturated hydrocarbon.

"Portion" as used herein, includes a part of a whole or the whole. For example, a portion of fermentation broth includes a part of the fermentation broth as well as the whole (or all) the fermentation broth.

"Partition coefficient" or "$K_d$" refers to the ratio of the concentration of a compound in the two phases of a mixture of two immiscible solvents at equilibrium. A partition coefficient is a measure of the differential solubility of a compound between two immiscible solvents. Partition coefficient, as used herein, is synonymous with the term distribution coefficient.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene can comprise regulatory sequences and coding sequences that are derived from different sources, or regulatory sequences and coding sequences derived from the same source, but arranged in a manner different than that found in nature. "Endogenous gene" refers to a native gene in its natural location in the genome of a microorganism. A "foreign" gene refers to a gene not normally found in the host microorganism, but that is introduced into the host microorganism by gene transfer. Foreign genes can comprise native genes inserted into a non-native microorganism, or chimeric genes. A "transgene" is a gene that has been introduced into the genome by a transformation procedure.

As used herein, "native" refers to the form of a polynucleotide, gene, or polypeptide as found in nature with its own regulatory sequences, if present.

As used herein the term "coding sequence" or "coding region" refers to a DNA sequence that encodes for a specific amino acid sequence.

As used herein, "endogenous" refers to the native form of a polynucleotide, gene or polypeptide in its natural location in the organism or in the genome of an organism. "Endogenous polynucleotide" includes a native polynucleotide in its natural location in the genome of an organism. "Endogenous gene" includes a native gene in its natural location in the genome of an organism. "Endogenous polypeptide" includes a native polypeptide in its natural location in the organism transcribed and translated from a native polynucleotide or gene in its natural location in the genome of an organism.

The term "heterologous" when used in reference to a polynucleotide, a gene, or a polypeptide refers to a polynucleotide, gene, or polypeptide not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene can be introduced into the host organism by, e.g., gene transfer. A heterologous gene can include a native coding region with non-native regulatory regions that is reintroduced into the native host. For example, a heterologous gene can include a native coding region that is a portion of a chimeric gene including non-native regulatory regions that is reintroduced into the native host. "Heterologous polypeptide" includes a native polypeptide that is reintroduced into the source organism in a form that is different from the corresponding native polypeptide. A "heterologous" polypeptide or polynucleotide can also include an engineered polypeptide or polynucleotide that comprises a difference from the "native" polypeptide or polynucleotide, e.g., a point mutation within the endogenous polynucleotide can result in the production of a "heterologous" polypeptide. As used herein a "chimeric gene," a "foreign gene," and a "transgene," can all be examples of "heterologous" genes.

A "transgene" is a gene that has been introduced into the genome by a transformation procedure.

Microorganisms

Microbial hosts for butanol production can be selected from bacteria, cyanobacteria, filamentous fungi and yeasts. The microbial host used should be tolerant to the butanol product produced, so that the yield is not limited by toxicity of the product to the host. The selection of a microbial host for butanol production is described in detail below.

Microbes that are metabolically active at high titer levels of butanol are not well known in the art. Although butanol-tolerant mutants have been isolated from solventogenic Clostridia, little information is available concerning the butanol tolerance of other potentially useful bacterial strains. Most of the studies on the comparison of alcohol tolerance in bacteria suggest that butanol is more toxic than ethanol (de Cavalho et al., Microsc. Res. Tech. 64:215-22 (2004) and Kabelitz et al., FEMS Microbiol. Lett. 220:223-227 (2003)). Tomas et al. (J. Bacteriol. 186:2006-2018 (2004)) report that the yield of 1-butanol during fermentation in Clostridium acetobutylicum can be limited by butanol toxicity. The primary effect of 1-butanol on Clostridium acetobutylicum is disruption of membrane functions (Hermann et al., Appl. Environ. Microbiol. 50:1238-1243 (1985)).

The microbial hosts selected for the production of butanol should be tolerant to butanol and should be able to convert carbohydrates to butanol using the introduced biosynthetic pathway as described below. The criteria for selection of suitable microbial hosts include the following: intrinsic tolerance to butanol, high rate of carbohydrate utilization, availability of genetic tools for gene manipulation, and the ability to generate stable chromosomal alterations.

Suitable host strains with a tolerance for butanol can be identified by screening based on the intrinsic tolerance of the strain. The intrinsic tolerance of microbes to butanol can be measured by determining the concentration of butanol that is responsible for 50% inhibition of the growth rate (IC50) when grown in a minimal medium. The IC50 values can be determined using methods known in the art. For example, the microbes of interest can be grown in the presence of various amounts of butanol and the growth rate monitored by measuring the optical density at 600 nanometers. The doubling time can be calculated from the logarithmic part of the growth curve and used as a measure of the growth rate. The concentration of butanol that produces 50% inhibition of growth can be determined from a graph of the percent inhibition of growth versus the butanol concentration. In one embodiment, the host strain has an IC50 for butanol of greater than about 0.5%. In another embodiment, the host strain has an IC50 for butanol that is greater than about 1.5%. In yet another embodiment, the host strain has an IC50 for butanol that is greater than about 2.5%.

The microbial host for butanol production should also utilize glucose and/or other carbohydrates at a high rate. Most microbes are capable of utilizing carbohydrates. However, certain environmental microbes cannot efficiently use carbohydrates, and therefore would not be suitable hosts.

The ability to genetically modify the host is essential for the production of any recombinant microorganism. Modes of gene transfer technology that can be used include, for example, electroporation, conjugation, transduction or natural transformation. A broad range of host conjugative plasmids and drug resistance markers are available. The cloning vectors used with an organism are tailored to the host organism based on the nature of antibiotic resistance markers that can function in that host.

The microbial host also can be manipulated in order to inactivate competing pathways for carbon flow by inactivating various genes. This requires the availability of either transposons or chromosomal integration vectors to direct inactivation. Additionally, production hosts that are amenable to chemical mutagenesis can undergo improvements in intrinsic butanol tolerance through chemical mutagenesis and mutant screening.

Based on the criteria described above, suitable microbial hosts for the production of butanol include, but are not limited to, members of the genera, Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Pichia, Candida, Hansenula and Saccharomyces. In some embodiments, the host can be: Escherichia coli, Alcaligenes eutrophus, Bacillus licheniformis, Paenibacillus macerans, Rhodococcus erythropolis,

*Pseudomonas putida, Lactobacillus plantarum, Enterococcus faecium, Enterococcus gallinarium, Enterococcus faecalis, Pediococcus pentosaceus, Pediococcus acidilactici, Bacillus subtilis* or *Saccharomyces cerevisiae*.

Recombinant Microorganisms

While not wishing to be bound by theory, it is believed that the processes described herein are useful in conjunction with any alcohol producing microorganism, particularly recombinant microorganisms which produce alcohol.

Recombinant microorganisms which produce alcohol are also known in the art (e.g., Ohta et al., *Appl. Environ. Microbiol.* 57:893-900 (1991); Underwood et al., *Appl. Envrion. Microbiol.* 68:1071-81 (2002); Shen and Liao, *Metab. Eng.* 10:312-20 (2008); Hahnai et al., *Appl. Environ.* 73:7814-8 (2007); U.S. Pat. Nos. 5,514,583; 5,712,133; International Publication No. WO 1995/028476; Feldmann et al., *Appl. Microbiol. Biotechnol.* 38:354-61 (1992); Zhang et al., *Science* 267:240-3 (1995); U.S. Patent Publication No. 2007/0031918A1; U.S. Pat. Nos. 7,223,575; 7,741,119; U.S. Patent Publication No. 2009/0203099A1; U.S. Patent Publication No. 2009/0246846A1; and International Publication No. WO 2010/075241, which are herein incorporated by reference).

For example, the metabolic pathways of microorganisms may be genetically modified to produce butanol. These pathways may also be modified to reduce or eliminate undesired metabolites, and thereby improve yield of the product alcohol. The production of butanol by a microorganism is disclosed, for example, in U.S. Pat. Nos. 7,851,188; 7,993,889; 8,178,328, 8,206,970; U.S. Patent Application Publication Nos. 2007/0292927; 2008/0182308; 2008/0274525; 2009/0305363; 2009/0305370; 2011/0250610; 2011/0313206; 2011/0111472; 2012/0258873; and U.S. patent application Ser. No. 13/428,585, the entire contents of each are herein incorporated by reference. In some embodiments, microorganisms comprise a butanol biosynthetic pathway or a biosynthetic pathway for a butanol isomer such as 1-butanol, 2-butanol, or isobutanol. In some embodiments, the biosynthetic pathway converts pyruvate to a fermentative product. In some embodiments, the biosynthetic pathway converts pyruvate as well as amino acids to a fermentative product. In some embodiments, at least one, at least two, at least three, or at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism.

In some embodiments, the microorganism may be bacteria, cyanobacteria, filamentous fungi, or yeasts. Suitable microorganisms capable of producing product alcohol (e.g., butanol) via a biosynthetic pathway include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon, Yamadazyma*, or *Saccharomyces*. In one embodiment, recombinant microorganisms may be selected from the group consisting of *Escherichia coli, Alcaligenes eutrophus, Bacillus licheniformis, Paenibacillus macerans, Rhodocuccus erythropolis, Pseudomonas putida, Lactobacillus plantarum, Enterococcus faecium, Enterococcus gallinarium, Enterococcus faecalis, Bacillus subtilis, Candida sonorensis, Candida methanosorbosa, Kluyveromyces lactis, Kluyveromyces marxianus, Kluveromyces thermotolerans, Issatchenkia orientalis, Debaryomyces hansenii*, and *Saccharomyces cerevisiae*. In one embodiment, the genetically modified microorganism is yeast. In one embodiment, the genetically modified microorganism is a crabtree-positive yeast selected from *Saccharomyces, Zygosaccharomyces, Schizosaccharomyces, Dekkera, Torulopsis, Brettanomyces*, and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Saccharomyces uvarum, Saccharomyces castelli, Zygosaccharomyces rouxii, Zygosaccharomyces bailli*, and *Candida glabrata*.

In some embodiments, the host cell is *Saccharomyces cerevisiae*. *Saccharomyces cerevisiae* are known in the art and are available from a variety of sources including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

In some embodiments, the microorganism may be immobilized or encapsulated. For example, the microorganism may be immobilized or encapsulated using alginate, calcium alginate, or polyacrylamide gels, or through the induction of biofilm formation onto a variety of high surface area support matrices such as diatomite, celite, diatomaceous earth, silica gels, plastics, or resins. In some embodiments, ISPR may be used in combination with immobilized or encapsulated microorganisms. This combination may improve productivity such as specific volumetric productivity, metabolic rate, product alcohol yields, tolerance to product alcohol. In addition, immobilization and encapsulation may minimize the effects of the process conditions such as shearing on the microorganisms.

Biosynthetic pathways for the production of isobutanol that may be used include those as described by Donaldson et al. in U.S. Pat. Nos. 7,851,188; 7,993,388; and International Publication No. WO 2007/050671, which are incorporated herein by reference. In one embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by acetohydroxy acid reductoisomerase;

c) the 2,3-dihydroxyisovalerate from step b) to α-ketoisovalerate, which may be catalyzed, for example, by acetohydroxy acid dehydratase;

d) the α-ketoisovalerate from step c) to isobutyraldehyde, which may be catalyzed, for example, by a branched-chain α-keto acid decarboxylase; and, e) the isobutyraldehyde from step d) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by ketol-acid reductoisomerase;

c) the 2,3-dihydroxyisovalerate from step b) to α-ketoisovalerate, which may be catalyzed, for example, by dihydroxyacid dehydratase;

d) the α-ketoisovalerate from step c) to valine, which may be catalyzed, for example, by transaminase or valine dehydrogenase;

e) the valine from step d) to isobutylamine, which may be catalyzed, for example, by valine decarboxylase;

f) the isobutylamine from step e) to isobutyraldehyde, which may be catalyzed by, for example, omega transaminase; and, g) the isobutyraldehyde from step f) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by acetohydroxy acid reductoisomerase;

c) the 2,3-dihydroxyisovalerate from step b) to α-ketoisovalerate, which may be catalyzed, for example, by acetohydroxy acid dehydratase;

d) the α-ketoisovalerate from step c) to isobutyryl-CoA, which may be catalyzed, for example, by branched-chain keto acid dehydrogenase;

e) the isobutyryl-CoA from step d) to isobutyraldehyde, which may be catalyzed, for example, by acylating aldehyde dehydrogenase; and, f) the isobutyraldehyde from step e) to isobutanol, which may be catalyzed, for example, by a branched-chain alcohol dehydrogenase.

Biosynthetic pathways for the production of 1-butanol that may be used include those described in U.S. Patent Application Publication No. 2008/0182308 and WO2007/041269, which are incorporated herein by reference. In one embodiment, the 1-butanol biosynthetic pathway comprises the following substrate to product conversions:

a) acetyl-CoA to acetoacetyl-CoA, which may be catalyzed, for example, by acetyl-CoA acetyltransferase;

b) the acetoacetyl-CoA from step a) to 3-hydroxybutyryl-CoA, which may be catalyzed, for example, by 3-hydroxybutyryl-CoA dehydrogenase;

c) the 3-hydroxybutyryl-CoA from step b) to crotonyl-CoA, which may be catalyzed, for example, by crotonase;

d) the crotonyl-CoA from step c) to butyryl-CoA, which may be catalyzed, for example, by butyryl-CoA dehydrogenase;

e) the butyryl-CoA from step d) to butyraldehyde, which may be catalyzed, for example, by butyraldehyde dehydrogenase; and, f) the butyraldehyde from step e) to 1-butanol, which may be catalyzed, for example, by butanol dehydrogenase.

Biosynthetic pathways for the production of 2-butanol that may be used include those described by Donaldson et al. in U.S. Pat. No. 8,206,970; U.S. Patent Application Publication Nos. 2007/0292927 and 2009/0155870; International Publication Nos. WO 2007/130518 and WO 2007/130521, all of which are incorporated herein by reference. In one embodiment, the 2-butanol biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin from step b) to 3-amino-2-butanol, which may be catalyzed, for example, acetonin aminase;

d) the 3-amino-2-butanol from step c) to 3-amino-2-butanol phosphate, which may be catalyzed, for example, by aminobutanol kinase;

e) the 3-amino-2-butanol phosphate from step d) to 2-butanone, which may be catalyzed, for example, by aminobutanol phosphate phosphorylase; and, f) the 2-butanone from step e) to 2-butanol, which may be catalyzed, for example, by butanol dehydrogenase.

In another embodiment, the 2-butanol biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin to 2,3-butanediol from step b), which may be catalyzed, for example, by butanediol dehydrogenase;

d) the 2,3-butanediol from step c) to 2-butanone, which may be catalyzed, for example, by dial dehydratase; and, e) the 2-butanone from step d) to 2-butanol, which may be catalyzed, for example, by butanol dehydrogenase.

Biosynthetic pathways for the production of 2-butanone that may be used include those described in U.S. Pat. No. 8,206,970 and U.S. Patent Application Publication Nos. 2007/0292927 and 2009/0155870, which are incorporated herein by reference. In one embodiment, the 2-butanone biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin from step b) to 3-amino-2-butanol, which may be catalyzed, for example, acetonin aminase;

d) the 3-amino-2-butanol from step c) to 3-amino-2-butanol phosphate, which may be catalyzed, for example, by aminobutanol kinase; and, e) the 3-amino-2-butanol phosphate from step d) to 2-butanone, which may be catalyzed, for example, by aminobutanol phosphate phosphorylase.

In another embodiment, the 2-butanone biosynthetic pathway comprises the following substrate to product conversions:

a) pyruvate to alpha-acetolactate, which may be catalyzed, for example, by acetolactate synthase;

b) the alpha-acetolactate from step a) to acetoin which may be catalyzed, for example, by acetolactate decarboxylase;

c) the acetoin from step b) to 2,3-butanediol, which may be catalyzed, for example, by butanediol dehydrogenase;

d) the 2,3-butanediol from step c) to 2-butanone, which may be catalyzed, for example, by diol dehydratase.

The terms "acetohydroxyacid synthase," "acetolactate synthase," and "acetolactate synthetase" (abbreviated "ALS") are used interchangeably herein to refer to an enzyme that catalyzes the conversion of pyruvate to acetolactate and $CO_2$. Example acetolactate synthases are known by the EC number 2.2.1.6 (Enzyme Nomenclature 1992, Academic Press, San Diego). These enzymes are available from a number of sources, including, but not limited to, *Bacillus subtilis* (GenBank Nos: CAB07802.1, Z99122, NCBI (National Center for Biotechnology Information) amino acid sequence, NCBI nucleotide sequence, respectively), CAB15618, *Klebsiella pneumoniae* (GenBank Nos: AAA25079, M73842), and *Lactococcus lactis* (GenBank Nos: AAA25161, L16975)

The term "ketol-acid reductoisomerase" ("KARI"), "acetohydroxy acid isomeroreductase," and "acetohydroxy acid reductoisomerase" will be used interchangeably and refer to enzymes capable of catalyzing the reaction of (S)-acetolactate to 2,3-dihydroxyisovalerate. Example KARI enzymes may be classified as EC number EC 1.1.1.86 (Enzyme Nomenclature 1992, Academic Press, San Diego), and are available from a vast array of microorganisms, including, but not limited to, *Escherichia coli* (GenBank Nos: NP_418222, NC_000913), *Saccharomyces cerevisiae* (GenBank Nos: NP_013459, NC_001144), *Methanococcus maripaludis* (GenBank Nos: CAF30210, BX957220), *Bacillus subtilis* (GenBank Nos: CAB14789, Z99118), and *Anaerostipes caccae*. Ketol-acid reductoisomerase (KARI) enzymes are described in U.S. Pat. Nos. 7,910,342 and 8,129,162; U.S. Patent Application Publication Nos. 2008/0261230, 2009/0163376, 2010/0197519, PCT Application Publication No. WO/2011/041415, PCT Application Publication No. WO2012/129555; and U.S. Provisional Application No. 61/705,977, filed on Sep. 26, 2012, all of which are incorporated herein by reference. Examples of KARIs disclosed therein are those from *Lactococcus lactis, Vibrio cholera, Pseudomonas aeruginosa* PAO1, and *Pseudomonas fluorescens* PF5 mutants. In some embodiments, the KARI utilizes NADH. In some embodiments, the KARI utilizes NADPH. In some embodiments, the KARI utilizes NADH or NADPH.

The term "acetohydroxy acid dehydratase" and "dihydroxyacid dehydratase" ("DHAD") refers to an enzyme that catalyzes the conversion of 2,3-dihydroxyisovalerate to α-ketoisovalerate. Example acetohydroxy acid dehydratases are known by the EC number 4.2.1.9. Such enzymes are available from a vast array of microorganisms, including, but not limited to, *E. coli* (GenBank Nos: YP_026248, NC000913), *Saccharomyces cerevisiae* (GenBank Nos: NP_012550, NC_001142), *M. maripaludis* (GenBank Nos: CAF29874, BX957219), *B. subtilis* (GenBank Nos: CAB14105, Z99115), *L. lactis*, and *N. crassa*. U.S. Patent Application Publication No. 2010/0081154, U.S. Pat. Nos. 7,851,188, and 8,241,878, which are incorporated herein by reference in their entireties, describe dihydroxyacid dehydratases (DHADs), including a DHAD from *Streptococcus mutans* and variants thereof The term "branched-chain α-keto acid decarboxylase," "α-ketoacid decarboxylase," "α-ketoisovalerate decarboxylase," or "2-ketoisovalerate decarboxylase" ("KIVD") refers to an enzyme that catalyzes the conversion of α-ketoisovalerate to isobutyraldehyde and $CO_2$. Example branched-chain α-keto acid decarboxylases are known by the EC number 4.1.1.72 and are available from a number of sources, including, but not limited to, *Lactococcus lactis* (GenBank Nos: AAS49166, AY548760; CAG34226, AJ746364), *Salmonella typhimurium* (GenBank Nos: NP_461346, NC_003197), *Clostridium acetobutylicum* (GenBank Nos: NP_149189, NC_001988), *M. caseolyticus*, and *L. grayi*.

The term "branched-chain alcohol dehydrogenase" ("ADH") refers to an enzyme that catalyzes the conversion of isobutyraldehyde to isobutanol. Example branched-chain alcohol dehydrogenases are known by the EC number 1.1.1.265, but may also be classified under other alcohol dehydrogenases (specifically, EC 1.1.1.1 or 1.1.1.2). Alcohol dehydrogenases may be NADPH dependent or NADH dependent. Such enzymes are available from a number of sources, including, but not limited to, *S. cerevisiae* (GenBank Nos: NP_010656, NC_001136, NP_014051, NC_001145), *E. coli* (GenBank Nos: NP_417484, NC_000913), *C. acetobutylicum* (GenBank Nos: NP_349892, NC_003030; NP_349891, NC_003030). U.S. Patent Application Publication No. 2009/0269823 describes SadB, an alcohol dehydrogenase (ADH) from *Achromobacter xylosoxidans*. Alcohol dehydrogenases can also include horse liver ADH and *Beijerinkia indica* ADH, as described by U.S. Patent Application Publication No. 2011/0269199, which is incorporated herein by reference in its entirety.

The term "butanol dehydrogenase" refers to a polypeptide (or polypeptides) having an enzyme activity that catalyzes the conversion of isobutyraldehyde to isobutanol or the conversion of 2-butanone and 2-butanol. Butanol dehydrogenases are a subset of a broad family of alcohol dehydrogenases. Butanol dehydrogenase may be NAD- or NADP-dependent. The NAD-dependent enzymes are known as EC 1.1.1.1 and are available, for example, from *Rhodococcus ruber* (GenBank Nos: CAD36475, AJ491307). The NADP dependent enzymes are known as EC 1.1.1.2 and are available, for example, from *Pyrococcus furiosus* (GenBank Nos: AAC25556, AF013169). Additionally, a butanol dehydrogenase is available from *Escherichia coli* (GenBank Nos: NP_417484, NC_000913) and a cyclohexanol dehydrogenase is available from *Acinetobacter* sp. (GenBank Nos: AAG10026, AF282240). The term "butanol dehydrogenase" also refers to an enzyme that catalyzes the conversion of butyraldehyde to 1-butanol, using either NADH or NADPH as cofactor. Butanol dehydrogenases are available from, for example, *C. acetobutylicum* (GenBank NOs: NP_149325, NC_001988; note: this enzyme possesses both aldehyde and alcohol dehydrogenase activity); NP_349891, NC_003030; and NP_349892, NC_003030) and *E. coli* (GenBank NOs: NP_417-484, NC_000913).

The term "branched-chain keto acid dehydrogenase" refers to an enzyme that catalyzes the conversion of α-ketoisovalerate to isobutyryl-CoA (isobutyryl-coenzyme A), typically using $NAD^+$ (nicotinamide adenine dinucleotide) as an electron acceptor. Example branched-chain keto acid dehydrogenases are known by the EC number 1.2.4.4. Such branched-chain keto acid dehydrogenases are comprised of four subunits and sequences from all subunits are available from a vast array of microorganisms, including, but not limited to, *B. subtilis* (GenBank Nos: CAB14336, Z99116; CAB14335, Z99116; CAB14334, Z99116; and CAB14337, Z99116) and *Pseudomonas putida* (GenBank Nos: AAA65614, M57613; AAA65615, M57613; AAA65617, M57613; and AAA65618, M57613).

The term "acylating aldehyde dehydrogenase" refers to an enzyme that catalyzes the conversion of isobutyryl-CoA to isobutyraldehyde, typically using either NADH or NADPH as an electron donor. Example acylating aldehyde dehydrogenases are known by the EC numbers 1.2.1.10 and 1.2.1.57. Such enzymes are available from multiple sources, including, but not limited to, *Clostridium beijerinckii* (GenBank Nos: AAD31841, AF157306), *C. acetobutylicum* (GenBank Nos: NP_149325, NC_001988; NP_149199, NC_001988),

*P. putida* (GenBank Nos: AAA89106, U13232), and *Thermus thermophilus* (GenBank Nos: YP_145486, NC_006461).

The term "transaminase" refers to an enzyme that catalyzes the conversion of α-ketoisovalerate to L-valine, using either alanine or glutamate as an amine donor. Example transaminases are known by the EC numbers 2.6.1.42 and 2.6.1.66. Such enzymes are available from a number of sources. Examples of sources for alanine-dependent enzymes include, but are not limited to, *E. coli* (GenBank Nos: YP_026231, NC_000913) and *Bacillus licheniformis* (GenBank Nos: YP_093743, NC_006322). Examples of sources for glutamate-dependent enzymes include, but are not limited to, *E. coli* (GenBank Nos: YP_026247, NC_000913), *Saccharomyces cerevisiae* (GenBank Nos: NP_012682, NC_001142) and *Methanobacterium thermoautotrophicum* (GenBank Nos: NP_276546, NC_000916).

The term "valine dehydrogenase" refers to an enzyme that catalyzes the conversion of α-ketoisovalerate to L-valine, typically using NAD(P)H as an electron donor and ammonia as an amine donor. Example valine dehydrogenases are known by the EC numbers 1.4.1.8 and 1.4.1.9 and such enzymes are available from a number of sources, including, but not limited to, *Streptomyces coelicolor* (GenBank Nos: NP_628270, NC_003888) and *B. subtilis* (GenBank Nos: CAB14339, Z99116).

The term "valine decarboxylase" refers to an enzyme that catalyzes the conversion of L-valine to isobutylamine and $CO_2$. Example valine decarboxylases are known by the EC number 4.1.1.14. Such enzymes are found in *Streptomyces*, such as for example, *Streptomyces viridifaciens* (GenBank Nos: AAN10242, AY116644).

The term "omega transaminase" refers to an enzyme that catalyzes the conversion of isobutylamine to isobutyraldehyde using a suitable amino acid as an amine donor. Example omega transaminases are known by the EC number 2.6.1.18 and are available from a number of sources, including, but not limited to, *Alcaligenes denitrificans* (AAP92672, AY330220), *Ralstonia eutropha* (GenBank Nos: YP_294474, NC_007347), *Shewanella oneidensis* (GenBank Nos: NP_719046, NC_004347), and *P. putida* (GenBank Nos: AAN66223, AE016776).

The term "acetyl-CoA acetyltransferase" refers to an enzyme that catalyzes the conversion of two molecules of acetyl-CoA to acetoacetyl-CoA and coenzyme A (CoA). Example acetyl-CoA acetyltransferases are acetyl-CoA acetyltransferases with substrate preferences (reaction in the forward direction) for a short chain acyl-CoA and acetyl-CoA and are classified as E.C. 2.3.1.9 [Enzyme Nomenclature 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1, NC_003030; NP_149242, NC_001988, *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to an enzyme that catalyzes the conversion of acetoacetyl-CoA to 3-hydroxybutyryl-CoA. 3-Example hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA. Examples may be classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314, NC_003030), *B. subtilis* (GenBank NOs: AAB09614, U29084), *Ralstonia eutropha* (GenBank NOs: YP_294481, NC_007347), and *Alcaligenes eutrophus* (GenBank NOs: AAA21973, J04987).

The term "crotonase" refers to an enzyme that catalyzes the conversion of 3-hydroxybutyryl-CoA to crotonyl-CoA and $H_2O$. Example crotonases may have a substrate preference for (S)-3-hydroxybutyryl-CoA or (R)-3-hydroxybutyryl-CoA and may be classified as E.C. 4.2.1.17 and E.C. 4.2.1.55, respectively. Crotonases are available from a number of sources, for example, *E. coli* (GenBank NOs: NP_415911, NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase" refers to an enzyme that catalyzes the conversion of crotonyl-CoA to butyryl-CoA. Example butyryl-CoA dehydrogenases may be NADH-dependent, NADPH-dependent, or flavin-dependent and may be classified as E.C. 1.3.1.44, E.C. 1.3.1.38, and E.C. 1.3.99.2, respectively. Butyryl-CoA dehydrogenases are available from a number of sources, for example, *C. acetobutylicum* (GenBank NOs: NP_347102, NC_003030), *Euglena gracilis* (GenBank NOs: Q5EU90, AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841, AF157306) and *C. acetobutylicum* (GenBank NOs: NP_149325, NC_001988).

The term "isobutyryl-CoA mutase" refers to an enzyme that catalyzes the conversion of butyryl-CoA to isobutyryl-CoA. This enzyme uses coenzyme $B_{12}$ as cofactor. Example isobutyryl-CoA mutases are known by the EC number 5.4.99.13. These enzymes are found in a number of *Streptomyces*, including, but not limited to, *Streptomyces cinnamonensis* (GenBank Nos: AAC08713, U67612; CAB59633, AJ246005), *S. coelicolor* (GenBank Nos: CAB70645, AL939123; CAB92663, AL939121), and *Streptomyces avermitilis* (GenBank Nos: NP_824008, NC_003155; NP_824637, NC_003155).

The term "acetolactate decarboxylase" refers to a polypeptide (or polypeptides) having an enzyme activity that catalyzes the conversion of alpha-acetolactate to acetoin. Example acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (GenBank Nos: AAU43774, AY722056).

The term "acetoin aminase" or "acetoin transaminase" refers to a polypeptide (or polypeptides) having an enzyme activity that catalyzes the conversion of acetoin to 3-amino-2-butanol. Acetoin aminase may utilize the cofactor pyridoxal 5'-phosphate or NADH (reduced nicotinamide adenine dinucleotide) or NADPH (reduced nicotinamide adenine dinucleotide phosphate). The resulting product may have (R) or (S) stereochemistry at the 3-position. The pyridoxal phosphate-dependent enzyme may use an amino acid such as alanine or glutamate as the amino donor. The NADH- and NADPH-dependent enzymes may use ammonia as a second substrate. A suitable example of an NADH dependent acetoin aminase, also known as amino alcohol dehydrogenase, is described by Ito, et al. (U.S. Pat. No. 6,432,688). An example of a pyridoxal-dependent acetoin aminase is the amine:pyruvate aminotransferase (also called amine:pyruvate transaminase) described by Shin and Kim (J. Org. Chem. 67:2848-2853, 2002).

The term "acetoin kinase" refers to a polypeptide (or polypeptides) having an enzyme activity that catalyzes the conversion of acetoin to phosphoacetoin. Acetoin kinase may utilize ATP (adenosine triphosphate) or phosphoenolpyruvate as the phosphate donor in the reaction. Enzymes that catalyze the analogous reaction on the similar substrate dihydroxyacetone, for example, include enzymes known as EC 2.7.1.29 (Garcia-Alles, et al., *Biochemistry* 43:13037-13046, 2004).

The term "acetoin phosphate aminase" refers to a polypeptide (or polypeptides) having an enzyme activity that catalyzes the conversion of phosphoacetoin to 3-amino-2-butanol O-phosphate. Acetoin phosphate aminase may use the cofactor pyridoxal 5'-phosphate, NADH or NADPH. The resulting product may have (R) or (S) stereochemistry at the 3-position. The pyridoxal phosphate-dependent enzyme may use an amino acid such as alanine or glutamate. The NADH and NADPH-dependent enzymes may use ammonia as a second substrate. Although there are no reports of enzymes catalyzing this reaction on phosphoacetoin, there is a pyridoxal phosphate-dependent enzyme that is proposed to carry out the analogous reaction on the similar substrate serinol phosphate (Yasuta, et al., *Appl. Environ. Microbiol.* 67:4999-5009, 2001).

The term "aminobutanol phosphate phospholyase," also called "amino alcohol O-phosphate lyase," refers to a polypeptide (or polypeptides) having an enzyme activity that catalyzes the conversion of 3-amino-2-butanol O-phosphate to 2-butanone. Amino butanol phosphate phospho-lyase may utilize the cofactor pyridoxal 5'-phosphate. There are reports of enzymes that catalyze the analogous reaction on the similar substrate 1-amino-2-propanol phosphate (Jones, et al., *Biochem J.* 134:167-182, 1973). U.S. Patent Application Publication No. 2007/0259410 describes an aminobutanol phosphate phospho-lyase from the organism *Erwinia carotovora*.

The term "aminobutanol kinase" refers to a polypeptide (or polypeptides) having an enzyme activity that catalyzes the conversion of 3-amino-2-butanol to 3-amino-2-butanol O-phosphate. Amino butanol kinase may utilize ATP as the phosphate donor. Although there are no reports of enzymes catalyzing this reaction on 3-amino-2-butanol, there are reports of enzymes that catalyze the analogous reaction on the similar substrates ethanolamine and 1-amino-2-propanol (Jones, et al., supra). U.S. Patent Application Publication No. 2009/0155870 describes, in Example 14, an amino alcohol kinase of *Erwinia carotovora* subsp. *Atroseptica*.

The term "butanediol dehydrogenase" also known as "acetoin reductase" refers to a polypeptide (or polypeptides) having an enzyme activity that catalyzes the conversion of acetoin to 2,3-butanediol. Butanedial dehydrogenases are a subset of the broad family of alcohol dehydrogenases. Butanediol dehydrogenase enzymes may have specificity for production of (R)- or (S)-stereochemistry in the alcohol product. (S)-specific butanediol dehydrogenases are known as EC 1.1.1.76 and are available, for example, from *Klebsiella pneumoniae* (GenBank Nos: BBA13085, D86412). (R)-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase," also known as "dial dehydratase" or "propanediol dehydratase" refers to a polypeptide (or polypeptides) having an enzyme activity that catalyzes the conversion of 2,3-butanediol to 2-butanone. Butanediol dehydratase may utilize the cofactor adenosyl cobalamin (also known as coenzyme Bw or vitamin $B_{12}$; although vitamin B12 may refer also to other forms of cobalamin that are not coenzyme B12). Adenosyl cobalamin-dependent enzymes are known as EC 4.2.1.28 and are available, for example, from *Klebsiella oxytoca* (GenBank Nos: AA08099 (alpha subunit), D45071; BAA08100 (beta subunit), D45071; and BBA08101 (gamma subunit), D45071 (Note all three subunits are required for activity), and *Klebsiella pneumonia* (GenBank Nos: AAC98384 (alpha subunit), AF102064; GenBank Nos: AAC98385 (beta subunit), AF102064, GenBank Nos: AAC98386 (gamma subunit), AF102064). Other suitable dial dehydratases include, but are not limited to, B12-dependent dial dehydratases available from *Salmonella typhimurium* (GenBank Nos: AAB84102 (large subunit), AF026270; GenBank Nos: AAB84103 (medium subunit), AF026270; GenBank Nos: AAB84104 (small subunit), AF026270); and *Lactobacillus collinoides* (GenBank Nos: CAC82541 (large subunit), AJ297723; GenBank Nos: CAC82542 (medium subunit); AJ297723; GenBank Nos: CAD01091 (small subunit), AJ297723); and enzymes from *Lactobacillus brevis* (particularly strains CNRZ 734 and CNRZ 735, Speranza, et al., *J. Agric. Food Chem.* 45:3476-3480, 1997), and nucleotide sequences that encode the corresponding enzymes. Methods of diol dehydratase gene isolation are well known in the art (e.g., U.S. Pat. No. 5,686,276).

The term "pyruvate decarboxylase" refers to an enzyme that catalyzes the decarboxylation of pyruvic acid to acetaldehyde and carbon dioxide. Pyruvate dehydrogenases are known by the EC number 4.1.1.1. These enzymes are found in a number of yeast, including *Saccharomyces cerevisiae* (GenBank Nos: CAA97575, CAA97705, CAA97091).

It will be appreciated that host cells comprising an isobutanol biosynthetic pathway as provided herein may further comprise one or more additional modifications. U.S. Patent Application Publication No. 2009/0305363 (incorporated by reference) discloses increased conversion of pyruvate to acetolactate by engineering yeast for expression of a cytosol-localized acetolactate synthase and substantial elimination of pyruvate decarboxylase activity. In some embodiments, the host cells comprise modifications to reduce glycerol-3-phosphate dehydrogenase activity and/or disruption in at least one gene encoding a polypeptide having pyruvate decarboxylase activity or a disruption in at least one gene encoding a regulatory element controlling pyruvate decarboxylase gene expression as described in U.S. Patent Application Publication No. 2009/0305363 (incorporated herein by reference), modifications to a host cell that provide for increased carbon flux through an Entner-Doudoroff Pathway or reducing equivalents balance as described in U.S. Patent Application Publication No. 2010/0120105 (incorporated herein by reference). Other modifications include integration of at least one polynucleotide encoding a polypeptide that catalyzes a step in a pyruvate-utilizing biosynthetic pathway.

Other modifications include at least one deletion, mutation, and/or substitution in an endogenous polynucleotide encoding a polypeptide having acetolactate reductase activity. As used herein, "acetolactate reductase activity" refers to the activity of any polypeptide having the ability to catalyze the conversion of acetolactate to DHMB. Such polypeptides can be determined by methods well known in the art and disclosed herein. As used herein, "DHMB" refers to 2,3-dihydroxy-2-methyl butyrate. DHMB includes "fast DHMB," which has the 2S, 3S configuration, and "slow DHMB," which has the 2S, 3R configurate. See Kaneko et al., *Phytochemistry* 39: 115-120 (1995), which is herein incorporated by reference in its entirety and refers to fast DHMB as anglyceric acid and slow DHMB as tiglyceric acid. In embodiments, the polypeptide having acetolactate reductase activity is YMR226C of *Saccharomyces cerevisiae* or a homolog thereof.

Additional modifications include a deletion, mutation, and/or substitution in an endogenous polynucleotide encoding a polypeptide having aldehyde dehydrogenase and/or aldehyde oxidase activity. As used herein, "aldehyde dehydrogenase activity" refers to any polypeptide having a biological function of an aldehyde dehydrogenase. Such polypeptides include a polypeptide that catalyzes the oxidation (dehydrogenation) of aldehydes. Such polypeptides include a polypeptide that catalyzes the conversion of isobutyraldehyde to isobutyric acid. Such polypeptides also include a polypeptide that corresponds to Enzyme Commission Numbers EC 1.2.1.3, EC 1.2.1.4 or EC 1.2.1.5. Such polypeptides can be determined by methods well known in the art and disclosed herein. As used herein, "aldehyde oxidase activity" refers to any polypeptide having a biological function of an aldehyde oxidase. Such polypeptides include a polypeptide that catalyzes production of carboxylic acids from aldehydes. Such polypeptides include a polypeptide that catalyzes the conversion of isobutyraldehyde to isobutyric acid. Such polypeptides also include a polypeptide that corresponds to Enzyme Commission Number EC 1.2.3.1. Such polypeptides can be determined by methods well known in the art and disclosed herein. In some embodiments, the polypeptide having aldehyde dehydrogenase activity is ALD6 from *Saccharomyces cerevisiae* or a homolog thereof A genetic modification which has the effect of reducing glucose repression wherein the yeast production host cell is pdc– is described in U.S. Patent Application Publication No. 2011/0124060, incorporated herein by reference. In some embodiments, the pyruvate decarboxylase that is deleted or down-regulated is selected from the group consisting of: PDC1, PDC5, PDC6, and combinations thereof. In some embodiments, the pyruvate decarboxylase is selected from PDC1 pyruvate decarboxylase from *Saccharomyces cerevisiae*, PDC5 pyruvate decarboxylase from *Saccharomyces cerevisiae*, PDC6 pyruvate decarboxylase from *Saccharomyces cerevisiae*, pyruvate decarboxylase from *Candida glabrata*, PDC1 pyruvate decarboxylase from *Pichia stipites*, PDC2 pyruvate decarboxylase from *Pichia stipites*, pyruvate decarboxylase from *Kluveromyces lactis*, pyruvate decarboxylase from *Yarrowia lipolytica*, pyruvate decarboxylase from *Schizosaccharomyces pombe*, and pyruvate decarboxylase from *Zygosaccharomyces rouxii*. In some embodiments, host cells contain a deletion or down-regulation of a polynucleotide encoding a polypeptide that catalyzes the conversion of glyceraldehyde-3-phosphate to glycerate 1,3, bisphosphate. In some embodiments, the enzyme that catalyzes this reaction is glyceraldehyde-3-phosphate dehydrogenase.

WIPO publication number WO 2001/103300 discloses recombinant host cells comprising (a) at least one heterologous polynucleotide encoding a polypeptide having dihydroxy-acid dehydratase activity; and (b)(i) at least one deletion, mutation, and/or substitution in an endogenous gene encoding a polypeptide affecting Fe—S cluster biosynthesis; and/or (ii) at least one heterologous polynucleotide encoding a polypeptide affecting Fe—S cluster biosynthesis. In embodiments, the polypeptide affecting Fe—S cluster biosynthesis is encoded by AFT1, AFT2, FRA2, GRX3, or CCC1. In embodiments, the polypeptide affecting Fe—S cluster biosynthesis is constitutive mutant AFT1 L99A, AFT1 L102A, AFT1 C291F, or AFT1 C293F.

Additionally, host cells may comprise heterologous polynucleotides encoding a polypeptide with phosphoketolase activity and/or a heterologous polynucleotide encoding a polypeptide with phosphotransacetylase activity.

In some embodiments, any particular nucleic acid molecule or polypeptide may be at least 80%, 85%, 90%, 95%, 96%, 97%, 98%, or 99% identical to a nucleotide sequence or polypeptide sequence described herein. The term "percent identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those disclosed in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Standard recombinant DNA and molecular cloning techniques are well known in the art and are described by Sambrook, et al. (Sambrook, J., Fritsch, E. F. and Maniatis, T. (Molecular Cloning: A Laboratory Manual; Cold Spring Harbor Laboratory Press, Cold Spring Harbor, 1989, here in referred to as Maniatis) and by Ausubel, et al. (Ausubel, et al., *Current Protocols in Molecular Biology*, pub. by Greene Publishing Assoc. and Wiley-Interscience, 1987). Examples of methods to construct microorganisms that comprise a butanol biosynthetic pathway are disclosed, for example, in U.S. Pat. No. 7,851,188, and U.S. Patent Application Publication Nos. 2007/0092957; 2007/0259410; 2007/0292927; 2008/0182308; 2008/0274525; 2009/0155870; 2009/0305363; and 2009/0305370, the entire contents of each are herein incorporated by reference.

Organic Extractants

A product alcohol may be recovered from fermentation broth using a number of methods including liquid-liquid extraction. In some embodiments of the processes and systems described herein, an extractant may be used to recover product alcohol from fermentation broth. Extractants used herein may be have, for example, one or more of the following properties and/or characteristics: (i) biocompatible with the microorganisms, (ii) immiscible with the fermentation medium, (iii) a high partition coefficient ($K_d$) for the extraction of product alcohol, (iv) a low partition coefficient for the extraction of nutrients and other side products, (v) a low spreading coefficient, (vi) a high interfacial tension with water, (vii) low viscosity (μ), (viii) high selectivity for product alcohol as compared to, for example, water, (ix) low density (ρ) relative to the fermentation medium, (x) boiling point suitable for downstream processing of the extractant and product alcohol, (xi) melting point lower than ambient temperature, (xii) minimal solubility in solids, (xiii) a low tendency to form emulsions with the fermentation medium, (xiv) stability over the fermentation process, (xv) low cost, (xvi) commercial availability, and (xvii) nonhazardous.

In some embodiments, the extractant may be selected based upon certain properties and/or characteristics as described above. For example, viscosity of the extractant can influence the mass transfer properties of the system, for example, the efficiency with which the product alcohol may be extracted from the aqueous phase to the extractant phase (i.e., organic phase). The density of the extractant can affect phase separation. In some embodiments, the extractant may be liquid at the temperatures of the fermentation process. In some embodiments, selectivity refers to the relative amounts of product alcohol to water taken up by the extractant. The boiling point can affect the cost and method of product alcohol recovery. For example, in the case where butanol is recovered from the extractant phase by distillation, the boiling point of the extractant should be sufficiently low as to enable separation of butanol while minimizing any thermal degradation or side reactions of the extractant, or the need for vacuum in the distillation process.

The extractant can be biocompatible with the microorganism, that is, nontoxic to the microorganism or toxic only to such an extent that the microorganism is impaired to an acceptable level. In some embodiments, biocompatible refers to the measure of the ability of a microorganism to utilize fermentable carbon sources in the presence of an extractant. The extent of biocompatibility of an extractant may be determined, for example, by the glucose utilization rate of the microorganism in the presence of the extractant and product alcohol. In some embodiments, a non-biocompatible extractant refers to an extractant that interferes with the ability of a microorganism to utilize fermentable carbon sources. For example, a non-biocompatible extractant does not permit the microorganism to utilize glucose at a rate greater than about 25%, greater than about 30%, greater than about 35%, greater than about 40%, greater than about 45%, or greater than about 50% of the rate when the extractant is not present.

One skilled in the art may select an extractant to maximize the desired properties and/or characteristics as described above and to optimize recovery of a product alcohol. One of skill in the art can also appreciate that it may be advantageous to use a mixture of extractants. For example, extractant mixtures may be used to increase the partition coefficient for the product alcohol. Additionally, extractant mixtures may be used to adjust and optimize physical characteristics of the extractant, such as the density, boiling point, and viscosity. For example, the appropriate combination may provide an extractant which has a sufficient partition coefficient for the product alcohol, sufficient biocompatibility to enable its economical use for removing product alcohol from a fermentative broth, and sufficient selectivity to enable the selective removal of the product alcohol over, for example, water.

Suitable organic extractants for use in the methods disclosed herein are selected from the group consisting of $C_{12}$ to $C_{22}$ fatty alcohols, $C_{12}$ to $C_{22}$ ethers, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, $C_{10}$ to $C_{22}$ alkanes, and mixtures thereof. In some embodiments, the solvent is trimethylnonanol, methyl laurate, di-n-octyl ether, dodecane, n-undecane, ethyl decanoate, ethyl laurate, or mixtures thereof. In some embodiments, the solvent is not oleyl alcohol, 1-dodecanol, behenyl alcohol, cetyl alcohol, myristyl alcohol, or stearyl alcohol. As used herein, the term "mixtures thereof" encompasses both mixtures within and mixtures between these group members, including structural homologs, for example mixtures within $C_{12}$ to $C_{22}$ fatty alcohols, $C_{12}$ to $C_{22}$ ethers, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and $C_{10}$ to $C_{22}$ alkanes.

In some embodiments, the solvent has a boiling point less than about 320° C., less than about 310° C., less than about 300° C., less than about 290° C., less than about 280° C., less than about 270° C., less than about 260° C., less than about 250° C., less than about 240° C., less than about 230° C., less than about 220° C., less than about 210° C., or less than about 200° C.

In some embodiments, the solvent is biocompatible with the microorganism such that at least about 70%, at least about 75%, at least about 80%, at least about 85%, at least about 90%, or at least about 95% of the microorganism is viable after exposure to the organic extractant composition. In some embodiments, at least 90%, at least 80%, at least 70%, or at least 60% of the butanol-producing microorganisms are viable after exposure of the fermentation medium to the organic extractant for 25 hours. In other embodiments, at least 90%, at least 80%, at least 70%, or at least 60% of the butanol-producing microorganisms are viable after exposure of the fermentation medium to the organic extractant for 30 hours.

Suitable organic extractant compositions can also include a mixture of a first solvent and a second solvent. A suitable first solvent can include a solvent having one or more of the characteristics described in the preceding paragraph. For example, the first solvent can be trimethylnonanol, methyl laurate, di-n-octyl ether, dodecane, n-undecane, ethyl decanoate, ethyl laurate. In certain embodiments, suitable second solvents include solvents having a higher butanol partition coefficient than the first solvent. Optionally, the second solvent may have a higher toxicity to a recombinant microorganism comprising a butanol biosynthetic pathway than the first solvent. In some embodiments, the second solvent has a butanol partition coefficient greater than about 4, greater than about 4.5, greater than about 5, greater than about 5.5, greater than about 6, greater than about 6.5, greater than about 7, greater than about 7.5, or greater than about 8. Examples of a suitable second solvent in the organic extractant include n-hexanol, methyl isobutyl carbinol, 2-ethyl-1-hexanol, 2,6-dimethylheptan-4-ol, and mixtures thereof. Additional examples of a suitable second solvent can include, but is not limited to, an organic solvent such as oleic acid, lauric acid, myristic acid, stearic acid, octanoic acid, decanoic acid, undecanoic acid, methyl myristate, methyl oleate, 1-nonanol, 1-decanol, 2-undecanol, 1-nonanal, 1-undecanol, undecanal, lauric aldehyde, 2-methylundecanal, oleamide, linoleamide, palmitamide, stearylamide, 2-hexyl-1-decanol, 2-octyl-1-dodecanol, and mixtures thereof In some embodiments, the extractant may be a mixture of biocompatible and non-biocompatible extractants. Examples of mixtures of biocompatible and non-biocompatible extractants include, but are not limited to, trimethylnonanol and n-hexanol, trimethylnonanol and methyl isobutyl carbinol, trimethylnonanol and 2-ethyl-1-hexanol, trimethylnonanol and 2,6-dimethylheptan-4-ol, methyl laurate and n-hexanol, methyl laurate and methyl isobutyl carbinol, methyl laurate and 2-ethyl-1-hexanol, methyl laurate and 2,6-dimethylheptan-4-ol, di-n-octyl ether and n-hexanol, di-n-octyl ether and methyl isobutyl carbinol, di-n-octyl ether and 2-ethyl-1-hexanol, di-n-octyl ether and 2,6-dimethylheptan-4-ol, dodecane and n-hexanol, dodecane and methyl isobutyl carbinol, dodecane and 2-ethyl-1-hexanol, dodecane 1 and 2,6-dimethylheptan-4-ol, n-undecane and n-hexanol, n-undecane and methyl isobutyl carbinol, n-undecane and 2-ethyl-1-hexanol, n-undecane and 2,6-dimethylheptan-4-ol, ethyl decanoate and n-hexanol, ethyl decanoate and methyl isobutyl carbinol, ethyl decanoate and 2-ethyl-1-hexanol, ethyl decanoate and 2,6-dimethylheptan-4-ol, ethyl laurate and n-hexanol, ethyl laurate and methyl isobutyl carbinol, ethyl laurate and 2-ethyl-1-hexanol, and ethyl laurate and 2,6-dimethylheptan-4-ol. Additional examples of biocompatible and non-biocompatible extractants are described in U.S. Patent Application Publication No. 2009/0305370 and U.S. Patent Application Publication No. 2011/0097773; the entire contents of each herein incorporated by reference. In some embodiments, biocompatible extractants may have high atmospheric boiling points. For example, biocompatible extractants may have atmospheric boiling points greater than the atmospheric boiling point of water.

The relative amounts of the first and second solvents which form the extractant can vary within a suitable range. In some embodiments, the extractant composition can contain about 30 percent to about 90 percent of the first solvent, based on the total volume of the first and second solvents. In some embodiments, the extractant can contain about 40 percent to about 80 percent first solvent. In some embodiments, the extractant can contain about 45 percent to about 75 percent first solvent. In another embodiment, the extractant can contain about 50 percent to about 70 percent first solvent. The optimal range reflects maximization of the extractant characteristics, for example balancing a relatively high partition coefficient for butanol with an acceptable level of biocompatibility. For a two-phase extractive fermentation for the production or recovery of butanol, the temperature, contacting time, butanol concentration in the fermentation medium, relative amounts of extractant and fermentation medium, specific solvent(s) used, relative amounts of the first and second solvents (when more than one solvent is used), presence of other organic solutes, and the amount and type of microorganism are related; thus these variables can be adjusted as necessary within appropriate limits to optimize the extraction process as described herein.

These organic extractants are available commercially from various sources, such as Sigma-Aldrich (St. Louis, Mo.), in various grades, many of which can be suitable for use in extractive fermentation to produce or recover butanol. Technical grades contain a mixture of compounds, including the desired component and higher and lower fatty components.

Growth for Production

Recombinant host cells disclosed herein are contacted with suitable carbon substrates, typically in fermentation media. Additional carbon substrates may include, but are not limited to, monosaccharides such as fructose, oligosaccharides such as lactose, maltose, galactose, or sucrose, polysaccharides such as starch or cellulose or mixtures thereof and unpurified mixtures from renewable feedstocks such as cheese whey permeate, cornsteep liquor, sugar beet molasses, and barley malt. Other carbon substrates can include ethanol, lactate, succinate, or glycerol.

Additionally the carbon substrate may also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth C1 Compd.*, [Int. Symp.], $7^{th}$ (1993), 415-32, Editors: Murrell, J. Collin, Kelly, Don P.; Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose can be derived from renewable grain sources through saccharification of starch based feedstocks including grains such as corn, wheat, rye, barley, oats, and mixtures thereof. In addition, fermentable sugars can be derived from renewable cellulosic or lignocellulosic biomass through processes of pretreatment and saccharification, as described, for example, in U.S. Patent Application Publication No. 2007/0031918 A1, which is herein incorporated by reference. Biomass, when used in reference to carbon substrate, refers to any cellulosic or lignocellulosic material and includes materials comprising cellulose, and optionally further comprising hemicellulose, lignin, starch, oligosaccharides and/or monosaccharides. Biomass can also comprise additional components, such as protein and/or lipid. Biomass can be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of an enzymatic pathway described herein.

Culture Conditions

Typically cells are grown at a temperature in the range of about 20° C. to about 40° C. in an appropriate medium. Suitable growth media in the present invention are common commercially prepared media such as Luria Bertani (LB)

broth, Sabouraud Dextrose (SD) broth or Yeast Medium (YM) broth or broth that includes yeast nitrogen base, ammonium sulfate, and dextrose (as the carbon/energy source) or YPD Medium, a blend of peptone, yeast extract, and dextrose in optimal proportions for growing most *Saccharomyces cerevisiae* strains. Other defined or synthetic growth media can also be used, and the appropriate medium for growth of the particular microorganism will be known by one skilled in the art of microbiology or fermentation science. The use of agents known to modulate catabolite repression directly or indirectly, e.g., cyclic adenosine 2',3'-monophosphate (cAMP), can also be incorporated into the fermentation medium.

Suitable pH ranges for the fermentation are between pH 5.0 to pH 9.0, where pH 6.0 to pH 8.0 is preferred for the initial condition. Suitable pH ranges for the fermentation of yeast are typically between about pH 3.0 to about pH 9.0. In one embodiment, about pH 5.0 to about pH 8.0 is used for the initial condition. Suitable pH ranges for the fermentation of other microorganisms are between about pH 3.0 to about pH 7.5. In one embodiment, about pH 4.5 to about pH 6.5 is used for the initial condition.

Fermentations can be performed under aerobic or anaerobic conditions. In one embodiment, anaerobic or microaerobic conditions are used for fermentation.

Industrial Batch and Continuous Fermentations

Butanol, or other products, can be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments at the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples can be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.,* 36:227, (1992), herein incorporated by reference.

Butanol, or other products, may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol, or other products, can be practiced using batch, fed-batch or continuous processes and that any known mode of fermentation would be suitable. Additionally, it is contemplated that cells can be immobilized on a substrate as whole cell catalysts and subjected to fermentation conditions for butanol production.

Methods for Recovering Butanol Using Two-Phase Extractive Fermentation

Bioproduced butanol may be recovered from a fermentation medium containing butanol, water, at least one fermentable carbon source, and a microorganism that has been genetically modified (that is, genetically engineered) to produce butanol via a biosynthetic pathway from at least one carbon source. The first step in the process is contacting the fermentation medium with a water immiscible organic extractant composition comprising a solvent, as described above, to form a two-phase mixture comprising an aqueous phase and a butanol-containing organic phase. "Contacting" means the fermentation medium and the organic extractant composition or its solvent component(s) are brought into physical contact at any time during the fermentation process. In one embodiment, the fermentation medium further comprises ethanol, and the butanol-containing organic phase can contain ethanol.

In certain embodiments where more than one solvent is used for the extraction, the contacting may be performed with the solvents of the extractant composition having been previously combined. For example, the first and second solvents may be combined in a vessel such as a mixing tank to form the extractant, which is then added to a vessel containing the fermentation medium. Alternatively, the contacting may be performed with the first and second solvents becoming combined during the contacting. For example, the first and second solvents may be added separately to a vessel which contains the fermentation medium. In one embodiment, contacting the fermentation medium with the organic extractant composition further comprises contacting the fermentation medium with the first solvent prior to contacting the fermentation medium and the first solvent with the second solvent. In one embodiment, the contacting with the second solvent occurs in the same vessel as the contacting with the first solvent. In one embodiment, the contacting with the second solvent occurs in a different vessel from the contacting with the first solvent. For example, the first solvent may be contacted with the fermentation medium in one vessel, and the contents transferred to another vessel in which contacting with the second solvent occurs.

The organic extractant composition can contact the fermentation medium at the start of the fermentation forming a biphasic fermentation medium. Alternatively, the organic extractant composition can contact the fermentation medium after the microorganism has achieved a desired amount of growth, which can be determined by measuring the optical density of the culture.

Further, the organic extractant composition can contact the fermentation medium at a time at which the butanol level in the fermentation medium reaches a preselected level, for example, before the butanol concentration reaches a toxic level. The butanol concentration can be monitored during the fermentation using methods known in the art, such as gas chromatography or high performance liquid chromatography.

Fermentation can be run under aerobic conditions for a time sufficient for the culture to achieve a preselected level of growth, as determined by optical density measurement. An inducer can then be added to induce the expression of the butanol biosynthetic pathway in the modified microorganism, and fermentation conditions are switched to microaerobic or anaerobic conditions to stimulate butanol production, as described, for example, in detail in Example 6 of US Patent Application Publication No. 2009/0305370. The extractant is added after the switch to microaerobic or anaerobic conditions.

Through contacting the fermentation medium with the organic extractant composition, the butanol product partitions into the organic extractant, decreasing the concentration in the aqueous phase containing the microorganism, thereby limiting the exposure of the production microorganism to the inhibitory butanol product. The volume of the organic extractant to be used depends on a number of factors, including the volume of the fermentation medium, the size of the fermentor, the partition coefficient of the extractant for the butanol product, and the fermentation mode chosen, as described below. The volume of the organic extractant is about 3% to about 60% of the fermentor working volume. The ratio of the extractant to the fermentation medium is from about 1:20 to about 20:1 on a volume:volume basis, for example from about 1:15 to about 15:1, or from about 1:12 to about 12:1, or from about 1:10 to about 10:1, or from about 1:9 to about 9:1, or from about 1:8 to about 8:1.

The next step is separating the butanol-containing organic phase from the aqueous phase using methods known in the art, including but not limited to, siphoning, decantation, centrifugation, using a gravity settler, and membrane-assisted phase splitting. Recovery of the butanol from the butanol-containing organic phase can be done using methods known in the art, including but not limited to, distillation, adsorption by resins, separation by molecular sieves, and pervaporation. Specifically, distillation can be used to recover the butanol from the butanol-containing organic phase.

Gas stripping can be used concurrently with the solvents of the organic extractant composition to remove the butanol product from the fermentation medium. Gas stripping may be done by passing a gas such as air, nitrogen, or carbon dioxide through the fermentation medium, thereby forming a butanol-containing gas phase. The butanol product may be recovered from the butanol-containing gas phase using methods known in the art, such as using a chilled water trap to condense the butanol, or scrubbing the gas phase with a solvent.

Any butanol remaining in the fermentation medium after the fermentation run is completed may be recovered by continued extraction using fresh or recycled organic extractant. Alternatively, the butanol can be recovered from the fermentation medium using methods known in the art, including, but not limited to distillation, azeotropic distillation, liquid-liquid extraction, adsorption, gas stripping, membrane evaporation, pervaporation, and the like.

The two-phase extractive fermentation method may be carried out in a continuous mode in a stirred tank fermentor. In this mode, the mixture of the fermentation medium and the butanol-containing organic extractant composition is removed from the fermentor. The two phases are separated by means known in the art including, but not limited to, siphoning, decantation, centrifugation, using a gravity settler, membrane-assisted phase splitting, and the like, as described above. After separation, the fermentation medium may be recycled to the fermentor or may be replaced with fresh medium. Then, the extractant is treated to recover the butanol product as described above. The extractant may then be recycled back into the fermentor for further extraction of the product. Alternatively, fresh extractant may be continuously added to the fermentor to replace the removed extractant. This continuous mode of operation offers several advantages. Because the product is continually removed from the reactor, a smaller volume of organic extractant composition is required enabling a larger volume of the fermentation medium to be used. This results in higher production yields.

The volume of the organic extractant composition may be about 3% to about 50% of the fermentor working volume; 3% to about 20% of the fermentor working volume; or 3% to about 10% of the fermentor working volume. It is beneficial to use the smallest amount of extractant in the fermentor as possible to maximize the volume of the aqueous phase, and therefore, the amount of cells in the fermentor. The process may be operated in an entirely continuous mode in which the extractant is continuously recycled between the fermentor and a separation apparatus and the fermentation medium is continuously removed from the fermentor and replenished with fresh medium. In this entirely continuous mode, the butanol product is not allowed to reach the critical toxic concentration and fresh nutrients are continuously provided so that the fermentation may be carried out for long periods of time. The apparatus that may be used to carry out these modes of two-phase extractive fermentations are well known in the art. Examples are described, for example, by Kollerup et al. in U.S. Pat. No. 4,865,973.

Batchwise fermentation mode may also be used. Batch fermentation, which is well known in the art, is a closed system in which the composition of the fermentation medium is set at the beginning of the fermentation and is not subjected to artificial alterations during the process. In this mode, a volume of organic extractant composition is added to the fermentor and the extractant is not removed during the process. The organic extractant composition may be formed in the fermentor by separate addition of the first and the second solvents, or the solvents may be combined to form the extractant composition prior to the addition of the extractant composition to the fermentor. Although this mode is simpler than the continuous or the entirely continuous modes described above, it requires a larger volume of organic extractant composition to minimize the concentration of the inhibitory butanol product in the fermentation medium. Consequently, the volume of the fermentation medium is less and the amount of product produced is less than that obtained using the continuous mode. The volume of the organic extractant composition in the batchwise mode may be 20% to about 60% of the fermentor working volume; or 30% to about 60% of the fermentor working volume. It is beneficial to use the smallest volume of extractant in the fermentor as possible, for the reason described above.

Fed-batch fermentation mode may also be used. Fed-batch fermentation is a variation of the standard batch system, in which the nutrients, for example glucose, are added in increments during the fermentation. The amount and the rate of addition of the nutrient may be determined by routine experimentation. For example, the concentration of critical nutrients in the fermentation medium may be monitored during the fermentation. Alternatively, more easily measured factors such as pH, dissolved oxygen, and the partial pressure of waste gases, such as carbon dioxide, may be monitored. From these measured parameters, the rate of nutrient addition may be determined. The amount of organic extractant composition used and its methods of addition in this mode is the same as that used in the batchwise mode, described above.

Extraction of the product may be done downstream of the fermentor, rather than in situ. In this external mode, the extraction of the butanol product into the organic extractant composition is carried out on the fermentation medium removed from the fermentor. The amount of organic solvent used is about 20% to about 60% of the fermentor working volume; or 30% to about 60% of the fermentor working volume. The fermentation medium may be removed from the fermentor continuously or periodically, and the extraction of the butanol product by the organic extractant composition may be done with or without the removal of the cells from the fermentation medium. The cells may be removed from the fermentation medium by means known in the art including, but not limited to, filtration or centrifugation. After separation of the fermentation medium from the extractant by means described above, the fermentation medium may be recycled into the fermentor, discarded, or treated for the removal of any remaining butanol product. Similarly, the isolated cells may also be recycled into the fermentor. After treatment to recover the butanol product, the extractant, the first solvent, and/or the second solvent may be recycled for use in the extraction process. Alternatively, fresh extractant may be used. In this mode the extractant is not present in the fermentor, so the toxicity of the extractant is much less of a problem. If the cells are separated from the fermentation medium before contacting with the extractant, the problem of extractant toxicity is further reduced. Furthermore, using this external mode there is less chance of forming an emulsion and evaporation of the extractant is minimized, alleviating environmental concerns.

An improved method for the production of butanol is provided, wherein a microorganism that has been genetically modified of being capable of converting at least one fermentable carbon source into butanol, is grown in a biphasic fermentation medium. The biphasic fermentation medium comprises an aqueous phase and a water immiscible organic extractant composition, as described above, wherein the biphasic fermentation medium comprises from about 3% to about 60% by volume of the organic extractant. The microorganism can be grown in the biphasic fermentation medium for a time sufficient to extract butanol into the extractant composition to form a butanol-containing organic phase. In the case where the fermentation medium further comprises ethanol, the butanol-containing organic phase can contain ethanol. The butanol-containing organic phase is then separated from the aqueous phase, as described above. Subsequently, the butanol is recovered from the butanol-containing organic phase, as described above.

Also provided is an improved method for the production of butanol wherein a microorganism that has been genetically modified to produce butanol via a biosynthetic pathway from at least one carbon source, is grown in a fermentation medium wherein the microorganism produces the butanol into the fermentation medium to produce a butanol-containing fermentation medium. At least a portion of the butanol-containing fermentation medium is contacted with a water immiscible organic extractant composition, as defined herein, to form a two-phase mixture comprising an aqueous phase and a butanol-containing organic phase. In some embodiments, the fermentation medium further comprises ethanol, and the butanol-containing organic phase can contain ethanol. The butanol-containing organic phase is then separated from the aqueous phase, as described above. Subsequently, the butanol is recovered from the butanol-containing organic phase, as described above. At least a portion of the aqueous phase is returned to the fermentation medium.

Isobutanol can be produced by extractive fermentation with the use of a modified *Escherichia coli* strain in combination with an oleyl alcohol as the organic extractant, as disclosed, for example, in US Patent Application Publication No. 2009/0305370. The method yields a higher effective titer for isobutanol (i.e., 37 g/L) compared to using conventional fermentation techniques (see Example 6 of US Patent Application Publication No. 2009/0305370). For example, Atsumi et al. (Nature 451(3):86-90, 2008) report isobutanol titers up to 22 g/L using fermentation with an *Escherichia coli* that was genetically modified to contain an isobutanol biosynthetic pathway. The higher butanol titer obtained with the extractive fermentation method disclosed in US Patent Application Publication No. 2009/0305370 results, in part, from the removal of the toxic butanol product from the fermentation medium, thereby keeping the level below that which is toxic to the microorganism. It is reasonable to assume that the present extractive fermentation method employing a water-immiscible organic extractant composition, as defined herein, would be used in a similar way and provide similar results.

Butanol produced by the method disclosed herein can have an effective titer of greater than about 20 g per liter of the fermentation medium, greater than about 22 g per liter of the fermentation medium, greater than about 25 g per liter of the fermentation medium, greater than about 30 g per liter of the fermentation medium, greater than about 35 g per liter of the fermentation medium, greater than about 37 g per liter of the fermentation medium, greater than about 40 g per liter of the fermentation medium, greater than about 45 g per liter of the fermentation medium, greater than about 50 g per liter of the fermentation medium. In some embodiments, the recovered butanol has an effective titer from about 22 g per liter to about 50 g per liter, about 22 g per liter to 40 g per liter, about 22 g per liter to about 30 g per liter, about 25 g per liter to about 50 g per liter, about 25 g per liter to 40 g per liter, about 25 g per liter to about 30 g per liter, about 30 g per liter to about 50 g per liter, about 40 g per liter to about 50 g per liter, about 22 g per liter to about 60 g per liter, about 30 g per liter to about 60 g per liter, about 40 g per liter to about 60 g per liter, about 22 g per liter to about 80 g per liter, about 40 g per liter to about 80 g per liter, about 50 g per liter to about 80 g per liter, about 65 g per liter to about 80 g per liter.

The present methods are generally described below with reference to a FIG. 1 through FIG. 7.

Figure 1:
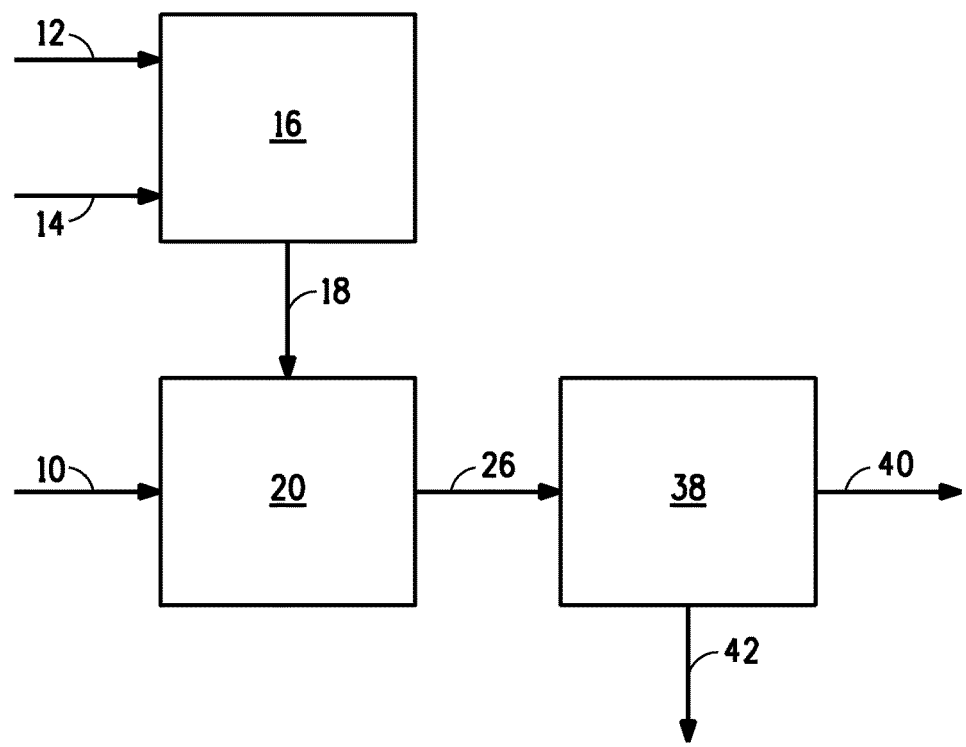

Referring now to FIG. 1, there is shown a schematic representation of one embodiment of processes for producing and recovering butanol using in situ extractive fermentation. An aqueous stream 10 of at least one fermentable carbon source is introduced into a fermentor 20, which contains at least one recombinant microorganism (not shown) capable of converting the at least one fermentable carbon source into butanol. A stream of a first solvent 12 and a stream of an optional second solvent 14 are introduced to a vessel 16, in which the solvents are combined to form the extractant 18. A stream of the extractant 18 is introduced into the fermentor 20, in which contacting of the fermentation medium with the extractant to form a two-phase mixture comprising an aqueous phase and a butanol-containing organic phase occurs. A stream 26 comprising both the aqueous and organic phases is introduced into a vessel 38, in which separation of the aqueous and organic phases is performed to produce a butanol-containing organic phase 40 and an aqueous phase 42.

Figure 2:
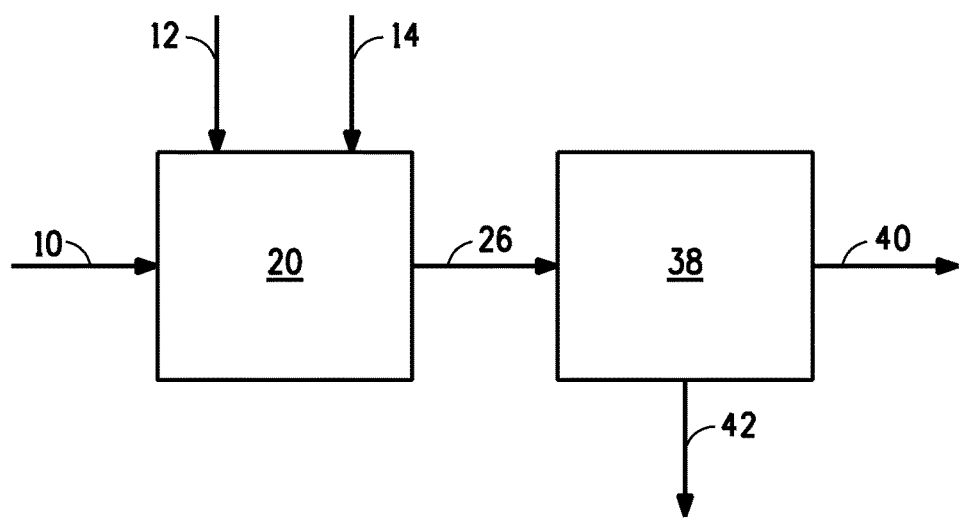

Referring now to FIG. 2, there is shown a schematic representation of one embodiment of processes for producing and recovering butanol using in situ extractive fermentation. An aqueous stream 10 of at least one fermentable carbon source is introduced into a fermentor 20, which contains at least one recombinant microorganism (not shown) capable of converting the at least one fermentable carbon source into butanol. A stream of the first solvent 12 and a stream of the optional second solvent 14 of which the extractant is comprised are introduced separately to the fermentor 20, in which contacting of the fermentation medium with the extractant to form a two-phase mixture comprising an aqueous phase and a butanol-containing organic phase occurs. A stream 26 comprising both the aqueous and organic phases is introduced into a vessel 38, in which separation of the aqueous and organic phases is performed to produce a butanol-containing organic phase 40 and an aqueous phase 42.

Figure 3:
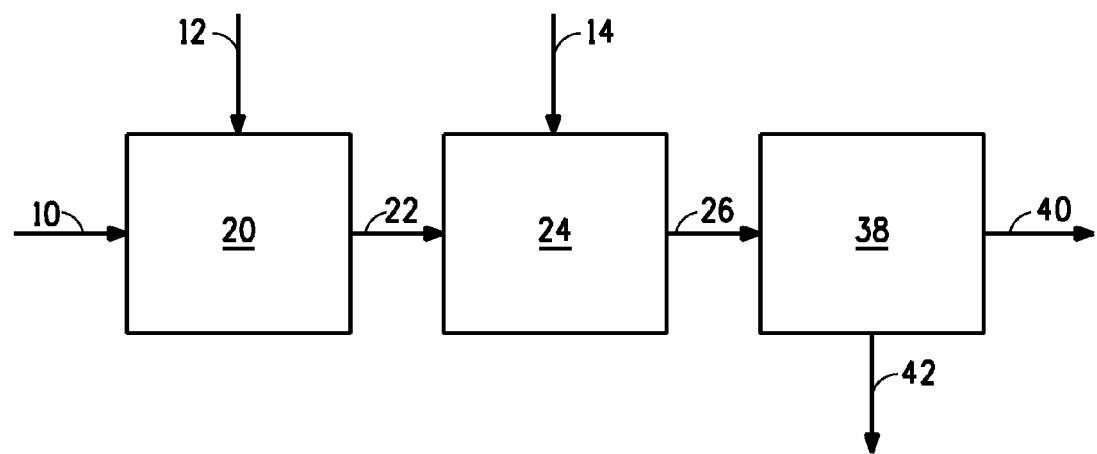

Referring now to FIG. 3, there is shown a schematic representation of one embodiment of processes for producing and recovering butanol using in situ extractive fermentation. An aqueous stream 10 of at least one fermentable carbon source is introduced into a first fermentor 20, which contains at least one recombinant microorganism (not shown) capable of converting the at least one fermentable carbon source into butanol. A stream of the first solvent 12 of which the extractant is comprised is introduced to the fermentor 20, and a stream 22 comprising a mixture of the first solvent and the contents of fermentor 20 is introduced into a second fermentor 24. A stream of the optional second solvent 14 of which the extractant is comprised is introduced into the second fermentor 24, in which contacting of the fermentation medium with the extractant to form a two-phase mixture comprising an aqueous phase and a butanol-containing organic phase occurs. A stream 26 comprising both the aqueous and organic phases is introduced into a vessel 38, in which separation of the aqueous and organic phases is performed to produce a butanol-containing organic phase 40 and an aqueous phase 42.

Figure 4:
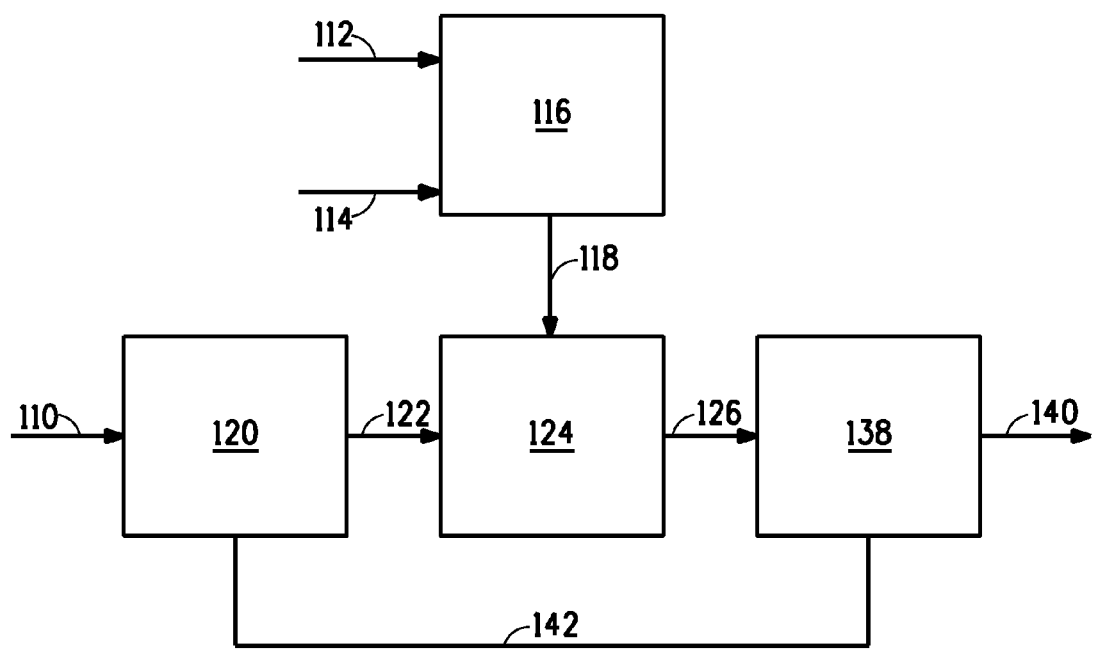

Referring now to FIG. 4, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one recombinant microorganism (not shown) capable of converting the at least one fermentable carbon source into butanol. A stream of the first solvent 112 and a stream of the optional second solvent 114 are introduced to a vessel 116, in which the solvents are combined to form the extractant 118. At least a portion, shown as stream 122, of the fermentation medium in fermentor 120 is introduced into vessel 124. A stream of the extractant 118 is also introduced into vessel 124, in which contacting of the fermentation medium with the extractant to form a two-phase mixture comprising an aqueous phase and a butanol-containing organic phase occurs. A stream 126 comprising both the aqueous and organic phases is introduced into a vessel 138, in which separation of the aqueous and organic phases is performed to produce a butanol-containing organic phase 140 and an aqueous phase 142.

Figure 5:
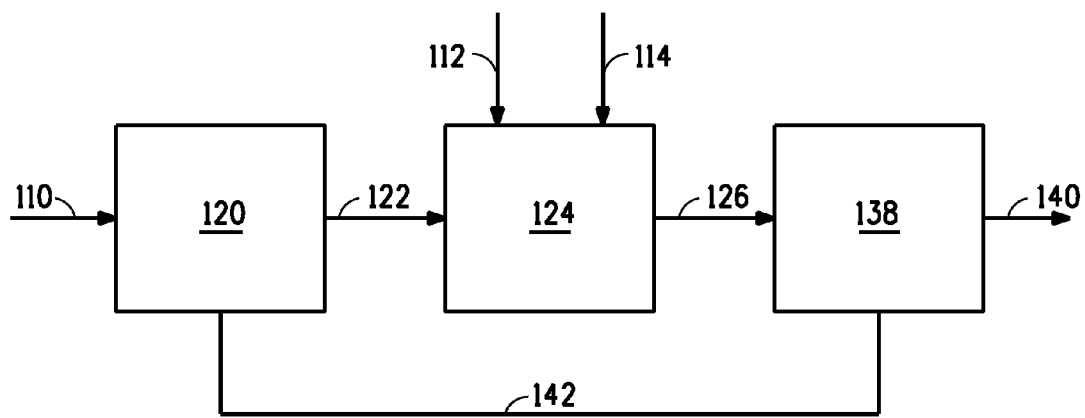

Referring now to FIG. 5, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one recombinant microorganism (not shown) capable of converting the at least one fermentable carbon source into butanol. A stream of the first solvent 112 and a stream of the optional second solvent 114 of which the extractant is comprised are introduced separately to a vessel 124, in which the solvents are combined to form the extractant. At least a portion, shown as stream 122, of the fermentation medium in fermentor 120 is also introduced into vessel 124, in which contacting of the fermentation medium with the extractant to form a two-phase mixture comprising an aqueous phase and a butanol-containing organic phase occurs. A stream 126 comprising both the aqueous and organic phases is introduced into a vessel 138, in which separation of the aqueous and organic phases is performed to produce a butanol-containing organic phase 140 and an aqueous phase 142.

Figure 6:
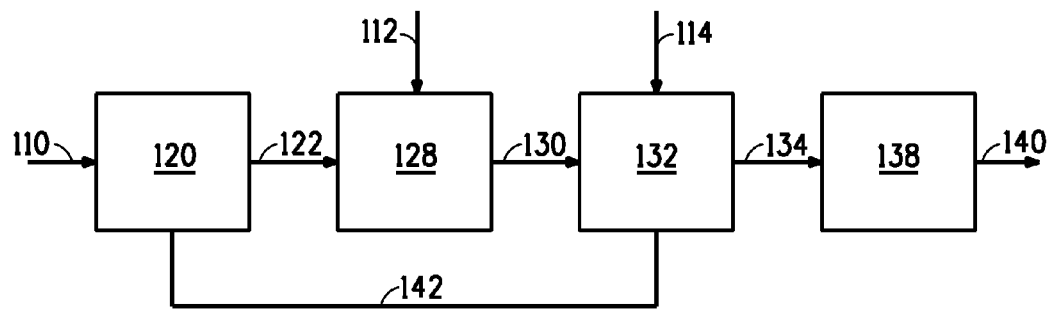

Referring now to FIG. 6, there is shown a schematic representation of one embodiment of processes for producing and recovering butanol in which extraction of the product is performed downstream of the fermentor, rather than in situ. An aqueous stream 110 of at least one fermentable carbon source is introduced into a fermentor 120, which contains at least one recombinant microorganism (not shown) capable of converting the at least one fermentable carbon source into butanol. A stream of the first solvent 112 of which the extractant is comprised is introduced to a vessel 128, and at least a portion, shown as stream 122, of the fermentation medium in fermentor 120 is also introduced into vessel 128. A stream 130 comprising a mixture of the first solvent and the contents of fermentor 120 is introduced into a second vessel 132. A stream of the optional second solvent 114 of which the extractant is comprised is introduced into the second vessel 132, in which contacting of the fermentation medium with the extractant to form a two-phase mixture comprising an aqueous phase and a butanol-containing organic phase occurs. A stream 134 comprising both the aqueous and organic phases is introduced into a vessel 138, in which separation of the aqueous and organic phases is performed to produce a butanol-containing organic phase 140 and an aqueous phase 142.

The extractive processes described herein can be run as batch processes or can be run in a continuous mode where fresh extractant is added and used extractant is pumped out such that the amount of extractant in the fermentor remains constant during the entire fermentation process. Such continuous extraction of products and byproducts from the fermentation can increase effective rate, titer and yield.

Figure 7:
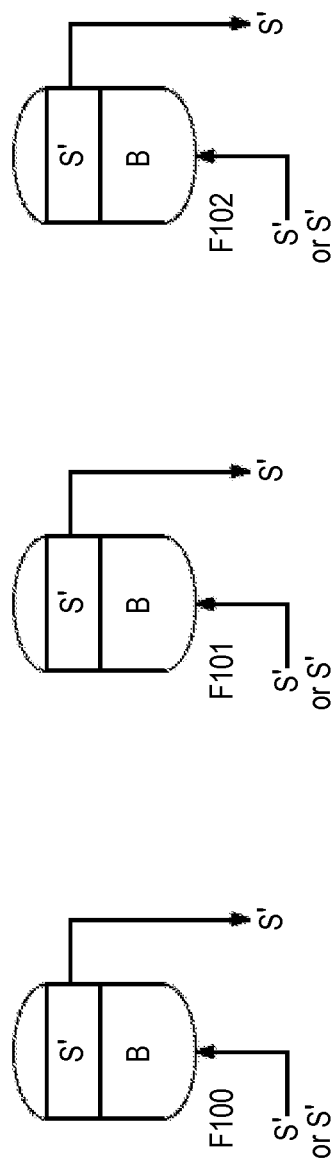

In yet another embodiment, it is also possible to operate the liquid-liquid extraction in a flexible co-current or, alternatively, counter-current way that accounts for the difference in batch operating profiles when a series of batch fermentors are used. In this scenario the fermentors are filled with fermentable mash which provides at least one fermentable carbon source and recombinant microorganism in a continuous fashion one after another for as long as the plant is operating. Referring to FIG. 7, once Fermentor F100 fills with mash and microorganism, the mash and microorganism feeds advance to Fermentor F101 and then to Fermentor F102 and then back to Fermentor F100 in a continuous loop. The fermentation in any one fermentor begins once mash and microorganism are present together and continues until the fermentation is complete. The mash and microorganism fill time equals the number of fermentors divided by the total cycle time (fill, ferment, empty and clean). If the total cycle time is 60 hours and there are 3 fermentors then the fill time is 20 hours. If the total cycle time is 60 hours and there are 4 fermentors then the fill time is 15 hours.

Adaptive co-current extraction follows the fermentation profile assuming the fermentor operating at the higher broth phase titer can utilize the extracting solvent stream richest in butanol concentration and the fermentor operating at the lowest broth phase titer will benefit from the extracting solvent stream leanest in butanol concentration. For example, referring again to FIG. 7, consider the case where Fermentor F100 is at the start of a fermentation and operating at relatively low butanol broth phase (B) titer, Fermentor F101 is in the middle of a fermentation operating at relatively moderate butanol broth phase titer and Fermentor F102 is near the end of a fermentation operating at relatively high butanol broth phase titer. In this case, lean extracting solvent (S), with minimal or no extracted butanol, can be fed to Fermentor F100, the "solvent out" stream (S') from Fermentor F100 having an extracted butanol component can then be fed to Fermentor F101 as its "solvent in" stream and the solvent out stream from F101 can then be fed to Fermentor F102 as its solvent in stream. The solvent out stream from F102 can then be sent to be processed to recover the butanol present in the stream. The processed solvent stream from which most of the butanol is removed can be returned to the system as lean extracting solvent and would be the solvent in feed to Fermentor F100 above.

As the fermentations proceed in an orderly fashion the valves in the extracting solvent manifold can be repositioned to feed the leanest extracting solvent to the fermentor operating at the lowest butanol broth phase titer. For example, assume (a) Fermentor F102 completes its fermentation and has been reloaded and fermentation begins anew, (b) Fermentor F100 is in the middle of its fermentation operating at moderate butanol broth phase titer and (c) Fermentor F101 is near the end of its fermentation operating at relatively higher butanol broth phase titer. In this scenario the leanest extracting solvent would feed F102, the extracting solvent leaving F102 would feed Fermentor F100 and the extracting solvent leaving Fermentor F100 would feed Fermentor F101.

The advantage of operating this way can be to maintain the broth phase butanol titer as low as possible for as long as possible to realize improvements in productivity. Additionally, it can be possible to drop the temperature in the other fermentors that have progressed further into fermentation that are operating at higher butanol broth phase titers. The drop in temperature can allow for improved tolerance to the higher butanol broth phase titers.

Advantages of the Present Methods

The present extractive fermentation methods provide butanol known to have an energy content similar to that of gasoline and which can be blended with any fossil fuel. Butanol is favored as a fuel or fuel additive as it yields only $CO_2$ and little or no $SO_x$ or $NO_x$ when burned in the standard internal combustion engine. Additionally, butanol is less corrosive than ethanol, the most preferred fuel additive to date.

In addition to its utility as a biofuel or fuel additive, the butanol produced according to the present methods has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or vehicles. Furthermore, the present methods produce butanol from plant derived carbon sources, avoiding the negative environmental impact associated with standard petrochemical processes for butanol production.

One of the advantages of the present methods is the higher butanol partition coefficient compared to solvents used in the art. Combinations of solvents obtained by the appropriate combination of a first and a second solvent as described herein, can provide extractants having a higher partition coefficient. Extractants having higher partition coefficients can provide more effective extraction of butanol from the fermentation medium. Another advantage of the present method is the ability to use a solvent which has a desirably higher partition coefficient but undesirably lower biocompatibility, and to mitigate the lower biocompatibility by the combination with a solvent having higher biocompatibility. As a result, a more effective extractant is obtained, an extractant which can be used in the presence of the microorganism with continued viability of the microorganism.

Further advantages of the present methods include the improved process operability characteristics of the extractant relative to those characteristics of oleyl alcohol. The extractant of the present methods has lower viscosity, lower density, and lower boiling point than oleyl alcohol, which provides improvements to the extraction process using such an extractant. Improved viscosity and density of the extractant can lead to improved efficiency of extraction and ease of phase separation. A lower boiling point can reduce the energy required for distillative separations, reduce the energy for removing the extractant from DDGS (dried distiller's grains with solubles), and can lower the bottoms temperatures in a distillation column separating the butanol from the extractant. Together these characteristics can provide an economic advantage for extractive fermentation using an extractant as disclosed herein.

Confirmation of Isobutanol Production

The presence and/or concentration of isobutanol in the culture medium can be determined by a number of methods known in the art (see, for example, U.S. Pat. No. 7,851,188, incorporated by reference). For example, a specific high performance liquid chromatography (HPLC) method utilizes a Shodex SH-1011 column with a Shodex SHG guard column, both may be purchased from Waters Corporation (Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol has a retention time of 46.6 min under the conditions used.

Alternatively, gas chromatography (GC) methods are available. For example, a specific GC method utilizes an HP-INNOWax column (30 m×0.53 mm id, 1 μm film thickness, Agilent Technologies, Wilmington, Del.), with a flame ionization detector (FID). The carrier gas is helium at a flow rate of 4.5 mL/min, measured at 150° C. with constant head pressure; injector split is 1:25 at 200° C.; oven temperature is 45° C. for 1 min, 45 to 220° C. at 10° C./min, and 220° C. for 5 min; and FID detection is employed at 240° C. with 26 mL/min helium makeup gas. The retention time of isobutanol is 4.5 min.

While various embodiments of the present invention have been described herein, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of those skilled in the art to which this invention pertains, and are herein incorporated by reference to the same extent as if each individual publication, patent, or patent application was specifically and individually indicated to be incorporated by reference.

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Materials

The following materials were used in the examples. All commercial reagents were used as received.

All solvents were obtained from Sigma-Aldrich (St. Louis, Mo.) and were used without further purification. The oleyl alcohol used was technical grade, which contained a mixture of oleyl alcohol (65%) and higher and lower fatty alcohols. The purity of the other solvents used was as follows: 1-nonanol, 98%; 1-decanol, 98%; 1-undecanol, 98%; 2-undecanol, 98%; dodecanol, 98%; 1-nonanal, 98%. Isobutanol (purity 99.5%) was obtained from Sigma-Aldrich and was used without further purification.

Growth Protocols

Primary and Secondary Screen Growth Protocol

Minimal Media: 6.7 g Yeast nitrogen base without amino acids; 1.4 g Yeast synthetic drop-out medium without histidine, leucine, tryptophan, uracil; 2 g/L D-(+)-Glucose; 10 ml 1% Leucine stock; 2 mL 1% Tryptophan stock; 2 mL Ethyl Alcohol; make up to 1 L with DI water and filter sterilize.

Rich Media: The following was added to 3.0 L warm deionized water: 6.7 g/L Yeast nitrogen base w/o amino acids; 30 g/L dextrose (glucose); 6.3 mL/L ethanol, anhydrous (200 proof); 4.0 g/L peptone, Bacto; 2.0 g/L yeast extract, Difco; 38.4 g/L MES Buffer (0.2 M); 3.7 g/L ForMedium (2×); or 2.8 g/L yeast dropout mix (Sigma Y2001); 20 mL/L of 10 g/L leucine solution; 4.0 mL/L of 10 g/L tryptophan solution. 2 L warm DI water gently heated; components mixed until dissolved; cooled to room temperature; titrated to pH 5.8 using 2M NaOH; brought up to 3.0 L; final pH measured; and solution filter sterilized in sterile filter apparatus.

To grow the cells, one working stock of cells was thawed on ice for 30 minutes. 50 mL of minimial media were warmed in a 250 mL autoclaved flask at 30° C. 400 uL of thawed working stock was inoculated into 50 mL minimal media (at 30° C.). The resulting culture was incubated for 72 hr at 30° C., 250 rpm. The extraction flask was prepared by adding 300 mL of rich media and 100 mL of sterile filtered Oleyl alcohol to 2 L polycarbonate flask and warming to 30° C. 300 mL of rich media were measured and autoclaved in a graduated cylinder. 100 mL of sterile filtered oleyl alcohol was measured out with serological pipette. 30 mL of the 24 hr minimal media culture was inoculated in an extraction flask. The culture was incubated for 48 hrs at 30° C., 200 rpm.

To prepare the cells for a pre-run, from 48 hr 2 L extraction flask, 40 mL were aliquoted into 10×50 mL conical tubes. The conical tubes were centrifuged for 10 minutes at 4° C. at 19000 RPMs. The supernatant was decanted by pouring and the pellet was resuspended in 10 mL of rich media. The resuspension was distributed evenly into 4 conical tubes as follows: 3 conicals @10 mL each into 1 conical (total volume 30 mL)×2; 2 conicals @10 mL each into 1 conical (total volume 20 mL)×2. The conical tubes were centrifuged for 10 min at 4° C. at 19000 RPMs. The supernatant was decanted by pouring and the pellet was resuspended in each of the 4 conicals to a final volume of 25 mL using rich media. The conical tubes were centrifuged, decanted, and resuspended again to a final volume of 25 mL using rich media. A sterilized 500 mL Erlenmeyer flask was prepared by adding 250 mL of rich media. The resuspended cells from the 4 conicals were added into the flask so that the final volume of the cells in flask is 350 mL.

To run the time course, 25 mL from the 350 mL of re-suspended cells was aliquoted into 12×125 mL Erlenmeyer flasks. To each 125 mL erlenmeyer flask with 25 mL of cells, 25 mL of solvent was added. The flasks were incubated at 30° C., shaking at 250 RPMs for 24 hrs. Time points were taken at 4 hr and 24 hr.

For each time point, the cells were prepared as follows: the flasks were allowed to sit at rest for 1 minute. From each flask 3 fractions of 1 mL samples were aliquoted into 1.5 mL microfuge tubes, as follows: (a) 1 mL organic layer (analytical: iBuOH, EtOH); (b) 1 mL aqueous layer (analytical: glucose, iBuOH, EtOH); (c) 1 mL aqueous layer (Cellometer viability, $OD_{600}$).

For fractions a) and b) analytical samples were prepared by sterile filtering through a 0.22 um nylon filter Costar Spin-x microfuge tube filter (Spin-x); the tubes were centrifuged for 5 min at 13,000 RPM, 4° C. to separate aqueous and organic layers; 500 uL of the organic layer was carefully aspirated from fraction a) into a Spin-x; 500 uL of aqueous layer was carefully aspirated from fraction b) into a Spin-x; the sample was spun at 13,000 RPM for 5 min, 4° C.; and the resulting filtrate was considered organism free and submitted for analysis for glucose, iBuOH, EtOH.

For fraction c), the cells were washed in PBS pH 7.4 buffer before assessing viability and OD600; the tubes were centrifuged for 5 min at 13,000 RPM, 4° C. to pellet cells' the supernatant was decanted immediately and resuspend in 1 mL of PBS by vortexing; the tubes were centrifuged again for 5 min at 13,000 RPM, 4° C.; the supernatant was decanted immediately and resuspend in 1 mL of PBS pH 7.4 buffer; the tubes were centrifuged again for 5 min at 13,000 RPM, 4° C.; the supernatant was decanted immediately and resuspend in 1 mL of PBS pH 7.4 buffer. The re-suspended samples were kept on ice, at 4° C. until ready to read on Cellometer. After Cellometer reads, dilutions were made for $OD_{600}$, blank with PBS.

To assess cell viability on Cellometer, each sample was diluted Nexcelom yeast dilution buffer 5× (10:40 uL:sample:buffer). 2× dilution to 20× dilution can be appropriate depending on cell concentration. The resulting mixture was allowed to incubate for 1 minute. The sample was diluted into AOPI live-dead stain dye 4× (10:30 uL:sample:dye). The resulting mixture was allowed to incubate at RT for 1 minute. 20 uL of the resulting mixture was loaded into the disposable Nexcelom slide. Using this assay, cells were counted and recorded (F1 (Fluorescein) exposure: 1200 ms; F2 (Propidium Iodide) exposure: 4000 ms).

Tertiary Screen Growth Protocol

Minimal media: 6.7 g Yeast nitrogen base without amino acids; 1.4 g yeast synthetic drop-out medium without histidine, leucine, tryptophan, uracil; 2 g/L D-(+)-glucose; 10 ml 1% leucine stock; 2 mL 1% tryptophan stock; 2 mL ethyl alcohol; made up to 1 L with DI water and filter sterilized.

Rich media: The following was added to 3.0 L warm deionized water: 6.7 g/L yeast nitrogen base w/o amino acids; 30 g/L dextrose (glucose); 6.3 mL/L ethanol, anhydrous (200 proof); 4.0 g/L peptone, Bacto; 2.0 g/L yeast extract, Difco; 38.4 g/L MES Buffer (0.2 M); 3.7 g/L ForMedium (2×); or 2.8 g/L yeast dropout mix (Sigma Y2001); 20 mL/L of 10 g/L leucine solution; 4.0 mL/L of 10 g/L tryptophan solution. 2 L warm DI water gently heated; components mixed until dissolved; cooled to room temperature; titrated to pH 5.8 using 2M NaOH; brought up to 3.0 L; final pH measured; and solution filter sterilized in sterile filter apparatus.

To grow the cells, 1 master stock vial from −80 C was thawed on ice (or at 4° C.) for 30 minutes. To 2×250 mL sterile Erlenmeyer flasks, 50 mL minimal media was added. The resulting media was warmed in flasks to 30° C. 400 uL of master stock was added into each 250 mL flask and incubated at 30° C., 250 RPM, for 3-5 days.

To prepare the solvent and cells for pre-run, 12.5 mL of each solvent (2 control+max 6 candidates) was measured into 100 mL glass graduated cylinders in duplicate. 70 mL of minimal media culture was inoculated into 700 mL of rich media at room temperature. 37.5 mL of the inoculated rich media cell broth was aliquoted into each 250 mL flask. 1 mL of the left over inoculated rich media cell broth was aliquoted and stored at 4° C.: the O.D., cell concentration, and cell viability (Cellometer) were recorded after starting the run. The rich media was not allowed to sit at room temperature without solvent for longer than 30 minutes.

To run the time course, 12.5 mL of pre-measured solvent was combined with 37.5 mL of inoculated rich media for each solvent in duplicate. Oleyl Alcohol and 2-ethyl-1-hexanol were used as control solvents. The solvent and inoculated rich media were incubated at 30° C., 200 RPM for a 72 hr time course, taking time points every 24 hr.

For each time point, the cells were prepared as follows: the flasks were allowed to sit at rest for 1 minute. From each flask 3 fractions of 1 mL samples were aliquoted into 1.5 mL microfuge tubes as follows: (a) 1 mL organic layer (analytical: iBuOH, EtOH); (b) 1 mL aqueous layer (analytical: glucose, iBuOH, EtOH); and (c) 1 mL aqueous layer (Cellometer viability, $OD_{600}$).

For fractions a) and b) analytical samples were prepared by sterile filtering through a 0.22 um nylon filter Costar Spin-x microfuge tube filter (Spin-x). The tubes were centrifuged 5 min at 13,000 RPM, 4° C. to separate aqueous and organic layers. 500 uL of the organic layer was carefully aspirated from fraction (a) into a Spin-x; 500 uL of the aqueous layer was carefully aspirated from fraction (b) into a Spin-x; the samples were spun in filled Spin-x tubes at 13,000 RPM for 5 min, 4° C.; and the resulting filtrate was considered "stopped" and organism free. These samples were submitted for analysis of glucose, iBuOH, and EtOH.

For fraction c), the cells were washed in PBS pH 7.4 buffer before assessing viability and OD600. the tubes were centrifuged for 5 min at 13,000 RPM, 4° C. to pellet cells' the supernatant was decanted immediately and resuspend in 1 mL of PBS by vortexing; the tubes were centrifuged again for 5 min at 13,000 RPM, 4° C.; the supernatant was decanted immediately and resuspend in 1 mL of PBS pH 7.4 buffer; the tubes were centrifuged again for 5 min at 13,000 RPM, 4° C.; the supernatant was decanted immediately and resuspend in 1 mL of PBS pH 7.4 buffer. The re-suspended samples were kept on ice, at 4° C. until ready to read on Cellometer. After Cellometer reads, dilutions were made for $OD_{600}$, blank with PBS.

To assess cell viability on Cellometer, each sample was diluted Nexcelom yeast dilution buffer 5× (10:40 uL:sample: buffer). 2× dilution to 20× dilution can be appropriate depending on cell concentration. The resulting mixture was allowed to incubate for 1 minute. The sample was diluted into AOPI live-dead stain dye 4× (10:30 uL:sample:dye). The resulting mixture was allowed to incubate at RT for 1 minute. 20 uL of the resulting mixture was loaded into the disposable Nexcelom slide. Using this assay, cells were counted and recorded (F1 (Fluorescein) exposure: 1200 ms; F2 (Propidium Iodide) exposure: 4000 ms).

Example 1

Identification of Biocompatible Solvents Capable of Isobutanol Extraction Using a Three Stage Screening Process Solvent extraction methods were investigated to support the in situ product recovery (ISPR) process for isobutanol (iBuOH) production and assist in reducing operating costs. Economical, technically efficient, biocompatible solvents were sought. To support this activity, a list of solvents of varied chemical character was compiled to identify a biocompatible solvent that could not be predicted a priori from published physical characteristics. The solvents were screened for biocompatibility and extractability. The following constraints were considered in identifying the solvents to test experimentally: (a) the solvent is minimally soluble/insoluble in water to improve recovery of isobutanol; (b) the boiling point of the solvent is different from isobutanol (74° C.) for ease in distillation; (c) the boiling point of the solvent is less than 250° C. to facilitate removal of the solvent from dried distillers grains (DDGS); (d) the melting point of the solvent is less than 10° C. to avoid handling problems; (e) the density of the solvent is different from water to aid in phase separation; (f) the Hildebrand solubility parameter is similar to isobutanol (22.7 $MPa^{0.5}$); and (g) the solvent is commercially available. The solvents that were tested are shown in Table 1.

TABLE 1

List of solvents experimentally screened.

| Solvent name | CAS no. | Boiling point (° C.) |
| --- | --- | --- |
| oleyl alcohol | 143-28-2 | 333 |
| n-decane | 124-18-5 | 174 |
| methyl laurate | 111-82-0 | 260 |
| di-n-hexyl ether | 112-58-3 | 223 |
| decalin | 91-17-8 | 187 |
| 2-ethyl hexyl acetate | 103-09-3 | 199 |
| 2-ethylhexylglycol ether | 1559-35-9 | 228 |
| 2-ethyl-1-hexanol | 104-76-7 | 184 |
| 2,6-dimethylheptan-4-ol | 108-82-7 | 178 |
| ethyl n-butyrate | 105-54-4 | 120 |
| n-hexyl acetate | 142-92-7 | 168 |
| 1,2-dibutoxyethane | 112-48-1 | 203 |
| n-butyl n-butyrate | 109-21-7 | 166 |
| 2,6-dimethylheptan-4-one | 108-83-8 | 169 |
| ETBE | 637-92-3 | 70 |
| di-n-butyl ether | 142-96-1 | 142 |
| ethylene glycol monohexyl ether | 112-25-4 | 206 |
| MTBE | 1634-04-4 | 55 |
| propylene glycol methyl ether acetate | 108-65-6 | 146 |
| isooctane | 540-84-1 | 99 |
| mesitylene | 108-67-8 | 165 |
| acetophenone | 98-86-2 | 202 |
| n-hexanol | 111-27-3 | 157 |
| phenyl acetate | 122-79-2 | 196 |
| 1-octanol | 111-87-5 | 194 |
| 8-methylquinoline | 611-32-5 | 247 |
| p-tolualdehyde | 104-87-0 | 207 |
| 2-octanol | 123-96-6 | 180 |
| isophorone | 78-59-1 | 215 |
| methyl isobutyl carbinol | 108-11-2 | 132 |
| o-xylene | 95-47-6 | 144 |
| trimethylnonanol | 123-17-1 | 225 |
| n-butyl propionate | 590-01-2 | 145 |
| n-propyl propionate | 106-36-5 | 122 |
| n-butyl acetate | 123-86-4 | 126 |
| n-pentyl propionate | 624-54-4 | 165 |

TABLE 1-continued

List of solvents experimentally screened.

| Solvent name | CAS no. | Boiling point (° C.) |
|---|---|---|
| primary amyl acetate mixed isomers | 628-63-7 | 149 |
| isobutyl acetate | 110-19-0 | 118 |
| dodecanal | 112-54-9 | 241 |
| UCAR filmer IBT | 25265-77-4 | 255 |
| n-butyl valerate | 591-68-4 | 187 |
| di-n-octyl ether | 629-82-3 | 287 |
| isobutyl heptyl ketone | 123-18-2 | 217 |
| dodecane | 112-40-3 | 218 |
| n-undecane | 1120-21-4 | 196 |
| dodecanol | 112-53-8 | 262 |
| ethyl octanoate | 106-32-1 | 208 |
| ethyl decanoate | 110-38-3 | 245 |
| ethyl laurate | 106-33-2 | 269 |
| methyl decanoate | 110-42-9 | 224 |
| methyl hexanoate | 106-70-7 | 151 |
| methyl heptanoate | 106-73-0 | 172 |

Screening Strategy

Based on growth protocols described above, a strategy was devised with a multi-stage screening process to optimize throughput, resource usage, and information content. From the protocols it was determined that a two-stage media process was required for the isobutanologen. The first stage was a minimal media stage deficient in uracil and leucine and low in glucose followed by the second stage which was a rich media stage high in glucose content that was conducive to isobutanol production in the presence of a biocompatible solvent (e.g., oleyl alcohol).

Figure 8:
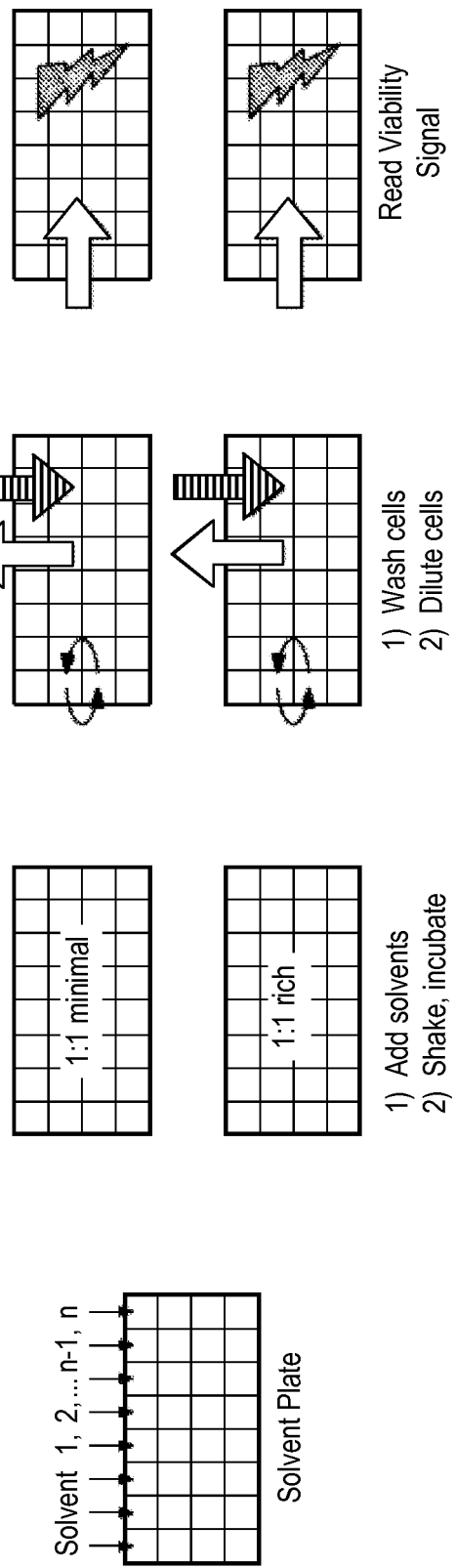
FIG. 8 is a schematic work flow diagram for an automated primary assay for solvent biocompatibility.

For consistency, cells were grown in bulk by shake flask using this two stage process (minimal media followed by rich media and extractant (e.g., oleyl alcohol)) for use in the primary and secondary screening stages. Cells were pelleted by centrifugation, washed with phosphate buffered solution (PBS), and then dispensed in the appropriate vessels (96 well plate for the primary screen, 50 ml total volume for the secondary screen) before exposure to candidate solvents. This treatment was performed to ensure the cells were in a representative metabolic stage before solvent exposure. From the primary screen (discussed in more detail below), viability data was collected by a fluorescence assay for all solvents screened. FIG. 8 illustrates the work flow for the automated primary screen/assay.

Figure 9:
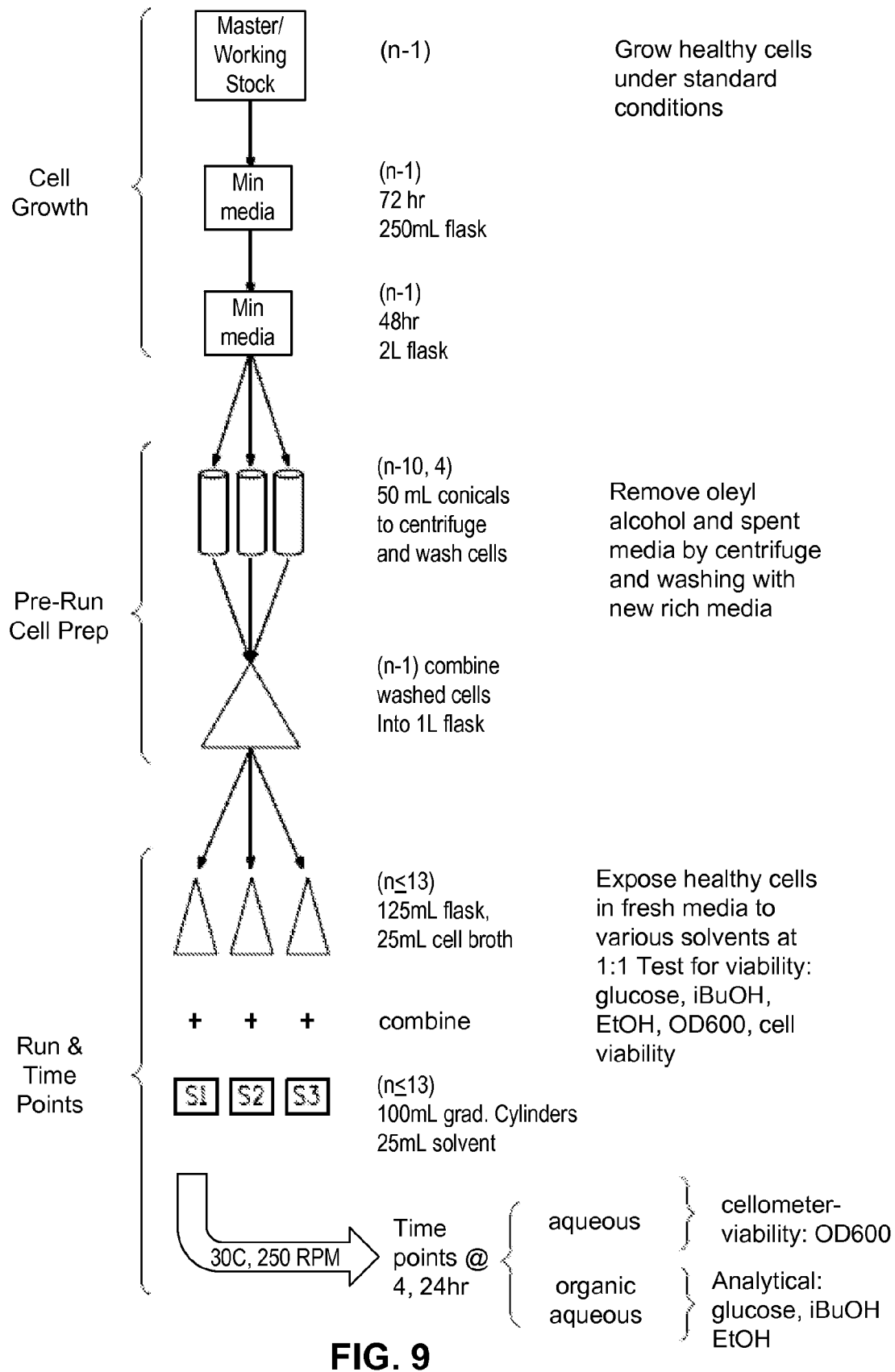
FIG. 9 is a schematic flow diagram for a secondary assay for solvent biocompatibility.

Solvents that passed the primary screen were analyzed by a secondary screen (discussed in more detail below). A work flow diagram illustrating the secondary screen is shown in FIG. 9. From the secondary assay on viable hits identified from the primary screen, two time points were taken from which viability, glucose, ethanol, and isobutanol concentrations were analyzed.

Figure 10:
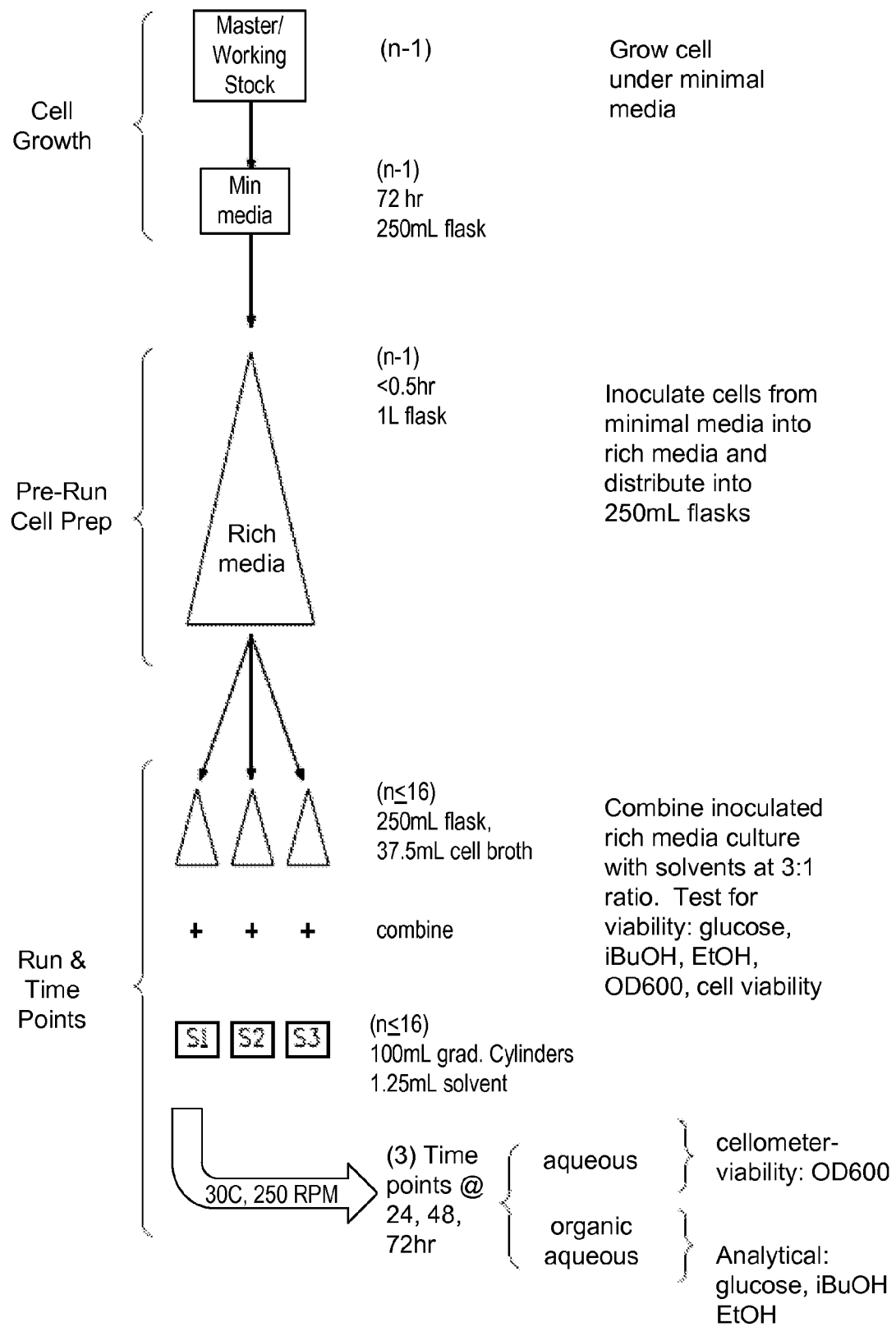
FIG. 10 is a schematic flow diagram for a tertiary assay for solvent biocompatibility.

For the tertiary screen (discussed in more detail below), conditions were modeled that were more representative of a process scenario; i.e., elimination of extractant treatment (e.g., oleyl alcohol) and analysis of samples taken over a time course of at least 48 hours. A work flow diagram illustrating the tertiary screen is shown in FIG. 10. Cells were grown in bulk by shake flask using only minimal media, and then transferred directly to rich media pre-mixed with the reduced number of candidate solvents. The candidate solvents were studied with greater replication (n=3, 50 ml total volume) by reducing the number of candidates that advanced to the tertiary screening level. Key differences between the primary, secondary, and tertiary screens are illustrated in Table 2.

TABLE 2

Summary of key differences at each screening level of the multi-stage process.

| | Total Volume (mL) | Ratio (aq:org) | Exposure time (hr) | Temp (° C.) | Replicates | Data Collected |
|---|---|---|---|---|---|---|
| Primary | 0.15 | 1:1 | 1 | 20 | 4 | Viability |
| Secondary | 50 | 1:1 | 4 or 5; 25 or 30 | 30 | 1 | Viability, isobutanol, glucose, ethanol |
| Tertiary | 50 | 3:1 | 0-48$^+$ time course | 30 | 3 | Viability, isobutanol, glucose, ethanol |

Primary Screen

An automated high throughput assay based on a 96 well plate system was employed for the initial screen to identify solvents that were biocompatible with the isobutanologen. Briefly, the isobutanologen was pre-grown in shake flasks of minimal selection media (low glucose) that were transferred to rich media (high glucose) in the presence of oleyl alcohol. The cells were then plated in a 96 well plate in both minimal selection media (low glucose) and rich media (high glucose) in the presence of the solvent. The cells were then washed to remove the media and solvent and incubated for 1 hour at room temperature with shaking (1000 rpm). After three washes and a two-step dilution, these cells were then treated with fluorescent dye (propidium iodide (PI)) to stain for dead cells. The fluorescent signals were then compared to that from cells treated with oleyl alcohol, which served as the live cell control, and that from cells treated with at a 1:1 ratio of cell broth to 100% ethanol, which served as a dead cell control, to determine biocompatibility. FIG. 8 shows a schematic of the work flow diagram of the automated primary screening assay. Twenty four solvents were identified to be carried forward from primary screening based on viability data obtained (Table 3).

TABLE 3

Solvents identified for secondary screening based on high viability in 96 well plate primary screen.

| Solvent name | Proceed to Secondary Screen | $K_d$ | % Dead |
|---|---|---|---|
| oleyl alcohol | Live Control | 2.23 | -2% |
| n-decane | YES | 0.11 | 3% |
| methyl laurate | YES | 1.12 | -1% |
| di-n-hexyl ether | YES | 0.78 | 7% |
| decalin | YES | 0.13 | 7% |
| 2-ethyl hexyl acetate | YES | 1.88 | 3% |
| 2-ethylhexylglycol ether | NO | 4.95 | 79% |
| 2-ethyl-1-hexanol | Dead Control | 5.51 | 73% |
| 2,6-dimethylheptan-4-ol | YES | 4.25 | 11% |
| ethyl n-butyrate | NO | 3.57 | 42% |
| n-hexyl acetate | YES | 2.23 | 14% |
| 1,2-dibutoxyethane | YES | 2.27 | 5% |
| n-butyl n-butyrate | YES | 2.17 | 13% |
| 2.6-dimethylheptan-4-one | YES | 2.12 | 5% |
| ETBE | YES | 2.47 | 6% |
| di-n-butyl ether | YES | 1.26 | 7% |
| ethylene glycol monohexyl ether | NO | 5.66 | 115% |
| MTBE | YES | 4.18 | 19% |
| propylene glycol methyl ether acetate | NO | 3.15 | 79% |
| isooctane | YES | 0.18 | 8% |
| mesitylene | YES | 0.47 | 11% |
| acetophenone | NO | 2.95 | 73% |
| n-hexanol | NO | 7.41 | 71% |
| phenyl acetate | NO | 1.95 | 51% |

TABLE 3-continued

Solvents identified for secondary screening based on high viability in 96 well plate primary screen.

| Solvent name | Proceed to Secondary Screen | $K_d$ | % Dead |
|---|---|---|---|
| 1-octanol | NO | 5.19 | 90% |
| 8-methylquinoline | YES | 5.03 | 2% |
| p-tolualdehyde | NO | 2.41 | 41% |
| 2-octanol | NO | 5.98 | 33% |
| isophorone | NO | 5.68 | 37% |
| methyl isobutyl carbinol | NO | 7.78 | 71% |
| o-xylene | NO | 0.85 | 55% |
| trimethylnonanol | YES | 3.57 | 3% |
| n-butyl propionate | NO | 3.02 | 45% |
| n-propyl propionate | NO | 3.4 | 105% |
| n-butyl acetate | YES | 3.48 | 0% |
| n-pentyl propionate | NO | 2.94 | 63% |
| primary amyl acetate mixed isomers | NO | 3.67 | 104% |
| isobutyl acetate | NO | 3.33 | 71% |
| dodecanal | YES | 5.38 | 2% |
| UCAR filmer IBT | YES | 4.16 | 39% |
| n-butyl valerate | YES | 2.04 | 8% |
| di-n-octyl ether | YES | 0.55 | 2% |
| isobutyl heptyl ketone | YES | 1.49 | 7% |
| dodecane | YES | 0.18 | 2% |
| n-undecane | YES | 0.20 | 2% |

*UCAR filmer was carried directly to tertiary flasks for testing after screening was completed because it shared structural characteristics in common with confirmed solvents in which isobutanol production was observed.

Favorable Kd values were greater than 1. Unfavorable Kd values were less than 1. Kd values were defined as a concentration of iBuOH in the organic phase/concentration of iBuOH in aqueous phase. The % of dead cells was assessed by propidium iodide signal. The solvent 2-ethyl-1-hexanol was identified as a kill control.

Secondary Screen

The secondary screen was designed to verify the solvents identified in the primary screen under more process relevant conditions. Cells were grown using seed flask protocols in rich media and oleyl alcohol. The cells were then washed and split into aliquots to be treated with the solvents identified in the primary assay. The secondary screen was designed to ensure all the cells began a standard treatment with solvent candidates in optimal conditions. In a 125 mL flask, 25 mL of washed cell broth (oleyl alcohol removed) was exposed to 25 mL of solvent at 30° C. for 4 h and 24 h at 20 rpm. The cell viability was checked by fluorescent PI assay using a Cellometer (Nexcelom Vision, Lawrence, Mass.) to count both live and dead cells. The primary screen had a shorter exposure time (1 hour) at a lower temperature (~22° C., room temperature) as compared to the secondary screen (4 and 24 hours at 30° C.). The schematic for the secondary screen is shown in FIG. 9.

From this screen, fifteen solvents demonstrated strong viability at 4 or 5 hours/30° C. solvent incubation (Table 4). Of the fifteen solvents demonstrating strong viability, only five solvents demonstrated strong viability, isobutanol production and complete glucose consumption at 25 or 30 hours/30° C. (Table 5).

TABLE 4

Secondary screen results for viability in solvents identified in primary screen.

| | 4 Hours | | | 25 Hours | | |
|---|---|---|---|---|---|---|
| Solvent | % Viability | Glucose (g/L) | iBuOH (g/L) | % Viability | Glucose (g/L) | iBuOH (g/L) |
| oleyl alcohol | 100% | 5.7 | 1.8 | 100% | 0.0 | 2.6 |
| n-decane | 107% | 5.8 | 1.6 | 54% | 0.0 | 2.3 |
| methyl laurate | 110% | 3.9 | 2.1 | 94% | 0.0 | 1.6 |
| di-n-hexyl ether | 106% | 8.1 | 1.1 | 62% | 0.9 | 1.9 |
| decalin | 76% | 11.2 | 0.4 | 36% | 10.3 | 0.5 |
| 2-ethyl hexyl acetate | 96% | 10.5 | 0.6 | 42% | 7.1 | 1.2 |
| 2-ethyl-1-hexanol | 14% | 13.1 | 0.0 | 6% | 13.7 | 0.0 |
| 2,6-dimethylheptan-4-ol | 42% | 12.1 | 0.0 | 8% | 11.8 | 0.0 |
| n-hexyl acetate | 18% | 12.8 | 0.0 | 3% | 13.0 | 0.0 |
| 1,2-dibutoxyethane | 63% | 11.9 | 0.4 | 8% | 10.7 | 0.4 |
| n-butyl n-butyrate | 48% | 12.4 | 0.0 | 7% | 11.7 | 0.0 |
| 2.6-dimethylheptan-4-one | 78% | 10.9 | 0.6 | 26% | 7.9 | 0.9 |
| ETBE | 16% | 12.5 | 0.0 | 4% | 12.8 | 0.0 |
| di-n-butyl ether | 90% | 12.4 | 0.1 | 40% | 11.3 | 0.5 |
| MTBE | 5% | 12.7 | 0.0 | 1% | 12.9 | 0.2 |
| isooctane | 90% | 10.8 | 0.5 | 31% | 8.5 | 0.8 |
| mesitylene | 64% | 12.5 | 0.0 | 17% | 12.1 | 0.1 |

% viability was relative to oleyl alcohol and was based on fluorescence based cells counts.

TABLE 5

Secondary screen results for viability for additional solvents.

| | 5 Hours | | | 30 Hours | | |
|---|---|---|---|---|---|---|
| Solvent | % Viability | Glucose (g/L) | iBuOH (g/L) | % Viability | Glucose (g/L) | iBuOH (g/L) |
| oleyl alcohol | 100% | ND | ND | 100% | 0.0 | 2.2 |
| 2-ethyl-1-hexanol | 58% | ND | ND | 47% | 16.8 | 0.0 |
| 8-methylquinoline | ND | ND | ND | 47% | 17.5 | 0.0 |
| trimethylnonanol | 99% | ND | ND | 98% | 0.0 | 2.1 |
| n-butyl acetate | 46% | ND | ND | 35% | 16.6 | 0.0 |

TABLE 5-continued

Secondary screen results for viability for additional solvents.

| | 5 Hours | | | 30 Hours | | |
|---|---|---|---|---|---|---|
| Solvent | % Viability | Glucose (g/L) | iBuOH (g/L) | % Viability | Glucose (g/L) | iBuOH (g/L) |
| dodecanal | 78% | ND | ND | 62% | 0.0 | 0.0 |
| di-n-octyl ether | 99% | ND | ND | 99% | 0.0 | 1.9 |
| isobutyl heptyl ketone | 92% | ND | ND | 56% | 8.9 | 1.7 |
| dodecane | 99% | ND | ND | 99% | 0.0 | 1.9 |
| n-undecane | 98% | ND | ND | 100% | 0.0 | 1.9 |

% viability was relative to oleyl alcohol and was based on fluorescence based cell counts.

Tertiary Screen

The tertiary screen was designed to examine the growth of isobutanologen in the presence of the identified solvents from the primary and secondary screens. The tertiary screen substitutes solvent candidates for oleyl alcohol in a rich media seed protocol. Briefly, a master stock was thawed and inoculated into minimal selection media and grown for 3 days. From the master stock, 1.25 mL of 3-day-old minimal media cell broth was inoculated into a 250 mL flask with 37.5 mL rich media and 12.5 mL solvent candidate (1:3 solvent to broth). Cells were grown at 30° C. and 200 RPM over the course of 72 hours with time points every 24 hours. Viability was checked by Cellometer, glucose consumption was checked at each time point by high pressure liquid chromatography (HPLC), and isobutanol (iBuOH) production was determined by gas chromatography (GC). The schematic for the tertiary screen is shown in FIG. 10.

Figure 11:
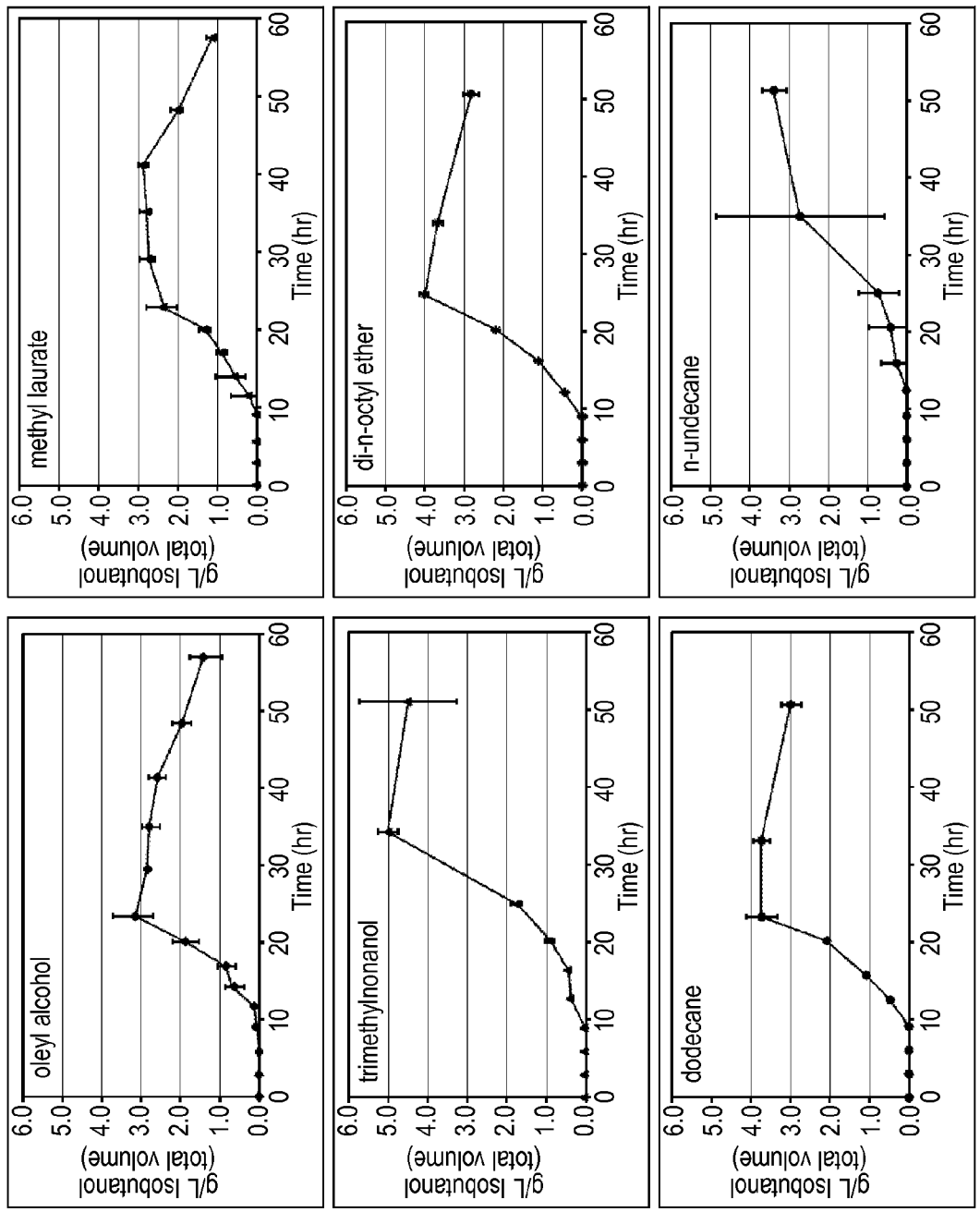
FIG. 11 illustrates the production of isobutanol from an isobutanologen in a tertiary screen for five biocompatible solvents, methyl laurate, trimethylnonanol, di-n-octyl ether, dodecane, and n-undecane using oleyl alcohol as a control (n=3). Error bars denote 95% confidence intervals.
Figure 12:
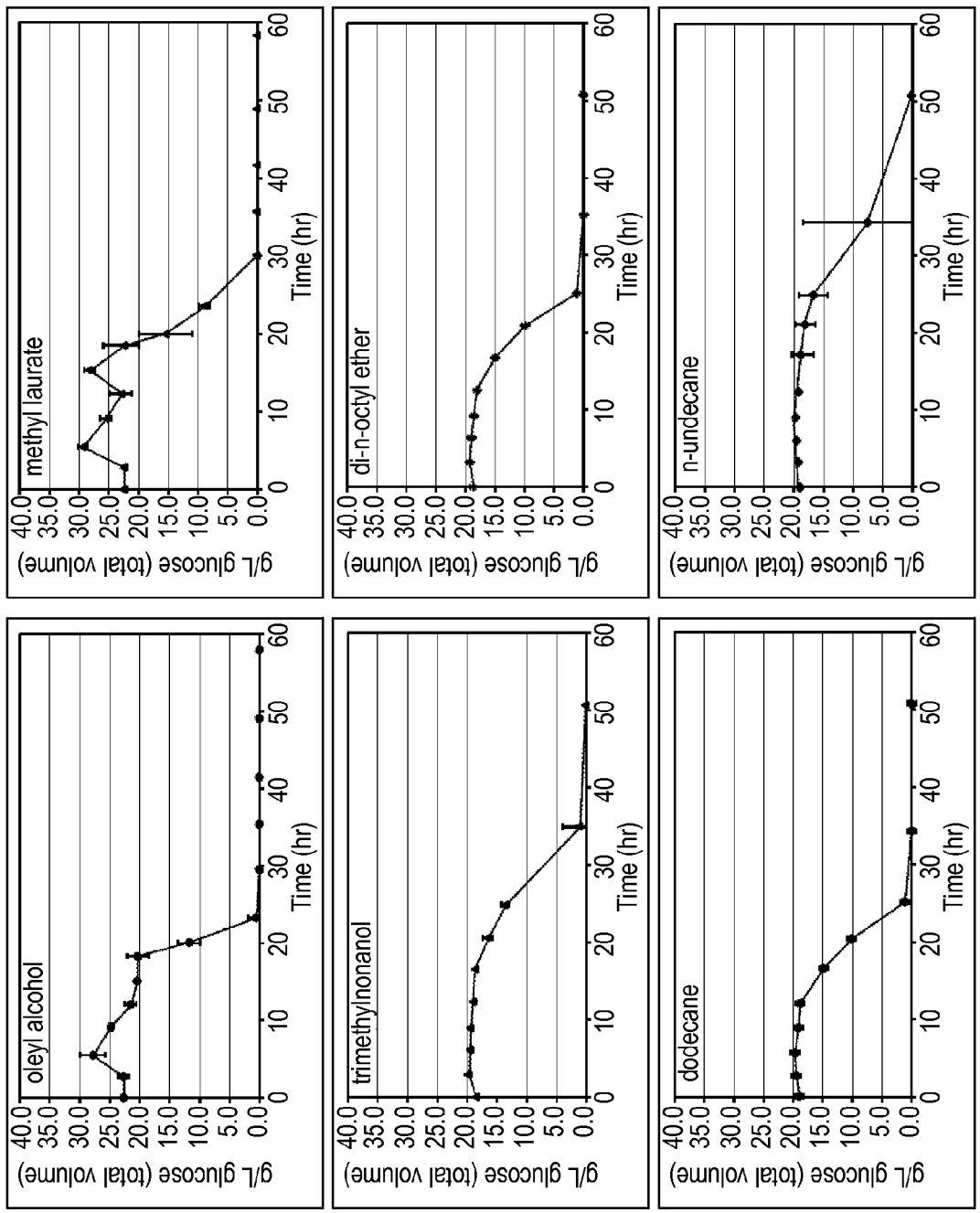
FIG. 12 illustrates the utilization of glucose by an isobutanologen in a tertiary screen for five biocompatible solvents, methyl laurate, trimethylnonanol, di-n-octyl ether, dodecane, and n-undecane using oleyl alcohol as a control (n=3). Error bars denote 95% confidence intervals.
Figure 13:
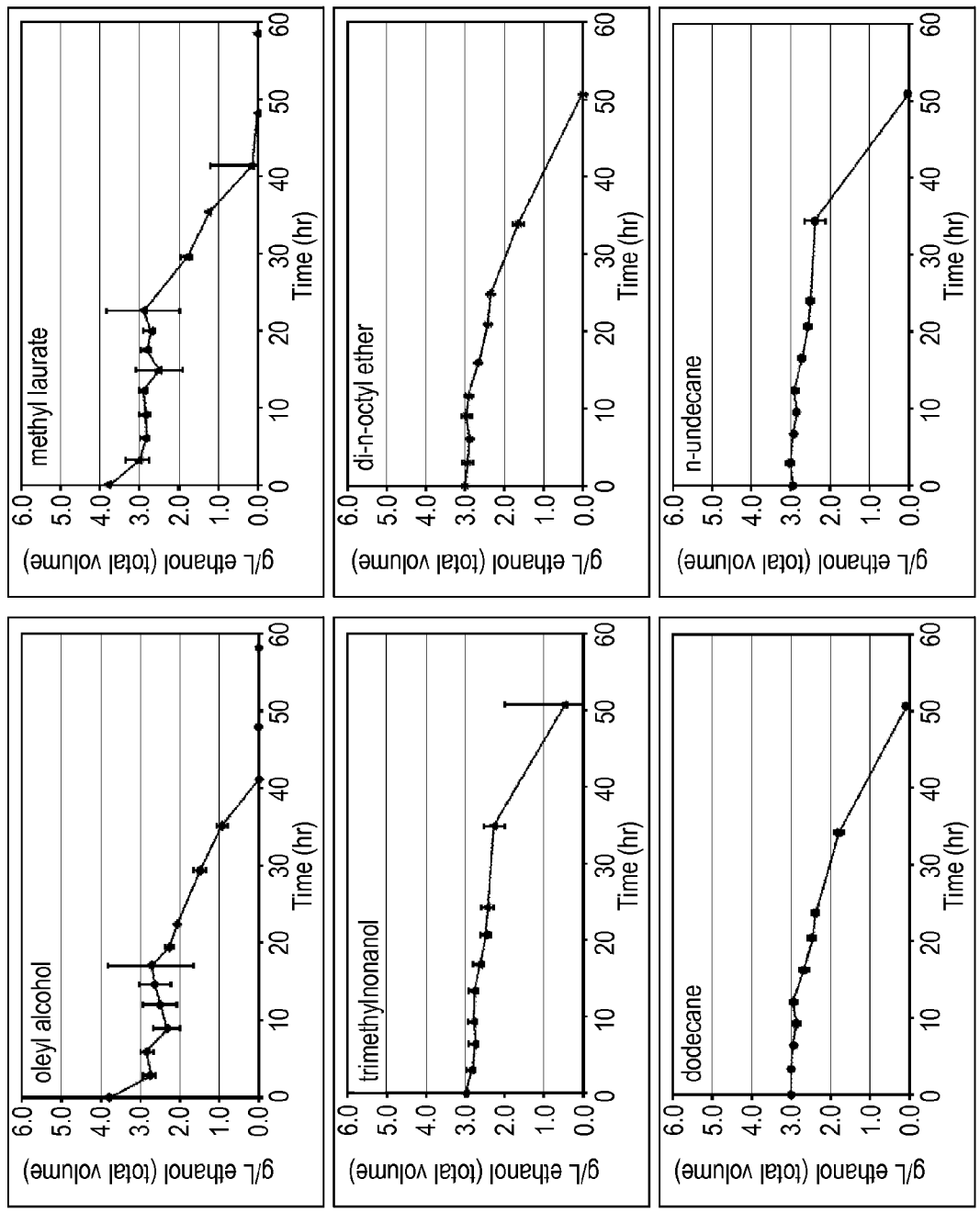
FIG. 13 illustrates the utilization and consumption of ethanol by an isobutanologen in a tertiary screen for five biocompatible solvents, methyl laurate, trimethylnonanol, di-n-octyl ether, dodecane, and n-undecane using oleyl alcohol as a control (n=3). Error bars denote 95% confidence intervals.

All five solvents that demonstrated strong viability, isobutanol production and complete glucose consumption at 25-30 hours in the secondary screen were confirmed in the tertiary screen (Tables 3-5). Solvents that demonstrated weak glucose consumption and isobutanol production at 25-30 hours in the secondary screen were not confirmed in the tertiary screen. Methyl laurate, trimethylnonanol, di-n-octyl ether, dodecane and n-undecane solvent treated cells were observed to produce isobutanol (FIG. 11), consume glucose (FIG. 12) and consume ethanol (FIG. 13) at levels comparable to oleyl alcohol.

During the identification of solvents in the three step screening process described above, it was determined that a majority of the biocompatible solvents possessed more than eleven carbons, boiling points between 196-300° C., and log P values>4. Biocompatible solvents were found amongst the esters, alcohols, ethers and alkanes. Examination of the screened twelve carbon (C12) compounds revealed that dodecanol, dodecanal, and UCAR filmer IBT were toxic, while trimethylnonanol and dodecane were biocompatible. None of the C10 or shorter compounds were biocompatible.

Example 2

Identification of Biocompatible Methyl Laurate Analogs

Based on the solvent analyses by chemical and physical characteristics, a pilot structure-viability analysis of esters based on methyl laurate as a parent compound was performed. Two more biocompatible hits identified by screening related structures to methyl laurate. Ethyl decanoate and ethyl laurate were observed to support similar levels of isobutanol production as methyl laurate (FIG. 18).

TABLE 6

Chart of analogues of methyl laurate.

| Solvent | Structure | Acid | Alcohol |
|---|---|---|---|
| methyl laurate | 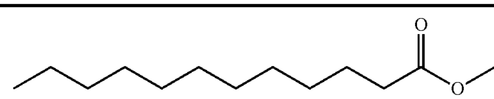 | 12 | 1 |
| ethyl laurate | 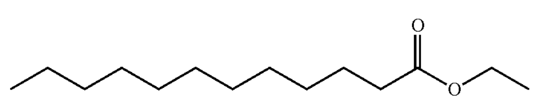 [SMILES: CCCCCCCCCCCC(=O)OCC] | 12 | 2 |
| ethyl decanoate | 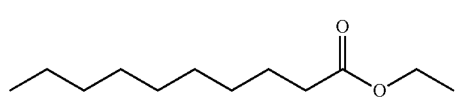 | 10 | 2 |
| ethyl octanoate | 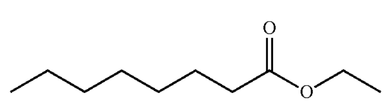 | 8 | 2 |
| methyl decanoate | 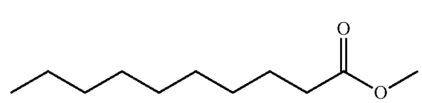 | 10 | 1 |

TABLE 6-continued

Chart of analogues of methyl laurate.

| Solvent | Structure | Acid | Alcohol |
|---|---|---|---|
| methyl heptanoate | 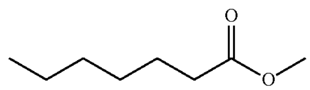 | 7 | 1 |
| methyl hexanoate | 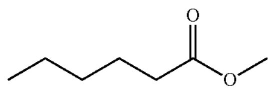 | 6 | 1 |

"Acid" refers to the number of carbons that would be contributed by a parent acid to the daughter ester compound;
"Alcohol" likewise to the parent alcohol.

Example 3

Determination of Solvent Partition Coefficients

Experiments were designed to obtain single point partitioning values relevant to iBuOH toxicity and ISPR biocompatibility. To approximate toxic iBuOH levels during fermentation, aqueous standards were prepared at 3% iBuOH (30 g iBuOH per aqueous L). In addition to pure water, we also examined how composition of the aqueous phase might affect the extraction capability of the solvents under process relevant conditions. To do so, two additional aqueous standards were prepared: 3% iBuOH in minimal growth media, and 3% iBuOH in rich growth media (growth media prepared as per KRL protocol). In all cases, aqueous solutions of 3% iBuOH were extracted at ambient temperature by the solvent panel using an equal volume of aqueous to organic components (1:1) to align with the extraction condition of the primary automated biocompatibility screening. Extractions were carried out in glass vials (containing 750 μL aqueous and 750 μL organic, 1.5 mL total volume) by vigorously mixing for 2 hours (vials were placed in a 96-well plate holder for mixing, 1000 rpm). The equilibration phase partition was verified by time-course studies, wherein most solvents equilibrated in 15 minutes. Although the relative extractability of the panel members at a given condition remained similar, pilot studies indicated that variance in absolute $K_d$ values can arise when keeping the 1:1 ratio constant but changing extraction volumes (e.g., 5:5 mL vs. 750:750 μL) and extraction containers (e.g., 50 mL centrifuge tubes vs. 5 mL vials). Notably, changing the extraction ratio (e.g., from 1:1 to 1:3) should change $K_d$ values more dramatically, as these conditions represents a different point on the phase diagram. The iBuOH content in each phase following extraction and phase separation was determined using gas chromatography (GC method available upon request). To prepare for GC analysis, a sample from each phase was diluted 1:10 into methanol containing an internal standard (0.2% n-propanol volume/volume). Concentrations of iBuOH were determined using an external iBuOH standard curve correlated to the internal n-propanol standard. Method development was used to circumvent discrepancies with standards wherever possible; however, co-elution with the internal standards persisted in the case of ethyl n-butyrate, necessitating the use of only the external standard curve.

Isobutanol concentrations from aqueous and organic phases were used to calculate partition coefficients ($K_d$) according to the following Equation:

$$Kd = \frac{[iBuOH](g/L)org}{[iBuOH](g/L)aq}$$

Table 7 lists the final $K_d$ values (all values generated from triplicate extractions and GC measurements). Preliminary studies indicated that variance in isobutanol measurements arise when samples are directly injected onto the GC versus when they were diluted 1/10 in methanol before GC analysis. All $K_d$ values in Table 7 with an asterisk were determined using the dilution method.

TABLE 7

Solvent panel $K_d$ values

| Solvent | $K_d$ | Std. Error |
|---|---|---|
| oleyl alcohol | 2.23 | 0.15 |
| n-decane | 0.11 | 0.00 |
| methyl laurate | 1.12 | 0.02 |
| di-n-hexyl ether | 0.78 | 0.02 |
| decalin | 0.13 | 0.00 |
| 2-ethyl hexyl acetate | 1.88 | 0.06 |
| 2-ethylhexylglycol ether* | 4.95 | 0.07 |
| 2-ethyl-1-hexanol | 5.51 | 0.15 |
| 2,6-dimethylheptan-4-ol | 4.25 | 0.13 |
| ethyl n-butyrate | 3.57 | 0.44 |
| n-hexyl acetate | 2.23 | 0.04 |
| 1,2-dibutoxyethane | 2.27 | 0.08 |
| n-butyl n-butyrate | 2.17 | 0.06 |
| 2,6-dimethylheptan-4-one | 2.12 | 0.05 |
| ETBE | 2.47 | 0.05 |
| di-n-butyl ether | 1.26 | 0.03 |
| ethylene glycol monohexyl ether | 5.66 | 0.14 |
| MTBE | 4.18 | 0.19 |
| propylene glycol methyl ether acetate | 3.15 | 0.09 |
| isooctane | 0.18 | 0.02 |
| mesitylene | 0.47 | 0.02 |
| acetophenone | 2.95 | 0.07 |
| n-hexanol | 7.41 | 0.23 |
| phenyl acetate* | 1.95 | 0.05 |
| 1-octanol* | 5.19 | 0.20 |
| 8-methylquinoline | 5.03 | 0.20 |
| p-tolualdehyde* | 2.41 | 0.04 |
| 2-octanol | 5.98 | 0.25 |
| Isophorone | 5.68 | 0.15 |
| methyl isobutyl carbinol | 7.78 | 0.15 |
| o-xylene* | 0.85 | 0.02 |
| trimethylnonanol | 3.57 | 0.08 |
| n-butyl propionate* | 3.02 | 0.13 |
| n-propyl propionate* | 3.4 | 0.06 |
| n-butyl acetate* | 3.48 | 0.09 |
| n-pentyl propionate* | 2.94 | 0.03 |
| primary amyl acetate mixed isomers* | 3.67 | 0.05 |
| isobutyl acetate | 3.33 | 0.12 |
| dodecanal | 5.38 | 0.35 |
| UCAR filmer IBT | 4.16 | 0.06 |

TABLE 7-continued

Solvent panel $K_d$ values

| Solvent | $K_d$ | Std. Error |
|---|---|---|
| n-butyl valerate | 2.04 | 0.01 |
| di-n-octyl ether | 0.55 | 0.01 |
| isobutyl heptyl ketone | 1.49 | 0.01 |
| dodecane | 0.18 | 0.01 |
| n-undecane | 0.20 | 0.01 |
| dodecanol | 3.39 | 0.06 |
| ethyl octanoate | 1.81 | 0.02 |
| ethyl decanoate | 1.40 | 0.02 |
| ethyl dodecanoate | 1.26 | 0.01 |
| methyl decanoate | 1.42 | 0.02 |
| methyl hexanoate | 2.47 | 0.04 |
| methyl heptanoate | 2.07 | 0.02 |

\*indicates $K_d$ values measured using the dilution technique. 3% iBuOH water, extracted 1:1 with solvent (n = 3), a-Standard Error calculated as $(\sigma_{Kd}/\sqrt{n})$ where $\sigma_{Kd}$ = standard deviation of $K_d$ and n = number of replicates. Formula for $\sigma_{Kd} = \sqrt{[(\sigma_{Aq}^2/\mu_{Org}^2) + (\mu_{Aq}^2/\mu_{Org}^4)]}$ where $\sigma$ = standard deviation, $\mu$ = average, Aq = value from the aqueous layer, and Org = value from the organic layer.

Example 4

Enhancement of Extraction Efficiency of a Biocompatible Solvent by Mixing with a High $K_d$ Solvent In order to enhance the extraction efficiency of a biocompatible solvent, it was determined that when mixed with a high $K_d$, low biocompatibility solvent, a high $K_d$, high biocompatibility extractant composition is obtained. A preliminary test was performed with the automated primary screen protocol to evaluate the feasibility of mixtures as a process strategy. A factorial design was conducted using three biocompatible solvents (oleyl alcohol, methyl laurate and trimethylnonanol) paired with four high $K_d$ solvents (n-hexanol, methyl isobutyl carbinol, 2-ethyl-1-hexanol, and 2,6-dimethylheptan-4-ol) at five proportions (0, 25, 50, 75 and 100% high $K_d$ solvent) in triplicate. Based on the viability data, the most biocompatible combination was carried forward to tertiary screening.

The primary screen indicated that mixtures of a biocompatible solvent with 2,6-dimethylheptan-4-ol resulted in low levels of cell death when used as the organic extractant (FIG. 15). Among the solvent mixtures that were biocompatible, a combination of oleyl alcohol and 2,6-dimethylheptan-4-ol in a 75%:25% ratio was shown to support isobutanol production—1 g/L in 48 h (FIG. 17). The solvent mixture has an interpolated $K_d$ value of 3.8, which represents a 1.7 fold improvement when compared to oleyl alcohol alone.

What is claimed is:

1. A method for recovering butanol from a fermentation medium, the method comprising:
    (a) providing a fermentation medium comprising butanol, water, and a recombinant microorganism comprising a butanol biosynthetic pathway, wherein the recombinant microorganism produces butanol;
    (b) contacting the fermentation medium with a water immiscible organic extractant composition comprising a solvent selected from the group consisting of $C_{12}$ to $C_{22}$ fatty alcohols, $C_{12}$ to $C_{22}$ ethers, esters of $C_{12}$ to $C_{22}$ fatty acids, $C_{10}$ to $C_{22}$ alkanes, and mixtures thereof, to form a butanol-containing organic phase and an aqueous phase,
    wherein the solvent is biocompatible with the microorganism such that at least about 90% of the microorganisms are viable after exposure to the organic extractant composition, and wherein the solvent has a boiling point less than about 300° C, with the proviso that the organic extractant is not oleyl alcohol, 1-dodecanol, behenyl alcohol, cetyl alcohol, myristyl alcohol, or stearyl alcohol; and
    (c) recovering the butanol from the butanol-containing organic phase.

2. The method of claim 1, wherein the solvent is trimethylnonanol, methyl laurate, di-n-octyl ether, dodecane, n-undecane, ethyl decanoate, ethyl laurate, or mixtures thereof.

3. A method for recovering butanol from a fermentation medium, the method comprising:
    (a) providing a fermentation medium comprising butanol, water, and a recombinant microorganism comprising a butanol biosynthetic pathway, wherein the recombinant microorganism produces butanol;
    (b) contacting the fermentation medium with a water immiscible organic extractant composition comprising a solvent is trimethylnonanol, methyl laurate, di-n-octyl ether, dodecane, n-undecane, ethyl decanoate, ethyl laurate, or mixtures thereof, to form a butanol-containing organic phase and an aqueous phase; and
    (c) recovering the butanol from the butanol-containing organic phase.

4. The method of claim 1, wherein the contacting of the organic extractant composition with the fermentation medium occurs in a fermentor.

5. The method of claim 1, further comprising: transferring a portion of the fermentation medium from the fermentor to a vessel, wherein the contacting of the organic extractant composition with the fermentation medium occurs in the vessel.

6. The method of claim 1, wherein the butanol is isobutanol.

7. The method of claim 1, wherein the organic extractant composition further comprises an additional solvent, wherein the additional solvent is n-hexanol, methyl isobutyl carbinol, 2-ethyl-1-hexanol, 2,6-dimethylheptan-4-ol, or mixtures thereof.

8. The method of claim 7, wherein the additional solvent is 2,6-dimethylheptan-4-ol.

9. The method of claim 1, wherein the organic extractant composition further comprises an additional solvent with a butanol partition coefficient greater than about 4.

10. The method according to claim 9, wherein the organic extractant composition further comprises an additional solvent, wherein the additional solvent is n-hexanol, methyl isobutyl carbinol, 2-ethyl-1-hexanol, 2,6-dimethylheptan-4-ol, or mixtures thereof.

11. The method of claim 10, wherein the additional solvent is 2,6-dimethylheptan-4-ol.

12. The method of claim 1, wherein the contacting comprises contacting the fermentation medium via a co-current or counter-current stream of the organic extractant composition.

13. The method of claim 1, wherein the recovered butanol has an effective titer from about 22 g per liter to about 40 g per liter of the fermentation medium.

14. The method of claim 1, wherein the recovered butanol has an effective titer of at least about 37 g per liter of the fermentation medium.

15. A composition comprising a solution of butanol in a water immiscible organic extractant composition, wherein the organic extractant composition comprises a solvent selected from the group consisting of $C_{12}$ to $C_{22}$ fatty alcohols, $C_{12}$ to $C_{22}$ ethers, esters of $C_{12}$ to $C_{22}$ fatty acids, $C_{10}$ to $C_{22}$ alkanes, and mixtures thereof, wherein the solvent is biocompatible with a recombinant microorganism comprising a butanol biosynthetic pathway, wherein at least 90% of the recombinant microorganisms are viable after exposure to the organic extractant composition, and wherein the solvent has a boiling point less than about 300° C., with the proviso that the solvent is not oleyl alcohol, 1-dodecanol, behenyl alcohol, cetyl alcohol, myristyl alcohol, or stearyl alcohol.

16. The composition of claim 15, wherein the solvent is trimethylnonanol, methyl laurate, di-n-octyl ether, dodecane, n-undecane, ethyl decanoate, ethyl laurate, or mixtures thereof.

17. The composition of claim 15, wherein the organic extractant composition further comprises an additional solvent, wherein the additional solvent is n-hexanol, methyl isobutyl carbinol, 2-ethyl-1-hexanol, 2,6-dimethylheptan-4-ol, or mixtures thereof.

18. The composition of claim 17, wherein the additional solvent is 2,6-dimethylheptan-4-ol.

19. The composition of claim 15, wherein the butanol is isobutanol.

* * * * *